(12) United States Patent  
Noble

(10) Patent No.: US 7,047,969 B2
(45) Date of Patent: May 23, 2006

(54) NASAL GAS DELIVERY SYSTEM AND METHOD FOR USE THEREOF

(75) Inventor: James P. Noble, Stuart, FL (US)

(73) Assignee: Linda Noble, Stuart, FL (US)

( * ) Notice: Subject to any disclaimer, the term of this patent is extended or adjusted under 35 U.S.C. 154(b) by 0 days.

(21) Appl. No.: 10/959,110

(22) Filed: Oct. 7, 2004

(65) Prior Publication Data

US 2005/0103346 A1    May 19, 2005

Related U.S. Application Data

(63) Continuation-in-part of application No. 10/639,474, filed on Aug. 13, 2003, now Pat. No. 6,848,446, which is a continuation-in-part of application No. 10/183,498, filed on Jun. 28, 2002, now Pat. No. 6,637,434, which is a continuation-in-part of application No. 09/430,038, filed on Oct. 29, 1999, now Pat. No. 6,561,193.

(60) Provisional application No. 60/106,271, filed on Oct. 30, 1998, provisional application No. 60/402,713, filed on Aug. 13, 2002, provisional application No. 60/442,065, filed on Jan. 24, 2003, provisional application No. 60/508,872, filed on Oct. 7, 2003, provisional application No. 60/536,997, filed on Jan. 20, 2004, provisional application No. 60/570,116, filed on May 12, 2004, provisional application No. 60/591,875, filed on Jul. 29, 2004.

(51) Int. Cl.
*A61M 16/00*    (2006.01)

(52) U.S. Cl. .............................. 128/206.11; 128/207.18

(58) Field of Classification Search ........... 128/200.26, 128/207.14, 207.15, 207.18, 206.11
See application file for complete search history.

(56) References Cited

U.S. PATENT DOCUMENTS

| | | | | |
|---|---|---|---|---|
| 5,056,514 A | * | 10/1991 | DuPont | ................. 128/207.14 |
| 5,655,518 A | * | 8/1997 | Burden | .................. 128/200.26 |
| 6,533,984 B1 | * | 3/2003 | Curti | .......................... 264/219 |

* cited by examiner

*Primary Examiner*—Teena Mitchell
(74) *Attorney, Agent, or Firm*—Wenderoth, Lind & Ponack, L.L.P.

(57) ABSTRACT

A gas administering method for administering gas to an airway of a patient having a nasal vestibule and for use with a gas administering apparatus comprises a primary gas source that is operable to provide gas and a nasal vestibular portion arranged so as to receive the gas from the primary gas source. Further, the nasal vestibular portion is capable of releasing the primary gas into the nasal vestibule. The method comprises inserting the nasal vestibular portion into the nasal vestibule, forming a seal between the nasal vestibular portion and an inner surface of the nasal vestibule, administering an amount of a gas from the primary gas source at a constant flow rate into the nasal vestibule via the nasal vestibular portion, and administering an anesthetic to the patient. The anesthetic induces depression of a portion of the nervous system of the patient. Furthermore, the seal promotes airway pressure buildup that is sufficient to prevent obstruction of the airway during depression of at least a portion of the nervous system and prevents escape of the gas from between the nasal vestibule and the nasal vestibular portion.

8 Claims, 37 Drawing Sheets

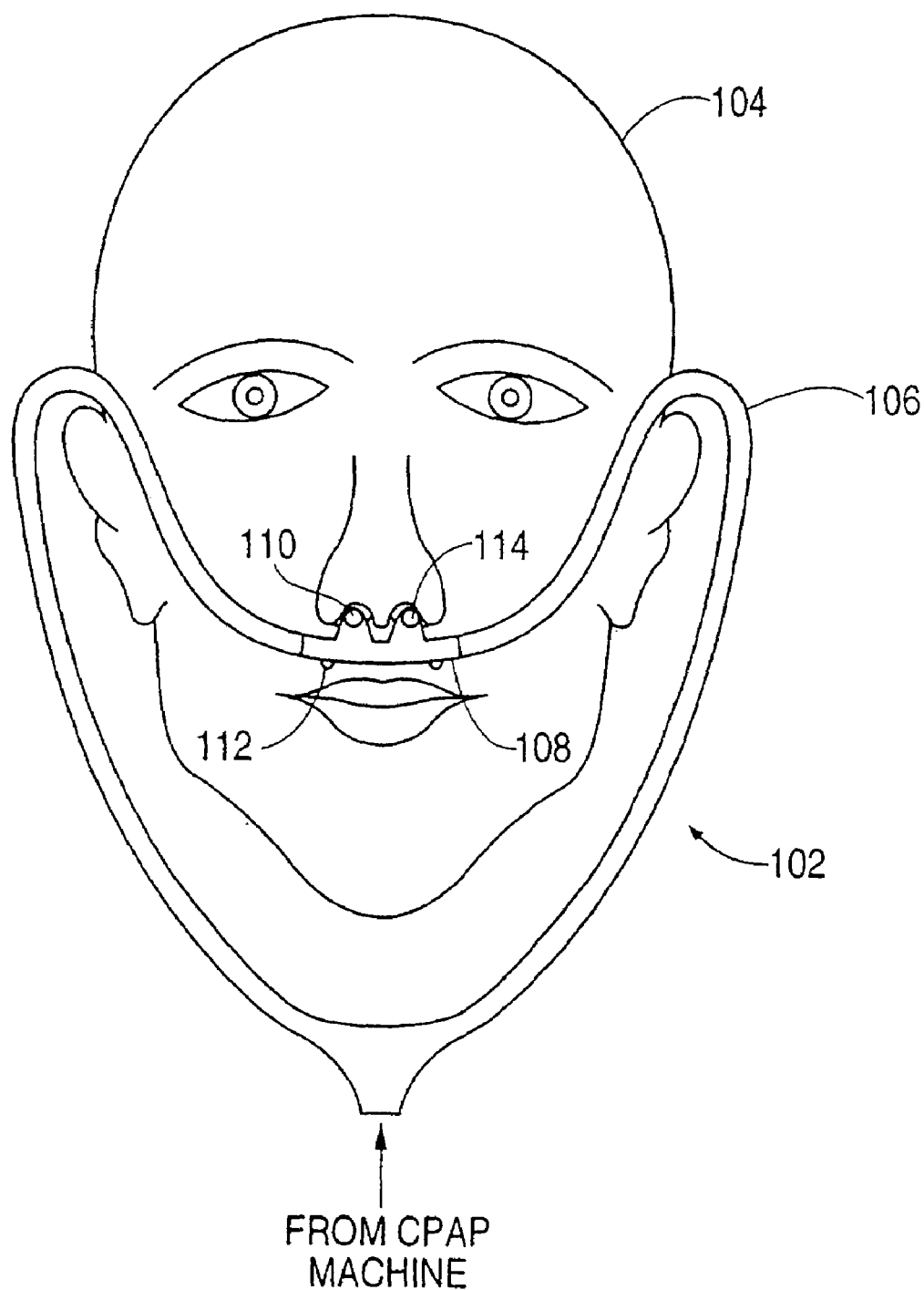

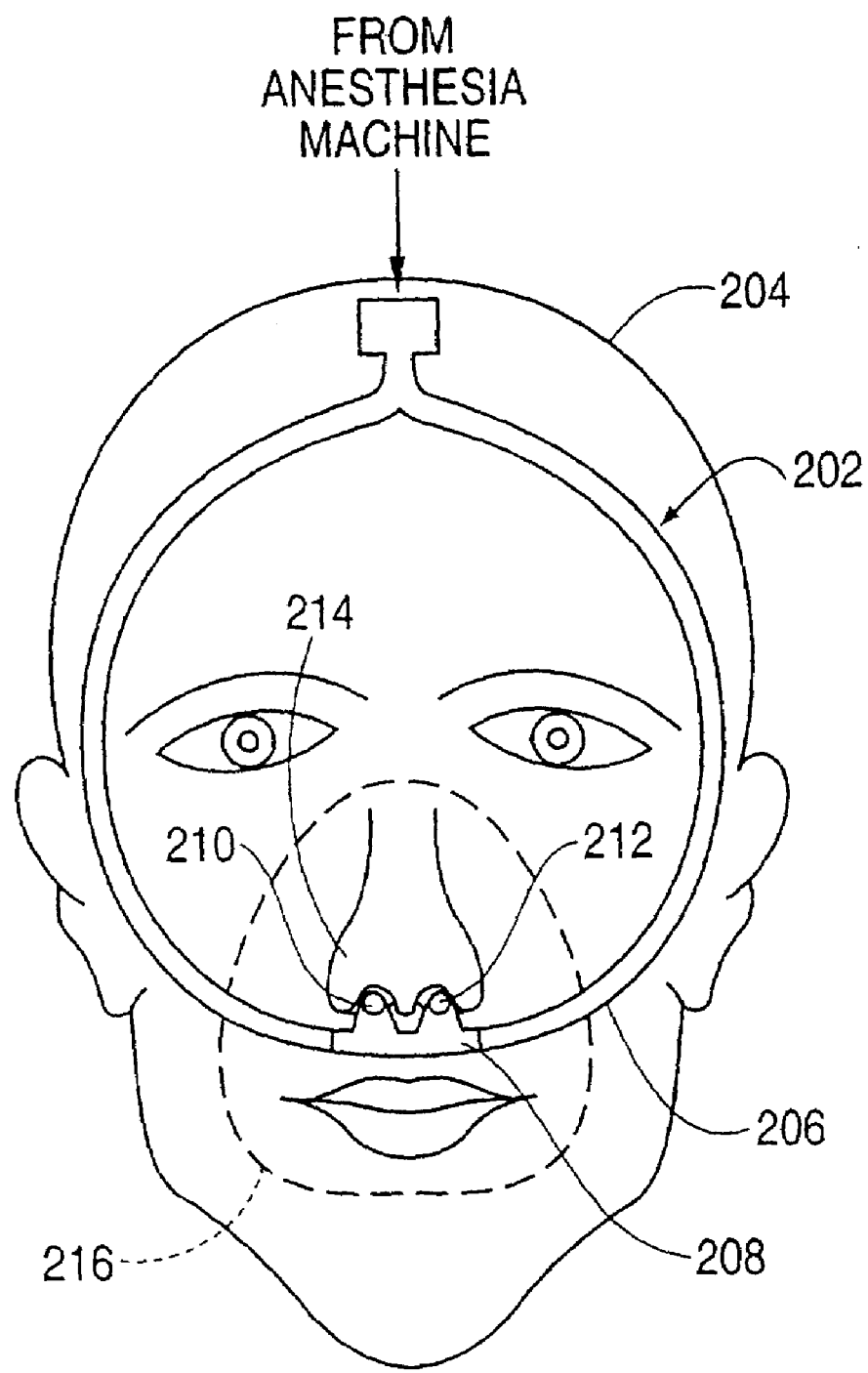

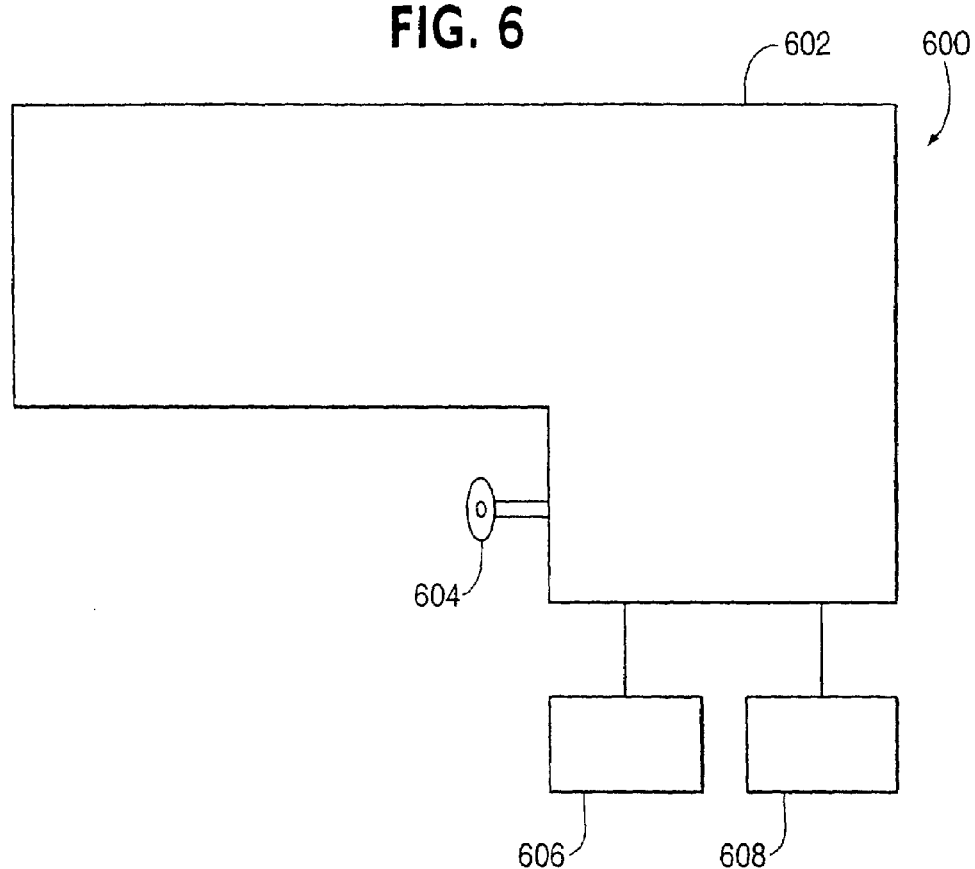

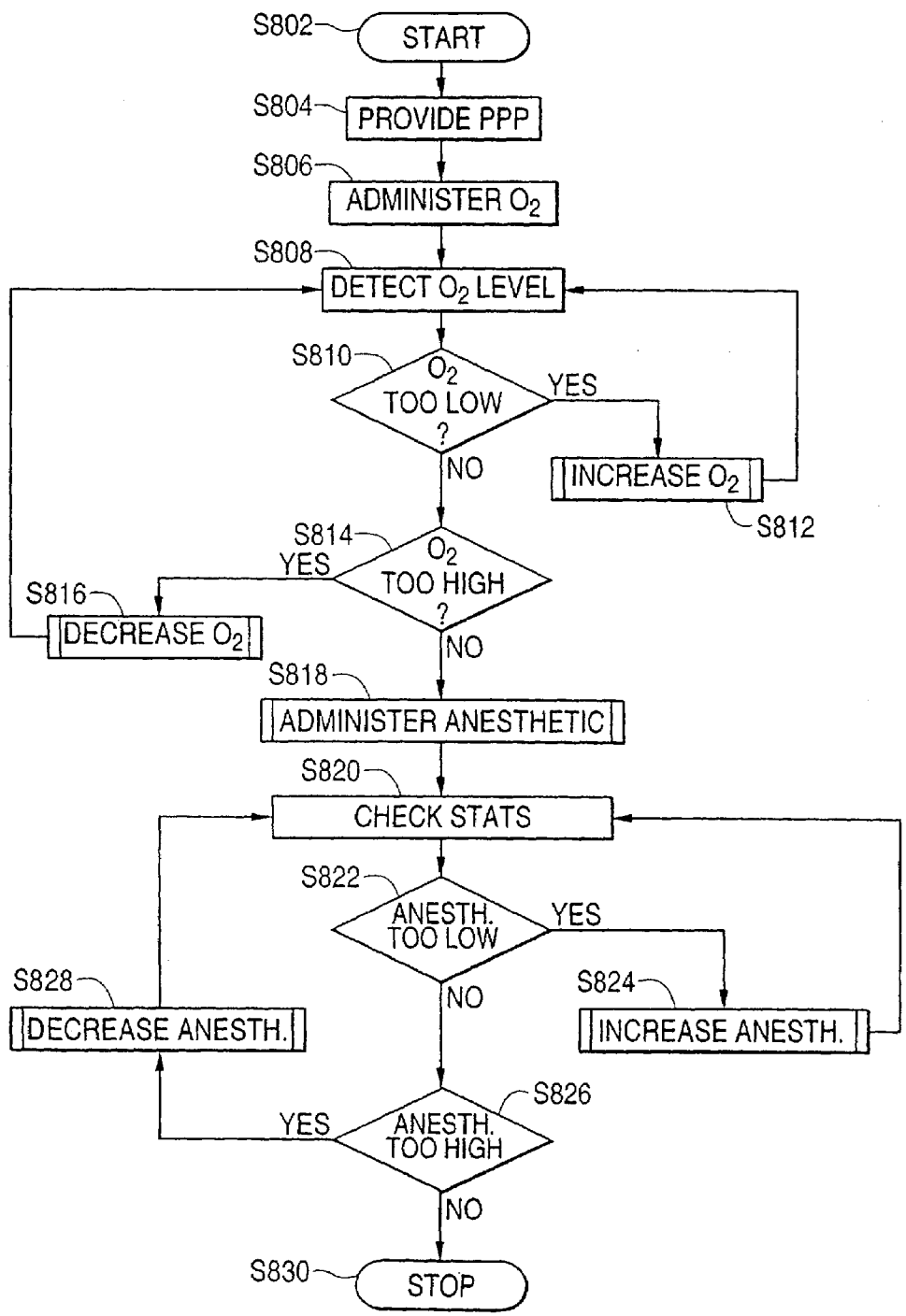

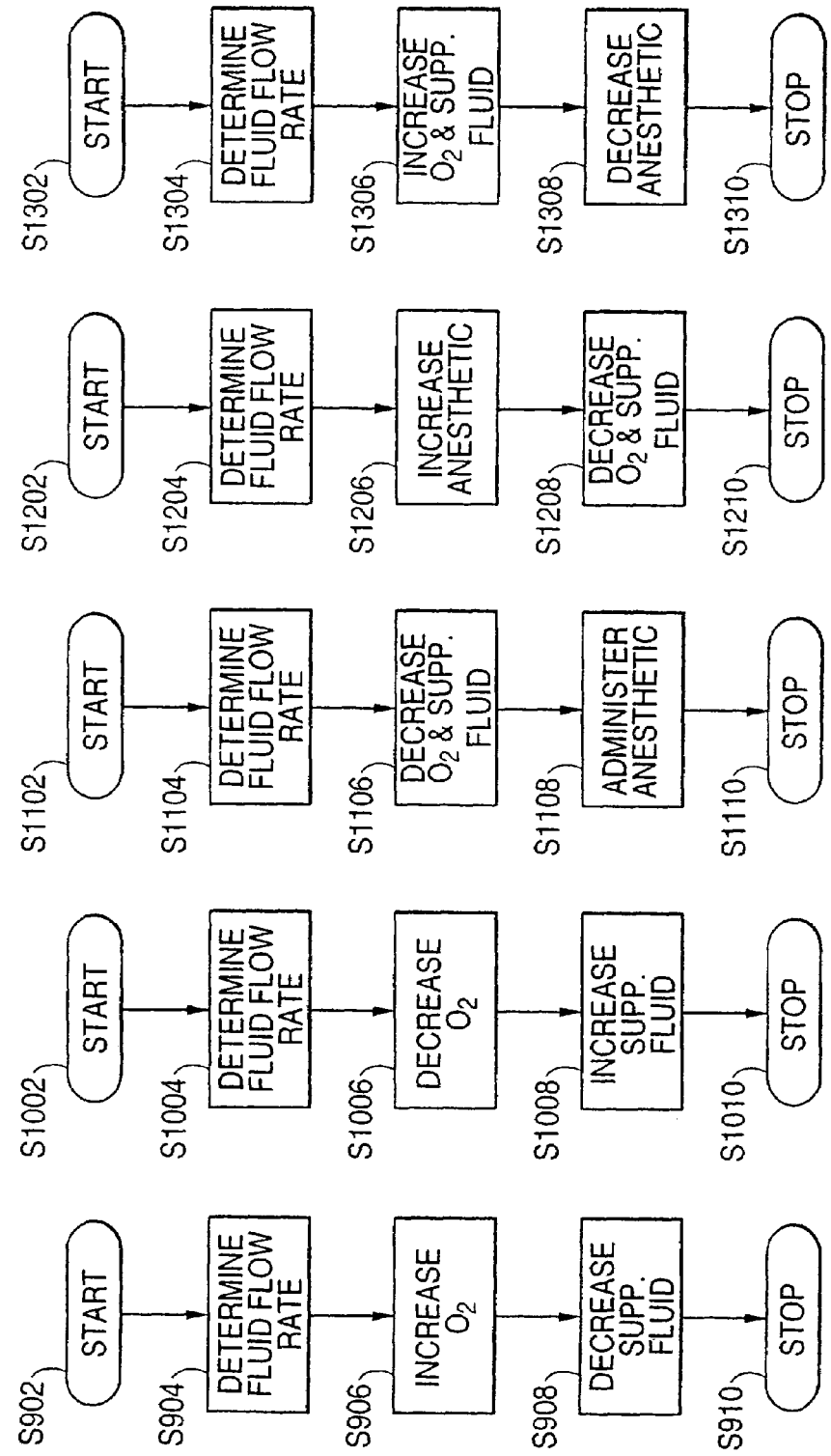

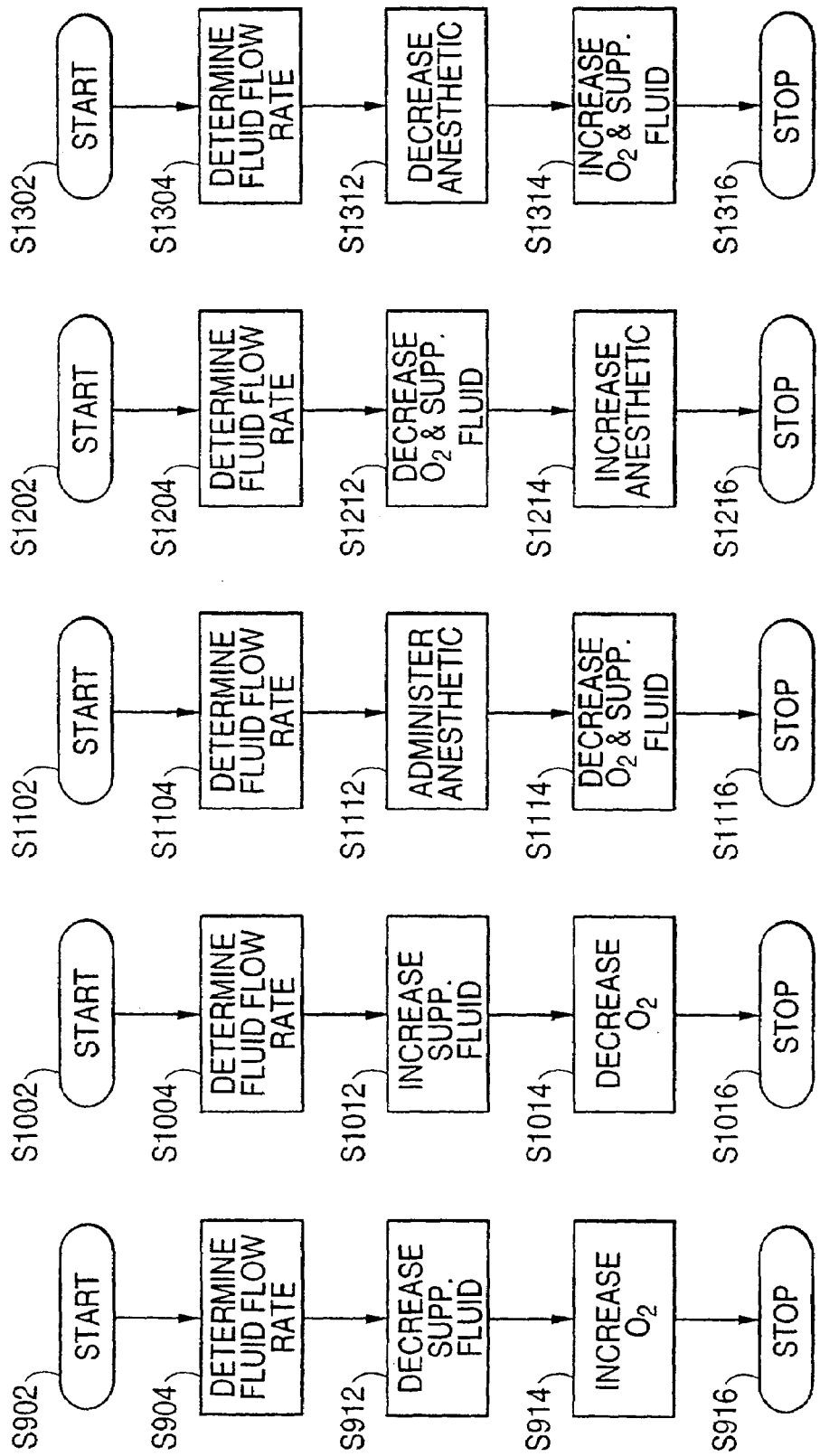

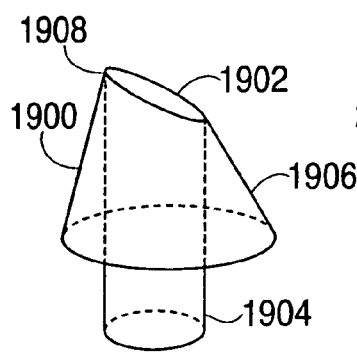
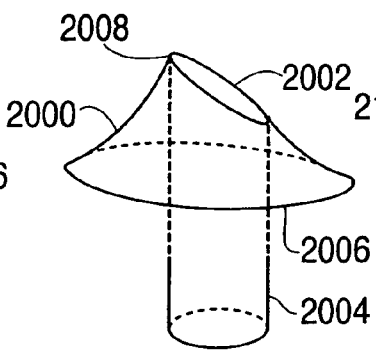
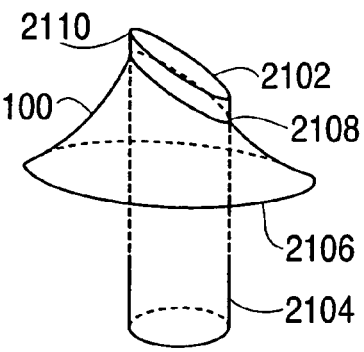
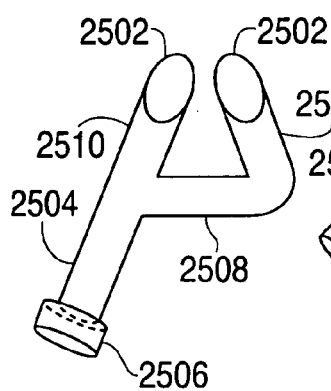
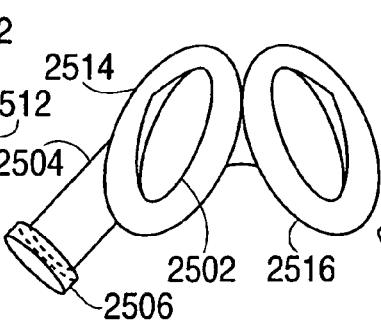
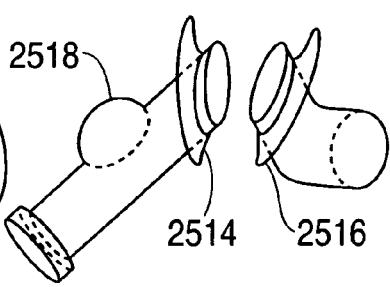
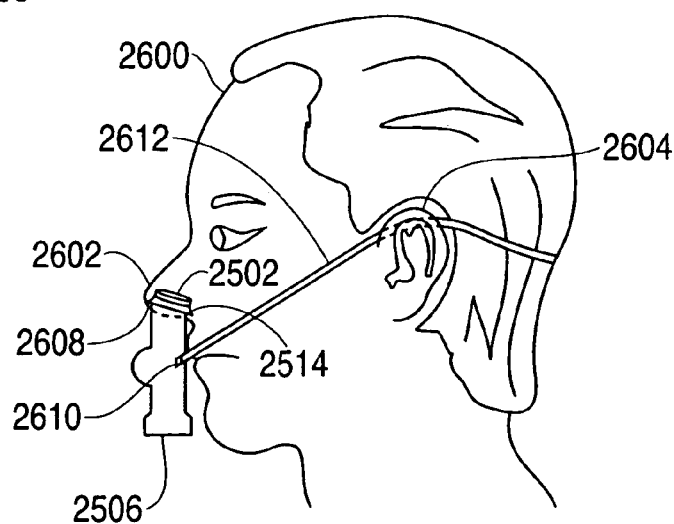

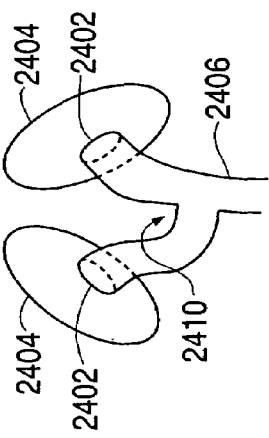
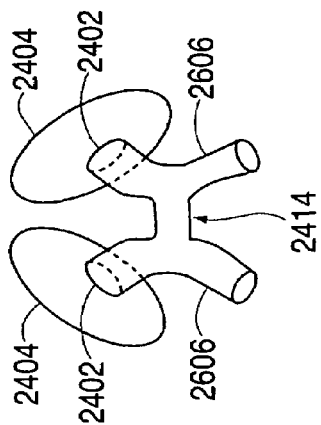
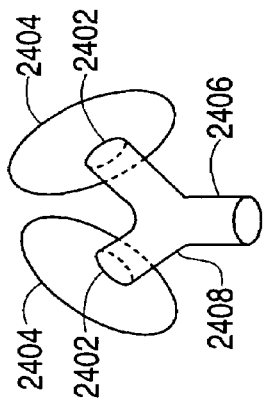
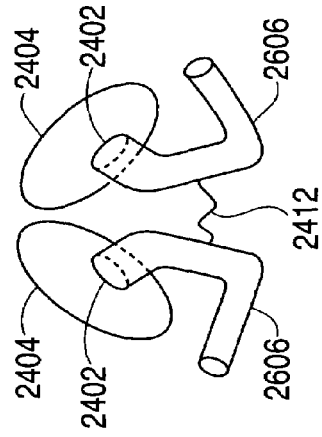
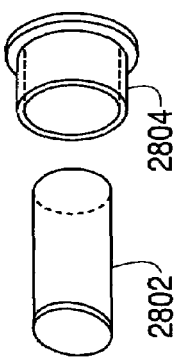
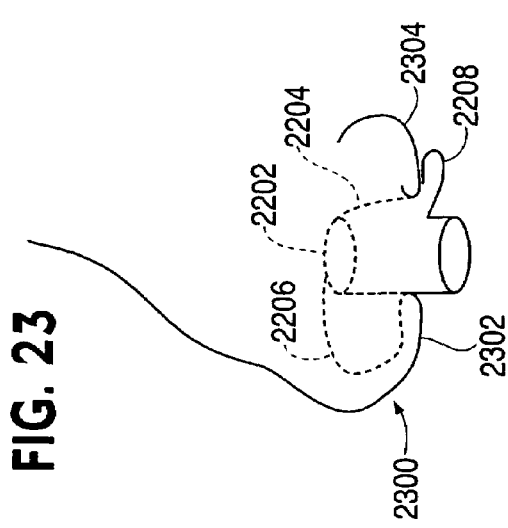
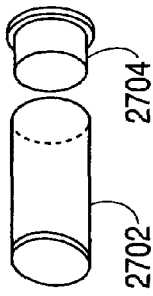

4112

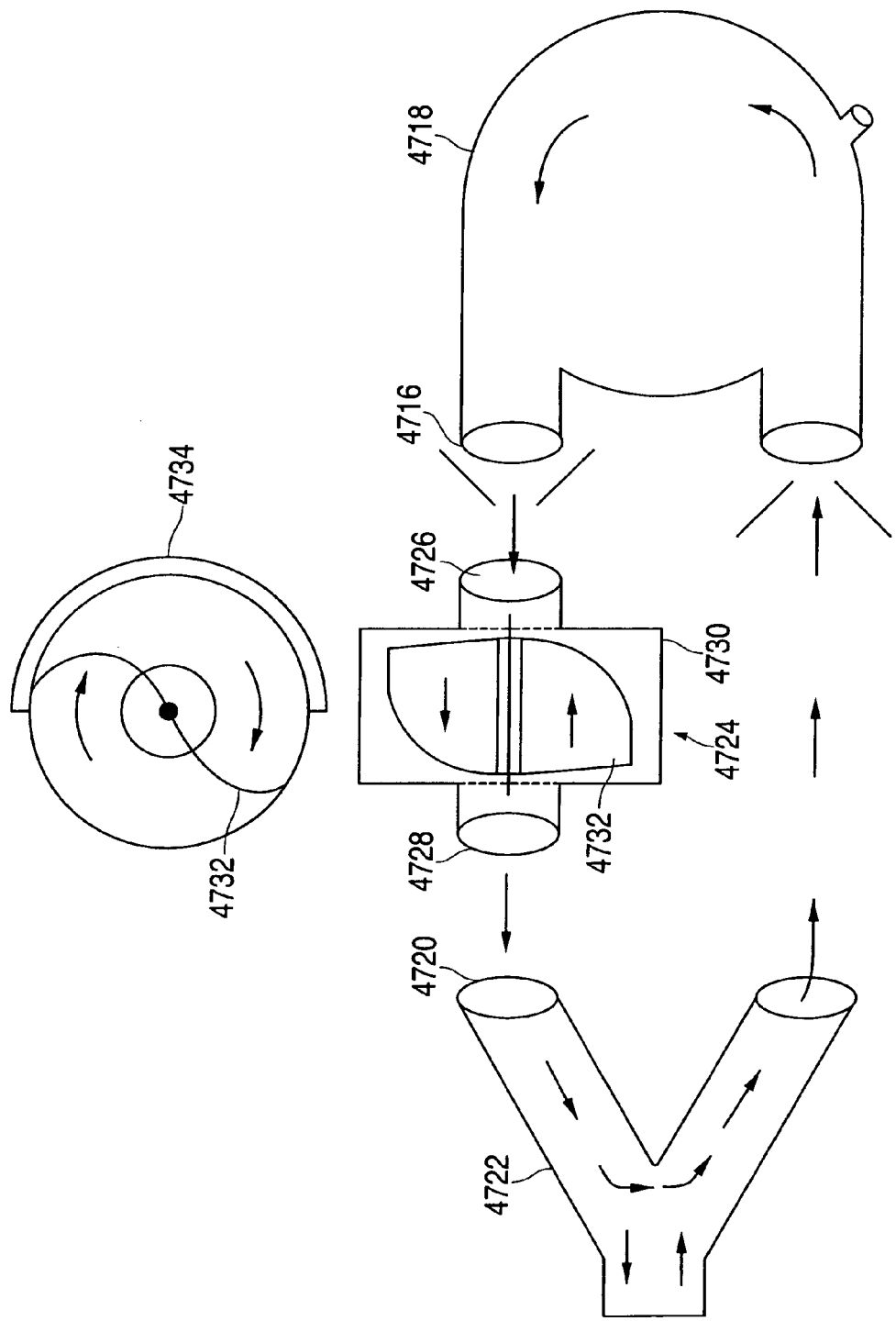

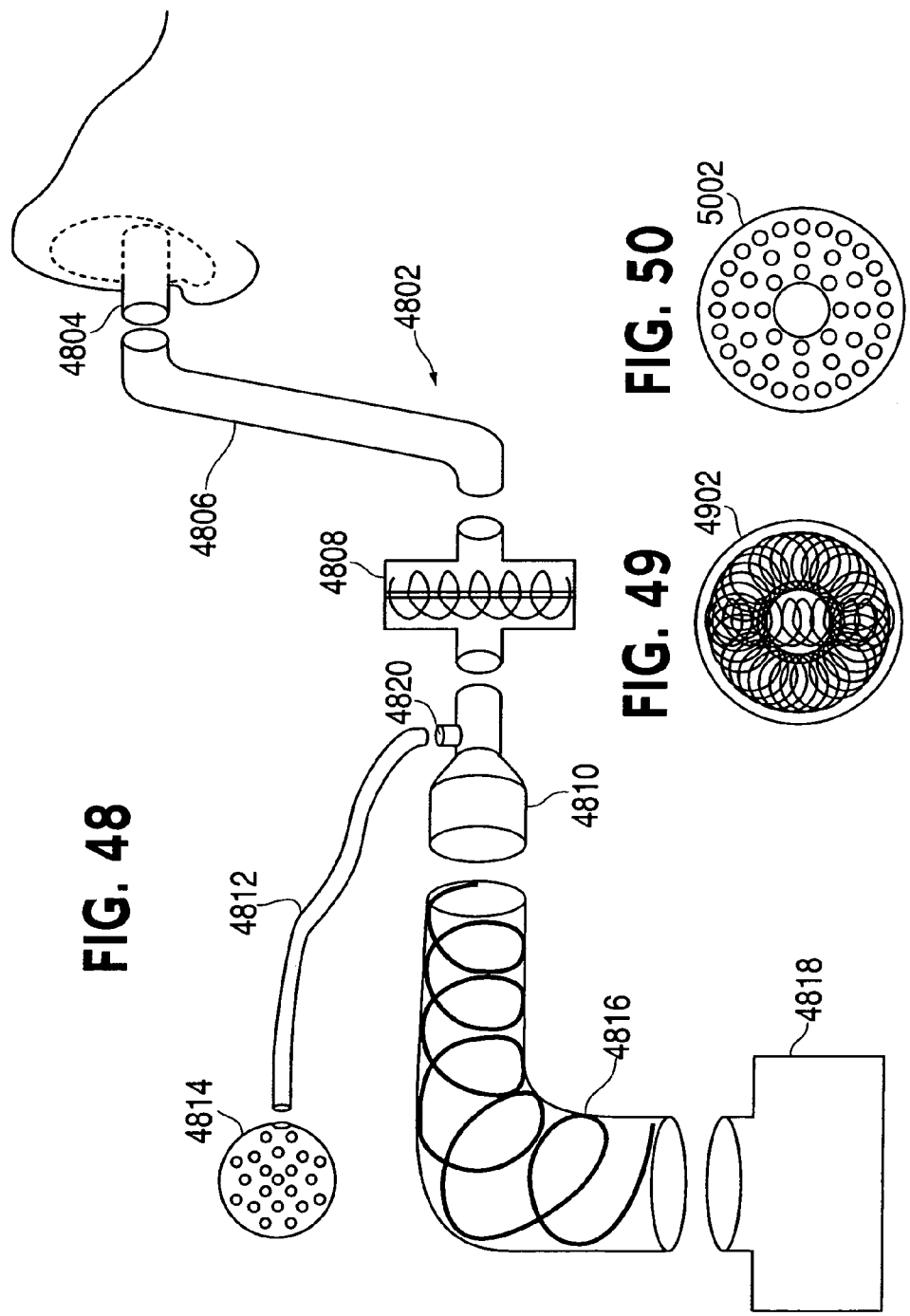

NASAL GAS DELIVERY SYSTEM AND METHOD FOR USE THEREOF

This is a Continuation-In-Part Application of Utility Application having Ser. No. 10/639,474, filed Aug. 13, 2003 now U.S. Pat. No. 6,848,446, which is a Continuation-In-Part Application of Utility Application having Ser. No. 10/183,498, filed Jun. 28, 2002 now U.S. Pat. No. 6,637,434, which is a Continuation-In-Part Application of Utility application having Ser. No. 09/430,038, filed Oct. 29, 1999 now U.S. Pat. No. 6,561,193, which claims priority on Provisional Application 60/106,271, filed Oct. 30, 1998. The present Application additionally claims priority to Provisional Application having Ser. No. 60/402,713, filed Aug. 13, 2002 and to Provisional Application having Ser. No. 60/442,065, filed Jan. 24, 2003, to Provisional Application having Ser. No. 60/508,872, filed Oct. 7, 2003, to Provisional Application having Ser. No. 60/536,997, filed Jan. 20, 2004, to Provisional Application having Ser. No. 60/570,116, filed May 12, 2004, and to Provisional Application having Ser. No. 60/591,875, filed Jul. 29, 2004. The entire disclosures of applications having Ser. Nos. 10/639,474, 10/183,498, 09/430,038, 60/106,271, 60/402,713, 60/442,065, 60/508,872, 60/536,997, 60/570,116, and 60/591,875 are incorporated herein by reference.

BACKGROUND OF THE INVENTION

The present invention relates to a gas delivery apparatus for administering a gas to a patient during surgery, and more particularly for delivering anesthetic to a patient during surgery.

During surgical procedures, there is a need to anesthetize a patient in order to eliminate, or at least reduce: pain associated with the procedure; and movement of the patient during the procedure. Anesthesia is considered a drug-induced depression of at least a portion of nervous system, or portion thereof, of the patient.

In the sequence of events of drug-induced depression of the central nervous system, there occurs a level of depression that allows the muscles of the pharynx (e.g. the tongue) to relax causing soft-tissue structures to collapse into and obstruct the airway. This happens at an earlier stage than that at which the muscles of respiration (e.g. the diaphragm) cease to function. In other words, a condition known as "obstructive apnea," where the diaphragm is struggling to pull air through an obstruction of the upper airway occurs before the diaphragm itself ceases to function ("central apnea"). In this sequential depression of the central nervous system, death occurs from Asphyxia before the drug itself can produce complete depression of the nervous system.

Similarly, even partial obstruction will cause disastrous consequences of an immediate and/or long-term nature. For example the resulting hypoxia (i.e., oxygen deficiency) will cause a reflex constriction of blood vessels in the lungs leading to pulmonary hypertension and the right portion of the heart's failure to pump blood efficiently through the lungs to the left portion of the heart. Accordingly, the heart is unduly taxed and the circulatory reserves of well oxygenated blood are impaired. The resulting hypercarbia (i.e., the abnormal accumulation of carbon dioxide) will cause acidosis (i.e., the accumulation of acid) leading to depression of organ systems. The central nervous system, for instance, will become progressively depressed to a deep coma directly related to the level of retained carbon dioxide. Further, the resulting stronger negative intra-thoracic pressure, that is generated by the bellows action of the diaphragm pulling on the chest cavity as the patient attempts to draw air through an obstructed upper airway, leads to two problems. First, a greater negative intra-pulmonary pressure (i.e., the negative pressure transmitted to inside the lungs) dilates small blood vessels to cause excessive blood flow around the alveoli (i.e., the small air sacs). Concurrently, a vacuum is created which sucks fluid out of the circulation to fill the void generated within the alveoli. Hypoxia ensues, first, from the mismatch of circulation to ventilation and, then, rapidly deteriorates as pulmonary edema (i.e., fluid in the air sacs) worsens. Second, a greater negative pressure in the chest cavity is also transmitted to the esophagus. An esophageal pressure more negative, relative to the pressure within the stomach, establishes a pressure gradient which favors the reflux of gastric acid up the esophagus where it will burn pharyngeal structures and, if aspirated into the lungs, will cause severe and, sometimes, fatal destruction of lung tissue.

An upper airway obstruction occurs upon the induction of almost every general anesthetic and is a frequent occurrence during the administration of heavy sedation for procedures done nominally under "local anesthesia with sedation." Under most conditions, the treatment is so routine as to be taken for granted by practitioners skilled in airway management.

The condition which has been called SNOR (Syndrome of Narcogenic Obstructive Respiration) is a common occurrence in the practice of anesthesia. Drugs, which induce depression of the central nervous system to prevent the perception of pain, concurrently induce upper airway obstruction. Many airway devices and methods are used to alleviate the problem. One method, not yet widely practiced, involves the delivery of air and/or oxygen and anesthetic gases under positive pressure through the nose of the patient to prevent airway obstruction in a fashion very similar to that used in the home therapy of Obstructive Sleep Apnea (OSA). In SNOR, however, a nasal appliance is connected to any of several commonly-employed anesthesia circuits of tubing which are connected to anesthesia machines and/or other sources of oxygen, air and anesthetic gases. Gas flows can be used to generate the relatively low pressures through the nose that will usually relieve upper airway obstruction and allow spontaneous respiration.

Another common occurrence in the practice of anesthesia, in addition to SNOR, is the use of 100% oxygen or oxygen mixed with nitrous oxide. Nitrous oxide, itself, supports combustion and any combination of the two gases, when allowed onto the surgical field, will find plenty of fuel (e.g., plastic and paper drapes, hair, etc.) and ready sources of ignition (e.g., electro-cautery, LASER, fiberoptic lights, etc.). This potential joining of the three sides of the "fire triangle" can result in a chain reaction that is often explosive in its evolution and is the cause of, ". . . approximately 100 surgical fires each year, resulting in up to 20 serious injuries and one or two patient deaths annually." (SENTINEL EVENT ALERT, Jun. 24, 2003, from the Joint Commission on Accreditation of Healthcare Organizations)

Other problems are associated with the use of high concentrations of oxygen and nitrous oxide. High oxygen concentrations over many hours can induce severe inflammation of the lungs and respiratory distress. Further, without nitrogen to keep them inflated, 100% oxygen is rapidly absorbed from under-ventilated alveoli, allowing them to collapse causing "absorption hypoxia" and a predisposition to pneumonia. Still further, nitrous oxide diffuses so rapidly from the circulation into the alveoli at the end of anesthesia that adequate oxygen can be prevented from entering the alveoli.

The solution to the above problems is as simple as eliminating nitrous oxide, the use of which is more traditional than helpful, and adding air to all anesthetic gases. The nitrogen in air dilutes the oxygen and absorbs heat to impede the chain reaction of combustion. The real problem is that many anesthesia settings do not have the capability to deliver air to the mixture of anesthesia gases. Operating rooms often have not been piped for air and many anesthesia machines are not designed to deliver air. Moreover, compressed "medical air" is expensive. Manual support of the airway such as with an invasive endotracheal tube, application of a face mask over the mouth and nose and various other airway devices are employed, often with supplemental oxygen.

However, the use of a face mask or an endotracheal tube during surgical procedures has many drawbacks. The standard face mask places pressure on the chin and tends to collapse soft-tissue structures of the oropharynx. Additionally, air pressure that is applied through the face mask tends to equalize through the nose and the mouth, and therefore it can be counter-productive to the supporting of soft tissue to open the airway. Further, using a face mask usually requires one or two additional maneuvers, for example manual support of the chin, the insertion of an oral airway, etc., in order to remedy the problem. None of the invasive airway-support devices currently used in conventional anesthesia practice can be inserted in the conscious patient without causing significant discomfort and/or physiological disturbance.

Furthermore, recent advances in cosmetic surgery have made airway management significantly more challenging and have caused practitioners to accept conditions having a reduced margin of safety for their patients. In particular, laser procedures on the face are requiring heavier sedation leading more often to respiratory depression and obstruction while, at the same time, the increased fire hazard restricts the use of oxygen.

Obstructive Sleep Apnea (OSA), a syndrome defined in the early 1980's, is similar to drug-induced obstructive apnea in anatomy and treatment. The treatment of OSA has demonstrated that upper airway obstruction occurring during the sleep of afflicted patients can be relieved by the application of positive pressure through the nose alone. OSA differs from drug-induced obstructive apnea in that it is not drug-induced. Further, OSA typically does not have acutely disastrous consequences, but rather has long-term ill-effects and is a chronic condition.

A conventional method for treating a form of OSA is to provide a continuous positive airway pressure (C-PAP) through the nose in order to prevent an upper airway obstruction. Nasal masks are used, as are nasal insert devices. InnoMed Technologies, for instance, provides a device called NasalAire used to treat obstructive sleep apnea. The device includes conical shaped nasal inserts connected to gas delivery tubes which are connected to an air delivery system. A C-PAP generator is included, which automatically increases and decreases air flow rate to maintain a continuos positive airway pressure. Furthermore, the device includes vent holes for venting $CO_2$ from the exhaling user.

FIG. 1 illustrates a conventional system for treating sleep induced apnea by providing a constant positive airway pressure through the nose. As depicted in the figure, the patient 104 is fitted with tubing 102. The tubing 102 receives airflow from a C-PAP machine and administers the airflow to the nose of the patient by tube branches 106. An airflow delivery device 108, having nasal inserts 110 is placed such that nasal inserts 110 are disposed within the nasal vestibules 114 of patient 104. Airflow delivery device 108 additionally includes ventilation holes 112, which provide ventilation for $CO_2$ from the user during expiration. Examples of such devices are disclosed in U.S. Pat. No. 5,533,506 to Wood, U.S. Pat. No. 4,702,832 to Tremble et al, and U.S. Pat. No. 5,134,995 to Gruenke et al., the entire disclosures of which are incorporated herein by reference.

What is needed is a method and apparatus for preventing complete airway obstruction of a patient when the patient is deeply sedated after induction of anesthesia.

What is additionally needed is a method and apparatus for enabling a patient to adequately respire at surgical levels of anesthesia without an invasive airway and manual or mechanized ventilation.

What is additionally needed is a method and apparatus for cost-effectively adding air to the anesthetic gasses for reducing the risk of combustion in the surgical field when using cautery or laser devices.

What is additionally needed is a method and apparatus for preventing leakage of the anesthesia to the operating room.

What is additionally needed is a method and apparatus for more accurately monitoring spontaneous respirations in a pressurized system.

What is additionally needed is a method and apparatus for preventing an airflow generator from excessively pressurizing an anesthesia circuit.

What is additionally needed is an apparatus that is: operably connectable to an existing anesthetic delivery apparatus; operable to prevent complete airway obstruction of a patient when the patient is deeply sedated after induction of anesthesia; and operable to enable a patient to adequately respire at surgical levels of anesthesia without an invasive airway and manual or mechanized ventilation.

What is additionally needed is an inexpensive method of adding air to the various breathing circuits used in the operating room, recovery room and other critical care areas. An airflow generator which does not store air in a compression tank, but immediately delivers it to the patient, could provide the same ambient air that the patient would be breathing on his own, if not being treated, and would draw from the same safe air supply breathed by those healthcare providers in attendance. Moreover, if a filter were attached to the airflow generator then the patient would, in theory, be breathing air more pure than ambient air.

As opposed to a conventional continuous-pressure airflow generator (i.e.,"C-PAP machine"), what is additionally needed is an airflow generator operable to generate a constant flow rate and allow the airway pressure to vary.

What is additionally needed, is a device (adapter) which could convert a standard "C-PAP Machine" from continuous-pressure air delivery to continuous-flow air delivery.

What is needed, is a reliable continuous breath-by-breath monitor of the breathing circuit and the patency of the upper airway of the patient. A stethoscope designed to fit in-line with the tubing of the breathing circuit would transmit the unique combined sounds of airflow through the circuit and upper airway of the patient. Such a stethoscope would give the earliest warning of impending airway obstruction and allow corrective action to be taken within a breath of discovery with immediate feedback as to the effectiveness of the remedy.

What is further needed is a simple and inexpensive mechanical monitor of inspiratory flow.

If the patient is intubated for general anesthesia, at the end of the surgical procedure, C-PAP may be applied as the patent is extubated relatively deep and unreactive to the endotracial tube. This allows the patient to awaken without the upper airway obstruction and the coughing and gagging that often accompanies emergence from endotracial anesthesia. In so doing, evasive airways are avoided, the functional residual capacity is optimize, atelectasis is prevented and elimination of the anesthetic vapors is promoted. Accordingly, what is needed is a way of continuously supplying C-PAP to a patient recovering from general anesthesia: from the time the anesthesia is turned off in the operating room, during transport to the recovery room; and through the entire recovery phase until the patient is well awake.

SUMMARY OF THE INVENTION

It is the object of this invention to provide a method and apparatus that may comfortably be applied to the conscious patient prior to the induction of anesthesia to prevent airway obstruction and maintain oxygenation after the patient has become unconscious under the influence of anesthesia.

It is another object of this invention to enable a patient to adequately respire at surgical levels of anesthesia without an invasive airway and manual or mechanized ventilation.

It is another object of this invention to cost-effectively add air to the anesthetic gasses for reducing the risk of combustion in the surgical field when using cautery or laser devices.

It is another object of this invention to prevent leakage of the anesthesia to the operating room.

It is another object of this invention to more accurately monitor spontaneous respirations in a pressurized system.

It is another object of this invention to prevent an airflow generator from excessively pressurizing an anesthesia circuit.

It is another object of this invention to provide an airflow generator operable to generate a constant flow rate and allow the airway pressure to vary. Such a constant flow rate airflow generator would have several advantages in critical care settings. A constant rate of airflow would allow the reservoir bag of the anesthesia circuit to fluctuate in the usual manner, thereby establishing a simple and reliable monitor of respirations in critical care situations. Accordingly, adjustment of the rate of constant flow, may be used to establish a fluctuating positive pressure in the breathing circuit, always positive, but more positive on expiration and less positive on inspiration. Such a pattern would promote venous return to the heart by the bellows-like action of the "thoracic pump." Further, the constant flow would better allow capnographic monitoring of respirations, the monitoring of which is impeded by the excessive flows generated by C-PAP machines which restrict carbon dioxide from entering the breathing circuit. Accordingly, it follows that a greater volume of humidified expiratory air courses through the breathing circuit. This moisture can be captured by a "heat and moisture exchange" filter and used to humidify the inspiratory air delivered to the patient. Such a system would be of benefit to the OSA patient at home where the C-PAP machine is known to cause dry and sore throats.

It is another object of this invention to provide an airflow generator, for example, a portable or battery operated constant airflow generator, could be used to transport patients. After anesthesia, for example, the airflow generator could remain attached to the breathing circuit while the patient is being transported to the recovery room and, then, left in place while the patient is recovering. The advantages of this include: a) the positive pressure would optimize expansion of the patient's lungs during a time in which the patient typically hypoventilates; b) the positive pressure would continue to prevent obstruction and the triggering of laryngospasm which too often occurs during emergence from anesthesia; c) the augmented respiratory flows would facilitate the washing-out of anesthesia gases from the lungs; and d) air supplied to the lungs under positive pressure corrects hypoxia from the hypoventilation which can lead to "absorption atelectasis" and pneumonia if treated only by administering oxygen.

Not only would ambient air be cost-free and inexhaustible, but any desired level of oxygen enrichment could be achieved with the addition of only a small fraction of the oxygen used in conventional systems. Therefore, such an airflow generator would provide an economic advantage of the more costly oxygen delivery systems.

The constant-flow airflow generator could be used to add an exact amount of air to a conventional anesthesia system, thereby allowing a precise adjustment of the anesthesia gas vaporizer to deliver any desired end-concentration of anesthetic gas.

The constant-flow airflow generator could, itself, provide the carrier gas to an anesthesia vaporizer of the "draw-over" type and, thereby, eliminate the need for a standard anesthesia machine. Such a system, especially if combined with battery power and an oxygen concentrator, would eliminate the need for tanks of compressed gases and be relatively "free-standing" and more portable than existing systems.

It is another object of this invention to provide a device (adapter) which could convert a standard "C-PAP Machine" from continuous-pressure air delivery device to continuous-flow air delivery device. If, first, the C-PAP machine were to be set at a fixed pressure, then, the air out-put could be directed through a variable-resistance orifice to produce an adjustable fixed flow. Whereas a standard "C-PAP Machine" is designed to meet the high flow rates of inspiration by pumping more air to maintain a constant pressure, the adapter system would require that a reservoir bag be provided to meet the flow demands of inspiration. Nevertheless, in anesthesia and critical care breathing circuits, this can be used to advantage, as discussed previously.

It is another object of this invention to provide a reliable continuous breath-by-breath monitor of the breathing circuit and the patency of the upper airway of the patient. A stethoscope designed to fit in-line with the tubing of the breathing circuit would transmit the unique combined sounds of airflow through the circuit and upper airway of the patient. Such a stethoscope would give the earliest warning of impending airway obstruction and allow corrective action to be taken within a breath of discovery with immediate feedback as to the effectiveness of the remedy.

It is another object of this invention to provide a simple and inexpensive mechanical monitor of inspiratory flow.

It is another object of this invention to provide a system for continuously supplying C-PAP to a patient recovering from general anesthesia: from the time the anesthesia is turned off in the operating room; during transport to the recovery room; and through the entire recovery phase until the patient is well awake.

Upper airway obstruction caused by a drug-induced depression of the central nervous system is preventable by applying positive pressure through the nasopharynx while leaving the oral cavity open to ambient pressure. The pressure differential thus created, splints the soft tissues out of the airway with a natural pressure relief valve through the oral cavity. The maximum pressure obtainable is consistently sufficient to relieve the obstruction, but is less than the 20 centimeters of water that might send air to the stomach.

In accordance with one method of the present invention, nasal oxygen is applied to an awake patient through a sealed nasal connection. A conventional anesthesia administering apparatus, i.e., anesthesia circuit, that is unable to provide air to a patient may be modified to include an air supply. In any event, a conventional anesthesia administering apparatus can be modified in accordance with the present invention to provide a sealed nasal connection. Nasal oxygen may be applied as 100% oxygen, or a diluted form of oxygen by supplying air.

The sealed nasal connection may be provided by any device that may: be inserted into the nasal vestibule of the patient; provide a seal between the device and an inner surface of the nasal vestibule; and administer an amount of a gas into the nasal vestibule via the nasal vestibular portion, wherein the seal promotes airway pressure buildup that is sufficient to prevent obstruction of the airway during depression of at least a portion of the nervous system and prevents escape of the gas from between the nasal vestibule and the device. For example, the sealed nasal connection may be provided by a device having a nasal vestibular portion that is shaped as portions of the devices as disclosed in U.S. Pat. No. 5,533,506 to Wood, U.S. Pat. No. 4,702,832 to Tremble et al, U.S. Pat. No. 5,134,995 to Gruenke et al., U.S. patent application Ser. No. 09/430,038, the entire disclosures of which are incorporated herein by reference.

Unlike the airflow delivery device 108 discussed above with reference to FIG. 1, the sealed nasal connection of the present invention cannot include ventilation holes. In particular, the ventilation holes 112 of airflow delivery device 108 provide ventilation for $CO_2$ of the user during expiration. However, such vent holes would be counter-productive if included in the sealed nasal connection of the present invention. In particular, such vent holes would enable gas, that would otherwise have been forced into the airway of the patient to prevent airway obstruction, to escape. Accordingly, the ability for the sealed nasal connection of the present invention to prevent airway obstruction would be reduced.

Once nasal oxygen is administered to the awake patient, the patient is forced to breathe in through the nose and out through the mouth. The patient will do so fairly comfortably as long as the nasal oxygen flow rate is adjusted to comfort.

Anesthesia is then induced, either intravenously or inhalationally through the sealed nasal connection. Then, when anesthesia is induced and total relaxation of the pharyngeal muscles occurs, obstruction is prevented automatically as pressure within the anesthetic circuit builds to prop open the patient's airway. With the mouth left open to ambient pressure in the deeply sedated patient, a pressure gradient is established which allows the soft palate and tongue to be propped out of the pharyngeal airway while at the same time creating a low pressure seal of the soft palate to the tongue which remarkably releases somewhat between 8 and 20 cm of water pressure. There is, in effect, a pressure "pop-off" valve that prevents a pressure build-up which would force air into the stomach (20 cm of water is the reported threshold pressure).

Aspiration of gastric acid into the lungs may result in fatal pneumonitis, which is the classic nightmare of anesthesia practice. Over-inflation of the lungs with pharyngeal pressures in excess of 20 cm of water has been shown to blow air into the stomach. The resultant distension of the stomach with air under pressure has been known to cause regurgitation and subsequent aspiration of acid into the lungs. However, C-PAP under 20 cm of water has been shown to oppose the reflux of acid up the esophagus by increasing the intra-thoracic pressure above the intra-abdominal pressure. This serves to create a pressure gradient which opposes reflux under anesthesia.

The reflex apnea triggered by obstruction is prevented and the patient resumes spontaneous respirations after a few seconds of central apnea, which may occur as a consequence to the direct depression of the central nervous system by the anesthetic drug itself.

Deep levels of inhalational anesthesia can be achieved through spontaneous and unassisted respirations. Then, with the sealed nasal connection left in place, anesthesia and oxygenation can be sustained during, for example, a difficult intubation where ordinarily the removal of the oxygen mask would effectively remove adequate oxygenation from the patient. In theory, as long as 100% oxygen is provided at the level of the open vocal chords, even a patient who is not breathing will remain well-oxygenated and viable for nearly an hour. In particular, the patient will maintain adequate ventilation spontaneously when connected to the closed anesthesia circuit with the nasal oxygen flow rate adjusted to maintain a positive pressure sufficient to prevent obstruction. In other words, the patient is enabled to respire adequately, at surgical levels of anesthesia, totally free of an invasive airway and manual or mechanized ventilation.

In accordance with a method of the present invention, a more strict monitoring method is required to detect early partial airway obstruction. For example, a more sensitive anesthetic circuit pressure gauge and a supra-sternal stethoscope may be used. In particular, a conventional pressure gauge in a conventional anesthesia circuit is scaled to approximately 160 units over the full circumference of its face (1 unit=1 centimeter of water pressure). On the contrary, a pressure gauge in accordance with the present invention would be more sensitive and have a scale of 40 units over the same circumference. The fluctuations of the needle of the gauge would, therefore, be amplified by a factor of four making it a sensitive monitor of the alternating pressures of the respiratory cycle. Further, as stated above, because pressures in excess of 20 cm of water has been shown to blow air into the stomach, the pressure gauge must be able to measure at least 20 cm of water. More importantly, the pressure gauge in accordance with the present invention should display the detected pressure at a precision that would readily communicate the difference between a inspiration and an expiration of the patient.

The airway pressure used under anesthesia, in accordance with the present invention, is not C-PAP as applied in the treatment of obstructive sleep apnea. The airflow rate of a C-PAP generator automatically increases and decreases to maintain a constant positive airway pressure. On the contrary, in accordance with the present invention, a gas flow rate to the patient is constant and is manually adjusted to a level that produces a positive pressure, which prevents obstruction. An apparatus in accordance with the present invention is capable of providing a supplemental gas, such as for example oxygen or air, at a constant, adjustable, flow rate to the patient. Using a method in accordance with the present invention, the supplemental gas is supplied in an amount such that there is a constant gas flow rate and there is always a positive pressure, but the magnitude of the pressure varies with respiration. This approach, i.e., using a constant gas flow rate, causes airway pressure to be higher on expiration than on inspiration. The varying pressure and constant gas flow rate provided by the method and apparatus of the present invention is advantageous over conventional C-PAP because the constant gas flow rate and varying pressure promotes a better venous return to the heart. The varying pressure accompanied with the constant gas flow rate in accordance with the present invention is termed alternating positive airway pressure.

The alternating positive airway pressure generated by the system in accordance with the present invention has further beneficial effects keeps the lungs expanded to a more optimal functional residual capacity, thereby increasing the oxygen reserves within the lungs, which in turn prevents atelectasis from collapse of the alveoli. Further, when air is combined with oxygen, the alternating positive airway pressure generated by the system in accordance with the present invention prevents atelectasis from oxygen absorption. Still further, the alternating positive airway pressure creates a positive intra-thoracic pressure, which serves to reverse any existing tendency towards reflux of gastric contents up the esophagus, which might lead to aspiration into the lungs.

The system and method of use thereof in accordance with the present invention has still further beneficial effects. When inhalational anesthesia is used, the carbon dioxide can be sampled from the scavenger mask to monitor respirations and to assure that the scavenger is working to remove exhaled gas. Depth of anesthesia is rapidly increased by increasing flow rates to the nose so that no exhaled gas comes back into the anesthesia circuit, but rather, is forced out through the mouth. Denitrogenation and oxygenation is facilitated along with the increased flow rate of higher anesthetic gas concentrations into the lungs. Similarly, at the end of the procedure, anesthetic gasses are rapidly eliminated by a unidirectional high flow of oxygen and/or air into the anesthetic circuit. In deep sedation (e.g. MAC, "MONITORED ANESTHESIA CARE"), precise concentrations of oxygen can be monitored and administered to the patient without escaping into the surgical field thereby reducing the fire hazard that accompanies the routine practice of bringing oxygen into the proximity of cautery and laser devices through a standard oxygen cannula.

Many conventional anesthetic delivery machines or facilities do not have the capacity for adding controlled, pressurized air to the anesthetic gasses. More importantly, no conventional anesthetic delivery machines or facilities have the capacity for adding controlled, pressurized air or pure oxygen to the anesthetic gasses such that the total gas flow rate administered to the patient is sufficient to prevent obstruction of the airway during depression of the portion of the nervous system.

A device in accordance with the present invention includes a constant gas flow rate generator that is adaptable for use with a conventional anesthetic delivery machine. The constant gas flow rate generator will add a gas, such as oxygen or air, at a constant gas flow rate of a level that produces a positive pressure that is sufficient to prevent airway obstruction. Furthermore, a constant gas flow rate generator in accordance with the present invention may include an adjustment device, such as an automatic or manual adjustment device, for adjusting the constant gas flow rate. An exemplary embodiment of an automatic adjustment device includes a gas flow rate meter that is operably connected to a gas flow valve. In particular, in operation of the exemplary embodiment of an automatic adjustment device, the gas flow rate may be set by the user. The gas flow rate may be subsequently monitored by the gas flow rate meter, the output of which controls the gas flow valve to open/close in the amounts required to maintain the gas flow rate set by the user. An exemplary embodiment of a manual adjustment device includes a gas flow rate meter that displays a gas flow rate to a user and a gas flow valve. In particular, in operation of the exemplary embodiment of a manual adjustment device, the gas flow rate as displayed by the gas flow rate meter is monitored by the user. The user will then operate the gas flow valve to open/close in the amounts required to maintain the gas flow rate desired by the user.

A gas delivery apparatus according to the present invention includes a nasal insert having a gas passage therein for insertion into the nose, such as for example a device disclosed in U.S. application Ser. No. 09/430,038, which is capable of forming a seal with the inner surface of the nasal vestibule. Bendable tubing is included in the apparatus. The bendable tubing has a proximal portion connected to the nasal vestibular portion so as to be in gas communication with the gas passage of the nasal vestibular portion. The nasal vestibular portion flares outwardly with respect to the gas passage therein.

The nasal vestibular portion may comprise a superior pole for engaging the apex of a nasal vestibule. Further, an inferior pole of the nasal vestibular portion may be provided to engage an inferior nostril rim of the nasal vestibule. The superior pole may be elongated and rounded, and the inferior pole may comprise an angled wedged shape. Thus, the superior pole, lodged in the apex of the nasal vestibule, may be shaped so as to help to direct the inferior pole against the inner surfaces of the nose to push the surfaces outward, thereby sealing.

The nasal vestibular portion may comprise a flexible material. In this case, a thin flap can be provided around the perimeter of the nasal vestibular portion for providing further sealing with the nasal interior.

A second nasal vestibular portion may be provided to connect with the second nostril of a patient. The second nasal vestibular portion also flares outwardly with respect to the connection part. A head strap and/or an ear hook may be connected to the tubing to hold the tubing on the head of the patient.

A nasal plug can also be adapted to close one nostril when only one nasal airway is supplied with gas. The nasal plug may be similar to the nasal airway which comprises a connection part and a nasal vestibular portion, but in this case would have its gas passage blocked, for example by a cap. Alternatively, the cap could include a small opening to receive an oxygen tube to provide oxygen to the nostril.

In general, the present invention provides a gas administering method for administering gas to an airway of a patient having a nasal vestibule. The gas administering method is for use with a gas administering apparatus comprising a gas source that is operable to provide gas and a nasal vestibular portion arranged so as to receive the gas from the gas source. Further, the nasal vestibular portion is capable of releasing the gas into the nasal vestibule. The method comprises inserting the nasal vestibular portion into the nasal vestibule, forming a seal between the nasal vestibular portion and an inner surface of the nasal vestibule, administering an amount of a gas from the gas source at a constant flow rate into the nasal vestibule via the nasal vestibular portion, and administering an anesthetic to the patient. The anesthetic induces depression of a portion of the nervous system of the patient. Furthermore, the seal causes airway pressure buildup that is sufficient to prevent obstruction of the airway during depression of the portion of the nervous system and prevents escape of the gas from between the nasal vestibule and the nasal vestibular portion.

In one embodiment of the present invention, the gas administering method further comprises administering oxygen into the nasal vestibule via the nasal vestibular portion, prior to the administering of the anesthetic. More particularly, the oxygen is provided from a source of gas that is 100% oxygen. Alternatively, the oxygen is provided from a source of gas that is a mixture of oxygen and nitrogen.

In another embodiment of the present invention, the administering of an amount of a gas comprises administering 100% oxygen.

In another embodiment of the present invention, the administering of an amount of a gas comprises administering air.

In another embodiment of the present invention, the gas administering method further comprises detecting for an airway obstruction. More particularly, the detecting for an airway obstruction comprises placing a stethoscope over the trachea at the supra-sternal notch.

In another embodiment of the present invention, the gas administering method further comprises monitoring respiratory effort. More particularly, the monitoring respiratory effort is performed via an electrocardiogram monitor operating in a thoracic impedance mode.

In another embodiment of the present invention, the gas administering method further comprises retrieving anesthetic that is expired from the mouth of the patient. More particularly, the retrieving waist anesthetic comprises placing an anesthetic retrieving device over the face of the patient.

In general, the present invention further provides a gas administering method for administering a gas to an airway of a patient having a nasal vestibule. This method is for use with a gas administering apparatus comprising a gas source that is operable to provide gas at a constant flow rate and a nasal vestibular portion having a shape such that the nasal vestibular portion provides an outward force on an inner surface of the nasal vestibule, due to elasticity of the nasal vestibule, for retaining the nasal vestibular portion in the nasal vestibule. Further, the nasal vestibular portion is arranged so as to receive the gas from the gas source. Still further, the nasal vestibular portion is capable of releasing the gas. The method comprises inserting the nasal vestibular portion into the nasal vestibule thereby forming a seal between the nasal vestibular portion and an inner surface of the nasal vestibule, administering an amount of a gas at a constant flow rate into the nasal vestibule via the nasal vestibular portion, and administering an anesthetic to the patient. The anesthetic induces depression of a portion of the nervous system of the patient. Finally, the seal causes airway pressure buildup that is sufficient to prevent obstruction of the airway while under sedation and prevents escape of the gas between the nasal vestibule and the nasal vestibular portion.

In general, the present invention still further provides a gas administering method for administering gas to an airway of a patient having a nasal vestibule. This method is for use with an anesthetic administering apparatus comprising an anesthetic gas source that is operable to provide an anesthetic. The method comprises fastening a nasal vestibular portion to the anesthetic administering apparatus so as to receive the anesthetic gas from the anesthetic gas source (the nasal vestibular portion is capable of releasing the anesthetic gas into the nasal vestibule), inserting the nasal vestibular portion into the nasal vestibule, forming a seal between the nasal vestibular portion and an inner surface of the nasal vestibule, fastening a supplemental gas source to the anesthetic administering apparatus (the supplemental gas source is operable to provide a supplemental gas at a constant flow rate to the anesthetic administering apparatus) administering an amount of the supplemental gas from the supplemental gas source at a constant flow rate into the nasal vestibule, from the anesthetic administering apparatus, via the nasal vestibular portion, and administering an amount of the anesthetic gas from the anesthetic gas source into the nasal vestibule, from the anesthetic administering apparatus, via the nasal vestibular portion. The anesthetic gas comprises an amount of anesthetic sufficient to induce depression of at least a portion of the nervous system of the patient. Finally, the seal promotes airway pressure buildup that is sufficient to prevent obstruction of the airway during depression of the at least a portion of the nervous system and prevents escape of the anesthetic gas or the primary gas from between the nasal vestibule and the nasal vestibular portion.

In general, the present invention still further provides a gas administering system for administering gas to an airway of a patient having a nasal vestibule. The gas administering system comprises a gas source that is operable to provide gas at a constant flow rate and a nasal vestibular portion arranged so as to receive the gas from the gas source. The nasal vestibular portion is capable of releasing the gas into the nasal vestibule and is shaped to form a seal between the nasal vestibular portion and an inner surface of the nasal vestibule such that the gas released into the nasal vestibule causes airway pressure buildup sufficient to prevent obstruction of the airway during depression of at least a portion of the nervous system. Further, the seal prevents escape of the gas from between the nasal vestibule and the nasal vestibular portion.

In one embodiment of the present invention, the gas source comprises a primary gas source for providing a primary gas and a supplemental gas source that is operable to provide a supplemental gas. More particularly, the primary gas source may comprise an anesthetic gas providing device. Further, the primary gas source may comprise an oxygen providing device. Still further, the supplemental gas source may comprise an air providing device having a flow rate adjustment mechanism.

In another embodiment of the present invention, the gas administering system further comprises a respiration monitor.

In another embodiment of the present invention, the gas administering system further comprises a scavenging device for scavenging gas expired from the mouth of the patient.

In another embodiment of the present invention, the gas administering system further comprises a gas flow meter for measuring the gas flow rate of the gas provided by the gas source.

In another embodiment of the present invention, the natural curvature of gas flow tubing is utilized to enhance performance of a nasal vestibular device.

In another embodiment of the present invention, a nasal vestibular device includes rounded portions that can be trimmed and that include raised marks to provide a simple measuring system for incrementally trimming the rounded portions to accurately fit increasingly smaller nasal vestibules.

In another embodiment of the present invention, a nasal vestibular device includes an open portion to permit venting of expired $CO_2$ gas during expiration wherein the open portion includes a raised line shaped to receive a plug cap, in the event that venting is not required.

In another embodiment of the present invention, a nasal vestibular device includes two nasal vestibular portions in communication with one another via an inter-connecting tube that may be cut to yield a nasal vestibular device having a single nasal vestibular portion to be used in a single nasal vestibule.

In another embodiment of the present invention, a connector may be used to connect gas flow tubing together, wherein the connector includes a plurality of angled ridges on the inside perimeter thereof that are shaped to permit insertion of the tubing into the connector in a first direction and to inhibit the tubing from being pulled out of the connector in a second direction.

In another embodiment of the present invention, a wireless electronic stethoscope transmitter is used with a breathing circuit stethoscope in accordance with the present invention.

In another embodiment of the present invention, spirometers are used with a breathing circuit to measure the volume of the exhaled gas.

In another embodiment of the present invention, a home treatment system includes a nasal vestibular device, a heat and moisture exchanger for conserving heat and moisture, a vent, tubing and a C-PAP machine.

In another embodiment of the present invention, a transport and auxiliary power assembly permits convenient and continuous operation of a C-PAP machine while being transported from the operating room to the recovery room.

Additional advantages of the present invention will become apparent to those skilled in the art from the following detailed description of the preferred embodiments of the present invention. The invention itself, together with further objects and advantages, can be better understood by reference to the following detailed description and the accompanying drawings.

BRIEF DESCRIPTION OF THE DRAWINGS

The accompanying drawings, which are incorporated in and form a part of the specification, illustrate embodiments of the present invention and, together with the description, serve to explain the principles of the invention.

FIG. 1 illustrates a conventional system for treating sleep induced apnea by providing a continuous positive airway pressure through the nose.

FIG. 2 generally illustrates a preferred embodiment of a gas delivery apparatus according to the present invention.

FIG. 6 illustrates a gas delivery system in accordance with an exemplary embodiment of the present invention.

FIG. 8 is a flow chart detailing an exemplary method of operation of gas delivery system as illustrated in FIG. 7.

FIG. 9A is an exemplary subroutine for a step of increasing oxygen in the flow chart as illustrated in FIG. 8; FIG. 9B is another exemplary subroutine for a step of increasing oxygen in the flow chart as illustrated in FIG. 8.

FIG. 10A is an exemplary subroutine for a step of decreasing oxygen in the flow chart as illustrated in FIG. 8;

FIG. 10B is another exemplary subroutine for a step of decreasing oxygen in the flow chart as illustrated in FIG. 8.

FIG. 11A is an exemplary subroutine for a step of administering anesthetic in the flow chart as illustrated in FIG. 8; FIG. 11B is another exemplary subroutine for a step of administering anesthetic in the flow chart as illustrated in FIG. 8.

FIG. 12A is an exemplary subroutine for a step of increasing the amount of administered anesthetic in the flow chart as illustrated in FIG. 8; FIG. 12B is another exemplary subroutine for a step of increasing the amount of administered anesthetic in the flow chart as illustrated in FIG. 8.

FIG. 13A is an exemplary subroutine for a step of decreasing the amount of administered anesthetic in the flow chart as illustrated in FIG. 8; FIG. 13B is another exemplary subroutine for a step of decreasing the amount of administered anesthetic in the flow chart as illustrated in FIG. 8.

FIG. 19 illustrates another exemplary embodiment of a nasal vestibular portion that may be used with the gas delivery device in accordance with the present invention.

FIG. 20 illustrates another exemplary embodiment of a nasal vestibular portion that may be used with the gas delivery device in accordance with the present invention.

FIG. 21 illustrates another exemplary embodiment of a nasal vestibular portion that may be used with the gas delivery device in accordance with the present invention.

FIG. 23 illustrates the application of the nasal vestibular portion illustrated in FIG. 22.

FIGS. 24A–24D illustrate exemplary embodiments of connector portions to be used with nasal vestibular portions in accordance with the present invention.

FIG. 25A illustrates an exemplary embodiment of a connector portion of a device that may be used with a gas delivery device in accordance with the present invention; FIG. 25B illustrates the connector of FIG. 25A combined with another exemplary embodiment of nasal vestibular portions may be used with the gas delivery device in accordance with the present invention; FIG. 25C is a left and right hand view of the combination of the connector portion and the nasal vestibular portions of FIG. 25B.

FIG. 26 illustrates the application of the combination of the connector portion and the nasal vestibular portions of FIG. 25B.

FIG. 27 illustrates a gas delivery tube and a plug to be used in accordance with the present invention.

FIG. 28 illustrates a gas delivery tube and a cap to be used in accordance with the present invention.

FIGS. 47A and 47B illustrates exemplary embodiments of spirometers for use with a breathing circuit, in accordance with the present invention.

FIG. 48 illustrates a system for use in the home treatment of a patient with obstructive sleep apnea, in accordance with the present invention.

FIG. 49 illustrates a mesh filter for use with a heat moisture exchanger, in accordance with the present invention.

FIG. 50 illustrates a filter-plate for use with a heat moisture exchanger, in accordance with the present invention.

Figure 3A:
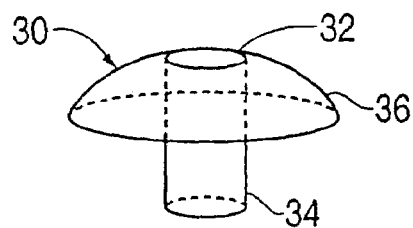
FIG. 3A illustrates an exemplary embodiment of a nasal vestibular portion that may be used with the gas delivery device in accordance with the present invention.

In the following description, for purposes of explanation, numerous specific details are set forth in order to provide a more thorough understanding of the present invention. It will be apparent, however, to one skilled in the art that the present invention may be practiced without the specific details.

DETAILED DESCRIPTION OF THE PREFERRED EMBODIMENTS

The following is a description of an exemplary method of and apparatus for enabling a patient to adequately respire at surgical levels of anesthesia without an invasive airway and manual or mechanized ventilation in accordance with the present invention.

During a pre-operative interview the patient is asked to confirm that he can breathe in and out through his nose.

The patient is then taken into the operating room and assisted in voluntarily positioning himself to comfort as appropriate through the anesthesia plan for facilitating the surgical intervention. Supine is the usual starting position for positions requiring intubation of the trachea. However, for superficial procedures in which the patient can be allowed to breath spontaneously, the patient can often be positioned awake and to comfort in the prone or lateral positions before induction of anesthesia. The airway, more often than not, is more easily maintained in these positions than in the supine position because of the lessened effects of gravity on the soft tissues (tongue and soft palate) that tend to collapse the airway. The awake patient will maintain a patent airway in any position, but the airway tends to collapse with deep sedation and general anesthesia. An invasive airway device can be traumatic and, in the case of an endotracheal tube, may cause more physiological disturbance than the surgery itself, if the anesthesia is not profound. On the other hand, a major cause of morbidity and mortality in anesthesia is related to the steps taken to control the patient's airway and to render it unreactive to the powerful stimulus of an endotracheal tube. For example, it has been reported more than once, that the patient has been paralyzed to facilitate intubation only to discover that the tube cannot be placed and the patient cannot be manually ventilated. The prudent anesthetist takes care not to impede the patient's own respiratory function without a well-considered reason and without thorough preparation. By using the method and apparatus in accordance with the present invention, the apparatus is inserted in the awake state, wherein a judgement can be usually made beforehand about the adequacy of the patient's respirations under deep sedation.

After the patient is appropriately positioned, conventional monitors may be attached to monitor the patient's vital signs, for example blood pressure, pulse rate, temperature, respiration rate, etc. A nasal insert device in accordance with the present invention is then snugly fitted into the nasal vestibule of the nose where the tissues are tougher and less sensitive than the mucosal lining of the turbinates and pharynx. Accordingly, an airtight seal is established fairly comfortably in the awake patient. This method of administering gas with the nasal insert device is less painful and traumatic to the patient than the conventional intubational method which uses an endotracheal tube. Further, a conventional nasal-pharyngeal airway is too long to be comfortably inserted into the deeper, more sensitive areas of the nose and nasopharynx.

The device of the present invention is then attached through standard connections to a closed anesthesia circuit, i.e., the pressure relief valve of the circuit is closed, and the flow rate of 100% oxygen is adjusted to the patient's comfort.

As the monitors are attached and preparation is made for induction of anesthesia, the awake patient is comfortably forced to breathe in through the nose and out through the mouth. The inhaled concentration of oxygen approaches 100% and nitrogen exhaled through the lungs is more effectively washed out, i.e. the period of denitrogenation, by the continuous flow of oxygen out through the mouth. Accordingly, the lungs are rapidly filled with oxygen and reserves of oxygen within the functional residual cavity of the lungs approaches a factor of ten increase, increasing dramatically the margin of safety as the critical induction period is approached. This is accomplished, by way of the present invention, in the comfortable, cooperative patient.

As preparation for induction of anesthesia approaches completion, the pulse oximeter usually approaches 100% oxygen saturation of the hemoglobin. The patient is then asked to take a breath through his nose. Nasal patency is confirmed by the deflation of a reservoir bag of the anesthesia circuit. At this point, the patient may be rapidly induced to deep sleep by a bolus of an induction drug, e.g. propofol. The airway pressure of the anesthesia circuit is seen to rise from zero to a positive value as determined by adjustment of the oxygen in-flow of the circuit. This pressure rise occurs as the soft tissues of the pharynx collapse into the airway and as the pressure generated through the nose stints up the soft palate against the base of the tongue to create a sealed pharyngeal passage pressurized somewhere between 5 and 20 cm of water pressure. This seal tends to release excess pressure before 20 cm of water pressure is achieved. As this is the threshold pressure in the pharynx beyond which gas is forced into the stomach, distension of the stomach with the attendant risk of reflux of gastric contents is naturally avoided.

The patient may become apneic at first, but soon spontaneous respirations resume. As the spontaneous respirations resume, the pressure gauge of a system in accordance with the present invention will rise and fall with inspiration and expiration.

At this point several options are available:

(A) If deep sedation-total intravenous anesthesia (TIVA) is to be maintained, then the patient may be allowed to breathe spontaneously with a system in accordance with the present invention that is pressured sufficiently by a constant gas flow rate so as to prevent airway obstruction. Detection of partial airway obstruction is best detected by fixed-placement of a stethoscope over the trachea at the suprasternal notch. In addition, respiratory effort can be monitored by thoracic impedance mode of the electrocardiogram monitor.

(B) If general inhalation anesthesia is planned, then a scavenging system may be established by placing the standard anesthesia face mask over the nasal insert and its connections and then connecting the mask by standard corrugating tubing to the scavenger port of the anesthesia machine.

(C) If intubation is required, the nasal insert and its connection to the anesthesia circuit can be left in place while the scavenging mask is removed. This constant gas flow through the nose floods the pharynx with oxygen and the gas anesthetic to maintain oxygenation and anesthetic depth during even a prolonged intubation procedure. If at this point, the patient were to be paralyzed with a muscle relaxant and rendered totally apneic, oxygenation would still be potentially satisfactory for periods of time in excess of 20 minutes (without manual ventilation) by the process of "mass movement" of 100% oxygen from the pharynx into the vacuum in the lungs created by absorption of oxygen from the lungs into the blood. Thus, the method in accordance with the present invention routinely adds a large method of safety even for the unexpected difficult airway, which can be so disastrous to the patient.

FIG. 2 generally illustrates an exemplary embodiment of a gas delivery apparatus according to the present invention. As illustrated in FIG. 2, the gas delivery apparatus 202 includes two branches of tubing 206 that provide gas to a gas delivery device 208. Gas delivery device 208 includes two nasal vestibular portions 210 and 212 that are inserted into the nasal vestibules 214 of the patient 204. A scavenging device 216 may be used in conjunction with the gas delivery apparatus, and will be described in greater detail below. The gas delivery apparatus 202 further includes a gas input port 218 that receives gas from a gas source.

Gas delivery device 208 differs from airflow delivery device 108 of FIG. 1 in that gas delivery device 208 does not have ventilation holes.

Vestibular portions 210 and 212 can be any shape that may: be inserted into the nasal vestibule of the patient; provide a seal between the gas delivery device 208 and an inner surface of the nasal vestibule; and administer an amount of a gas into the nasal vestibule via the nasal vestibular portion, wherein the seal promotes airway pressure buildup that is sufficient to prevent obstruction of the airway during depression of the portion of the nervous system and prevents escape of the gas from between the nasal vestibule and the gas delivery device 208.

Many other exemplary embodiments of a nasal vestibular portions will now be discussed. A common general design feature of the exemplary embodiments of the nasal vestibular portion is that each one may be insertable into the nose of an awake patient with a minimum of discomfort. In effect, each embodiment of the nasal vestibular portion may be confined to the relatively insensitive and resilient tissues of the nasal vestibule. Another common general design feature of the exemplary embodiments of the nasal vestibular portion is that each embodiment may seal with a nasal vestibule of the patient sufficient to achiever airway pressure of up to 20 centimeters of water with gas flow rates no greater than 20 liters/minute. Yet another design feature is that each exemplary embodiment may be self-retaining within the nasal vestibule of the patient. That is to say, each may be capable of functioning without straps or earhooks to hold it in place. In effect, the design may incorporate the following features: a) a superior pole insertable into the relatively deep superior recess of the nasal vestibule (i.e., the ventro-medial recess contained within the nasal tip); b) an interior pole designed to hold the rim of the shallow inferior recess of the nasal vestibule (i.e., dorso-lateral recess contained within the lateral flare of the base of the nose); c) rigidity in the longitudinal axis of the device which causes it to be fixed into the nasal vestibule between the retaining wall of the superior recess and the retaining rim of the inferior recess; d) lateral walls of the device which may be solid or flare out from a central spine with lateral compliance varying from zero to very compliant with the lateral and medial surfaces of the nasal vestibule.

Figure 29:
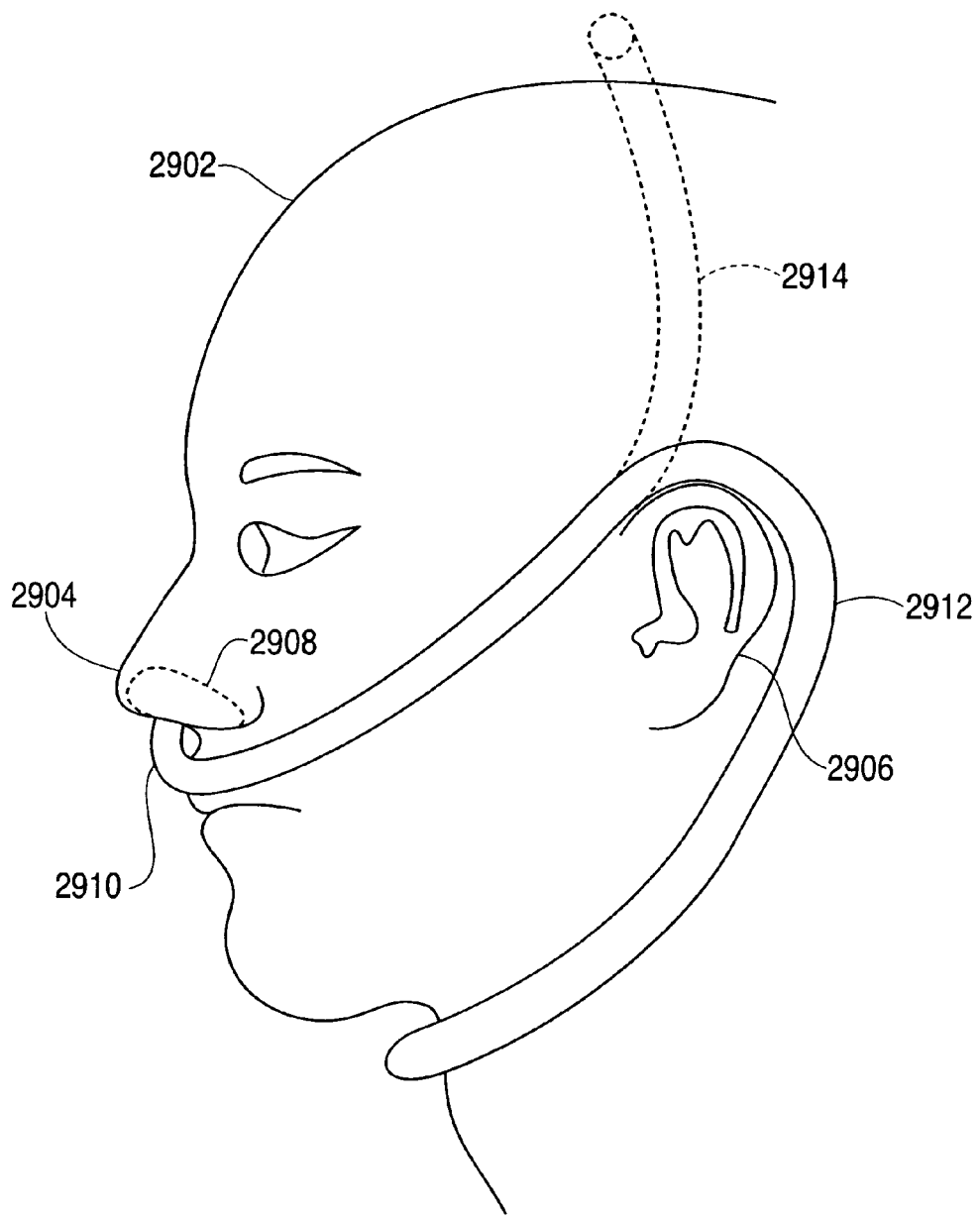
FIG. 29 illustrates applications of a gas delivery tube and a nasal vestibular device in accordance with the present invention.

Because of the self-retaining qualities of the nasal vestibular portions in accordance with the present invention, additional straps are not required to retain the gas delivery systems in the nose of the patient. Accordingly, as illustrated in the solid lines of FIG. 29, the gas delivery tubes 2912 may be draped over the ears 2906 of the patient 2902. Further, as illustrated in the dotted lines of FIG. 29, the self-retaining nasal vestibular portions 2908 additionally permit the gas delivery tubes 2912 to be draped over the head of the patient 2902.

Furthermore, the curvature of the gas delivery tubes may be exploited when used in conjunction with the self-retaining nasal vestibular portions in accordance with the present invention. For example, the curvature may be result of a "natural" curvature of the gas delivery tubes that is produced as a result of the coiling of the tubing during the manufacture. Further, the curvature may result from an explicitly designed self-sustaining curvature.

Figure 39:
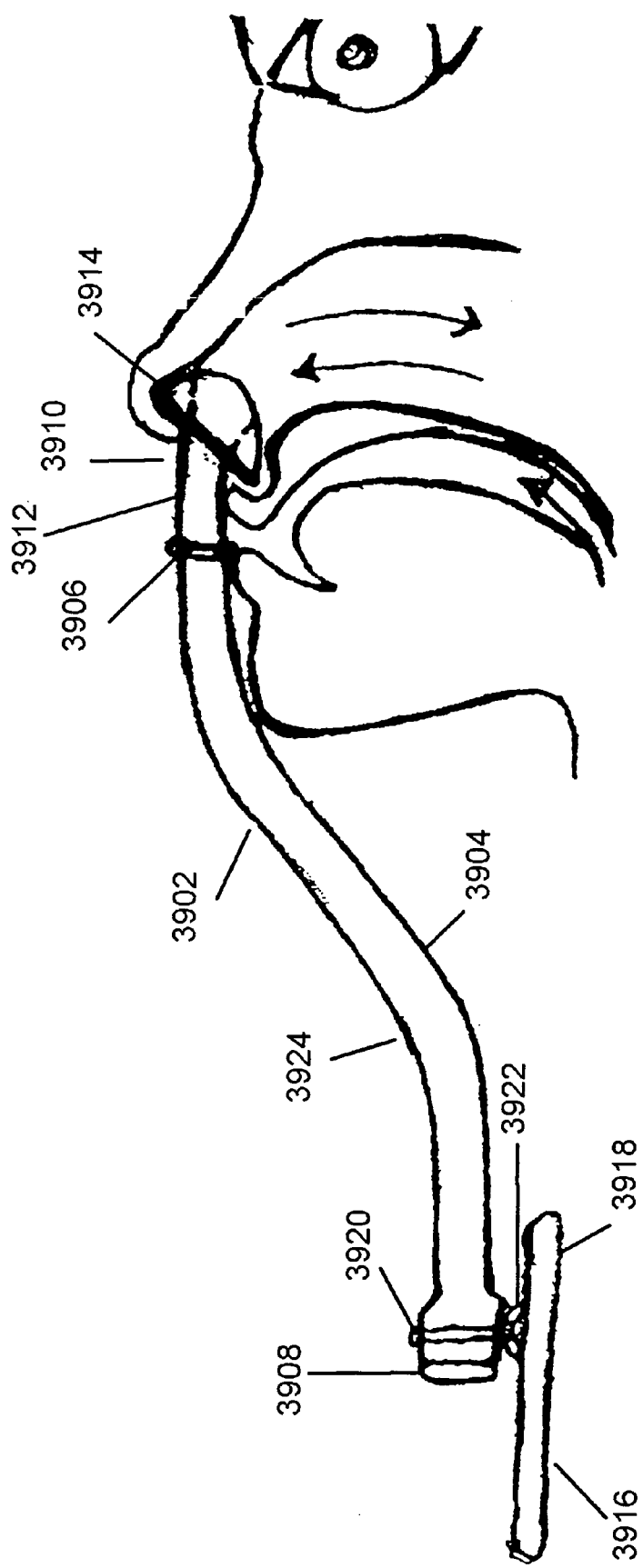
FIG. 39 illustrates an exemplary embodiment of a gas delivery tube that may be used with a self-retaining nasal vestibular device, in accordance with the present invention.

FIG. 39 and FIGS. 40A–40C illustrate exemplary embodiments of gas delivery tubes that may be used with a self-retaining nasal vestibular device in accordance with the present invention. As illustrated in FIG. 39, the gas delivery tube 3902 comprises a main portion 3904, an end portion 3906 and an end portion 3908. Each of end portion 3906 and end portion 3908 are illustrated as female connector portions. However, in further exemplary embodiments, either one of end portions 3906 and 3908 may be constructed as a male connecting end portion. End portion 3906 is adapted to connect to nasal vestibular device 3910 that includes a flow tube portion 3912 and nasal vestibular portion(s) 3914 to be inserted into the nasal vestibule of the patient. End portion 3908 is adapted to be connected to tubing of a breathing circuit. Further, as described more in detail below with respect to FIGS. 32 and 33, end portion 3908 may be attached, via an attachment device 3920, to a launching pad 3916 having a base 3918 and an attaching portion 3922.

The curvature of main portion 3904 is arranged in a manner illustrated in FIG. 39 in order to help hold the nasal vestibular device 3910 in place. If the curvature of main portion 3904 results from the coiling of the tubing during the manufacturing thereof, then the arrangement as illustrated in FIG. 39 may be accomplished by slightly twisting end portion 3908 relative to end portion 3906, prior to connecting the end portion 3908 to the tubing of the breathing circuit and prior to connecting end portion 3906 to nasal vestibular device 3910. Alternatively, if the curvature of main portion 3904 results from an explicitly designed self-sustaining curvature, then no twisting of end portion 3908 would be required to achieve the arrangement illustrated in FIG. 39. With the concave surface 3924 of tubing 3904 oriented away from the patient, the tubing uses the chin of the patient as a fulcrum to lever the nasal vestibular device 3910 up and into the nasal vestibule. If the tubing is angled in an opposite direction, the nasal vestibular device 3910 tends to dislodge from the nasal vestibule.

Figure 40A:
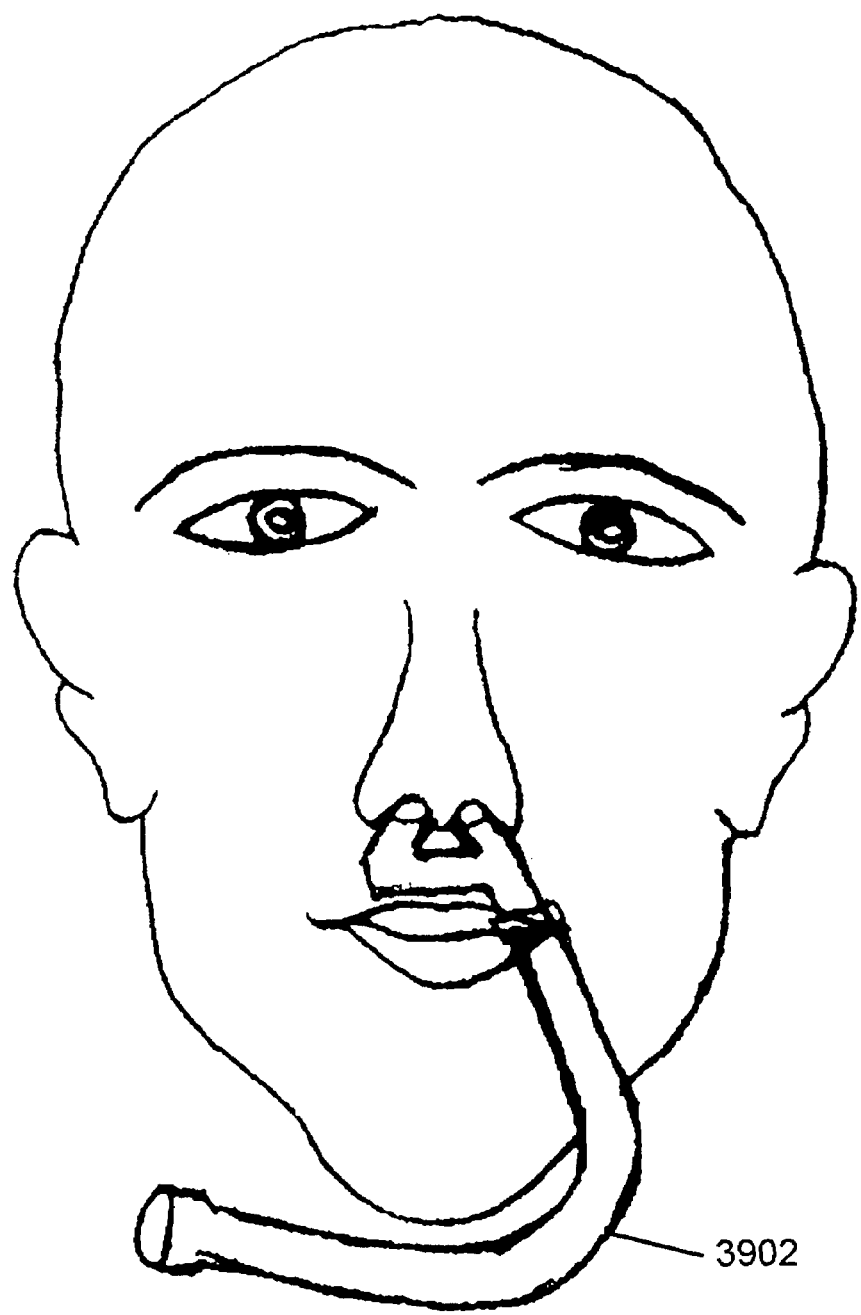
FIGS. 40A–40C illustrate further exemplary embodiments of a gas delivery tube that may be used with a self-retaining nasal vestibular device, in accordance with the present invention.
Figure 40B:
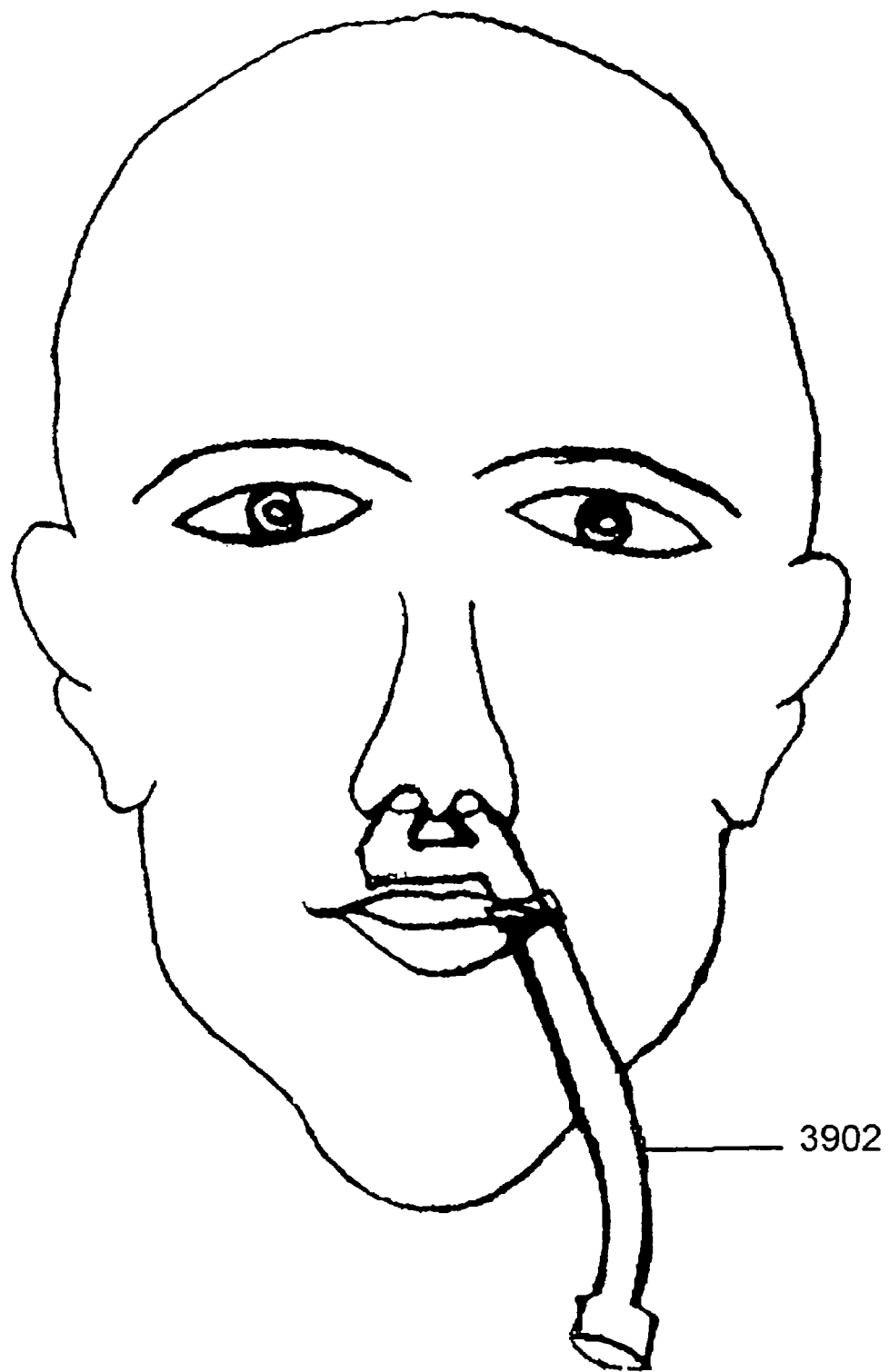
Figure 40C:
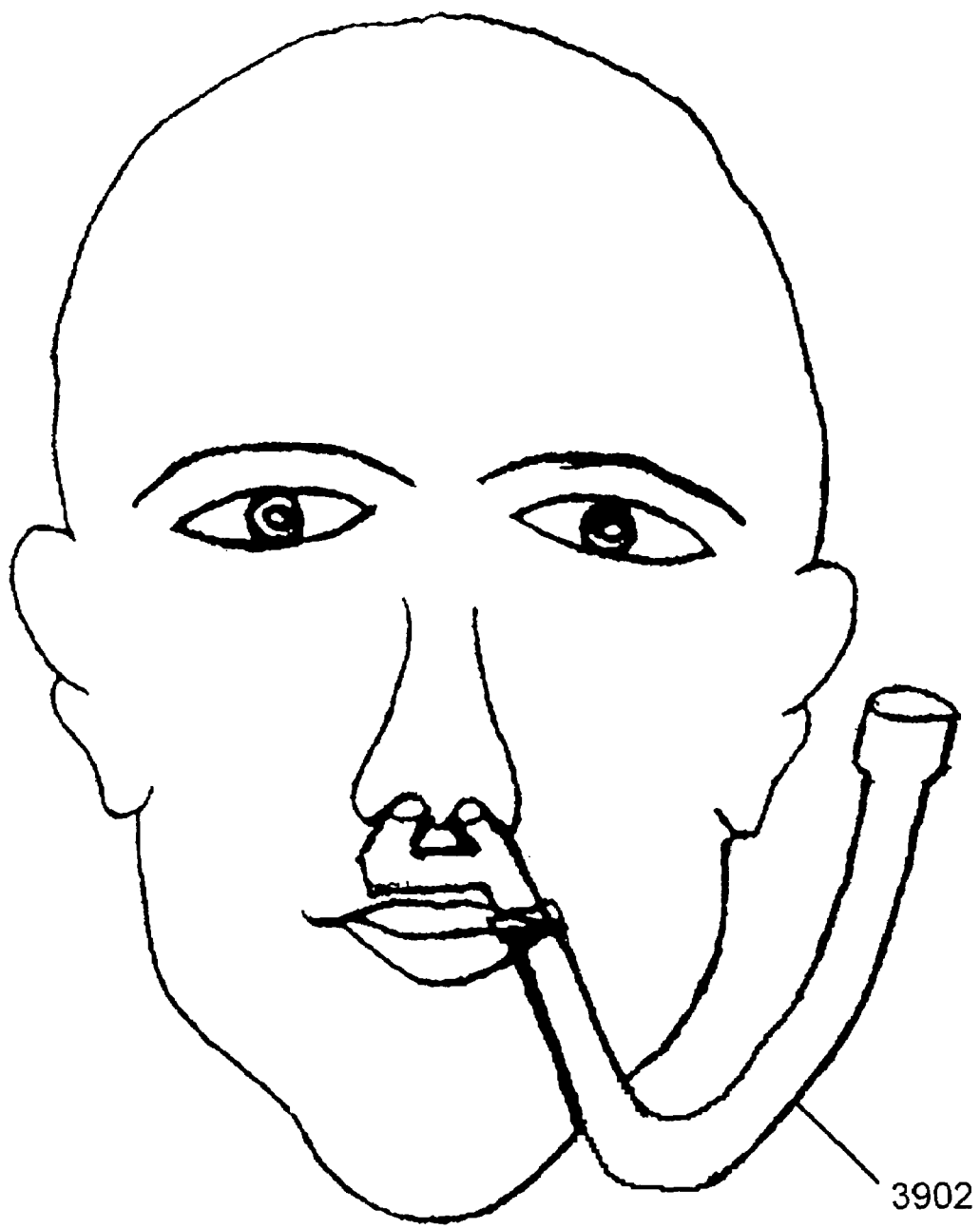

FIGS. 40A–40C illustrate applications of three different curvatures of gas delivery tube 3902.

With the convex surface of gas delivery tube 3902 being located, for example, clockwise to about 45 degree position in connection with the nasal vestibular device, gas delivery tube 3902 can be looped around the chin to stabilize the nasal vestibular device without twisting the nasal vestibular device in the nose. This application is illustrated in FIG. 40A.

As illustrated FIG. 40B, curvature of gas delivery tube 3902 is arranged to be generally downward away from the head of the patient for use in head and neck surgical procedures.

With the convex surface of gas delivery tube 3902 being rotated, for example counter-clockwise to about 315 degree position in connection with the nasal vestibular device, gas delivery tube 3902 can be bought up to the left side of the head without twisting the nasal vestibular device in the nasal vestibule. This application is illustrated in FIG. 40C (and FIG. 29).

As discussed above, the curvature of the tubing, properly oriented, greatly facilitates the self-retaining characteristic of the nasal vestibular device. Accordingly, the nasal vestibular device will not require strap hooks, etc., to hold it in place. This self-retaining characteristic is, perhaps, the quality which most distinguishes the nasal vestibular device from conventional nasal inserts.

Figure 45:
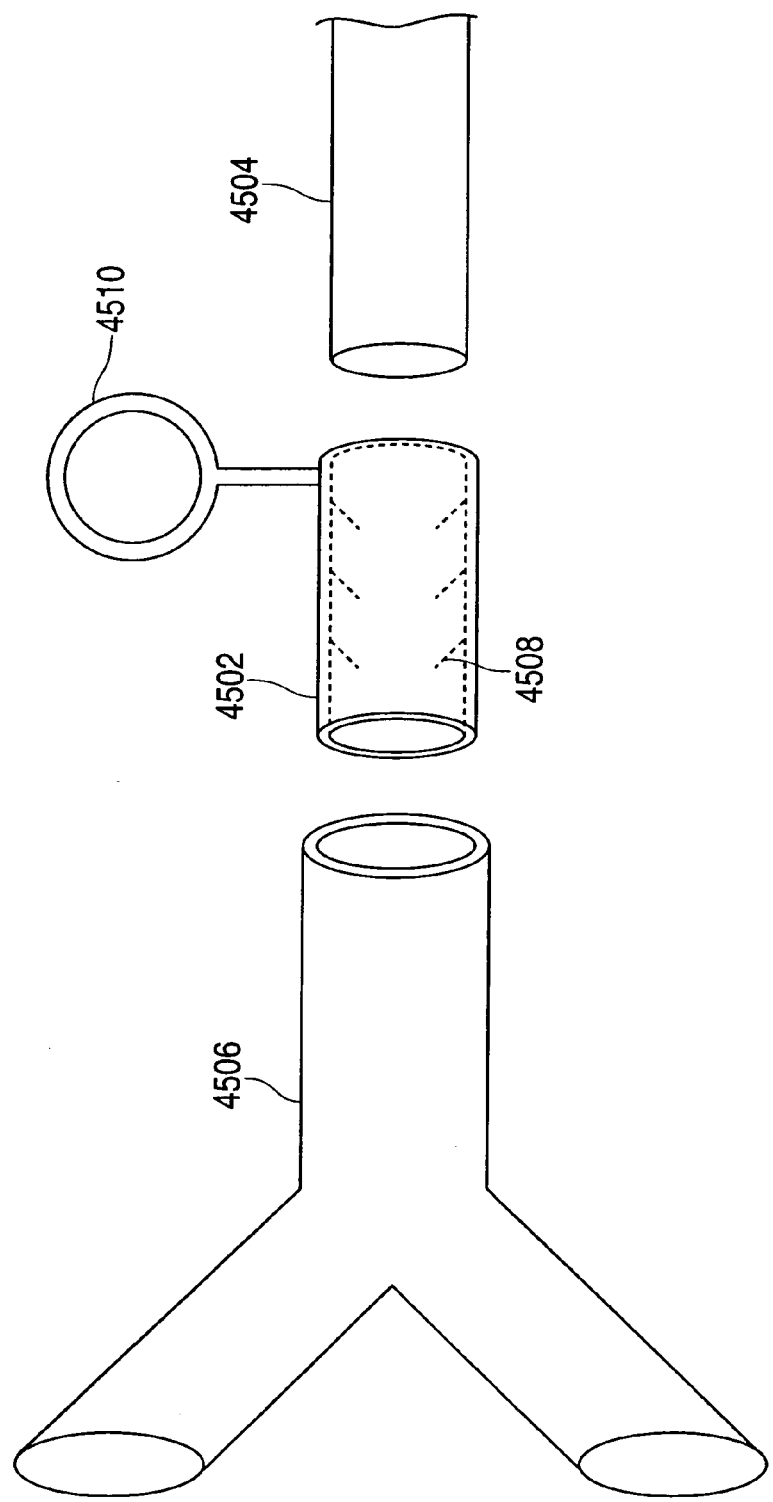
FIG. 45 illustrates an embodiment of a connector used to connect gas delivery tubing, in accordance with the present invention.

FIG. 45 illustrates an embodiment of a connector that may be used to connect gas delivery tubing, in accordance with the present invention. As illustrated in FIG. 45, connector 4502 is operable to connect tubing 4504, which is for example operably connected to a nasal vestibular device, with tubing 4506, which is for example operably connected to a breathing circuit. Connector 4502 includes a plurality of angled ridges 4508 and a fixation tab 4510.

The inner diameter of connector 4502 corresponds with the outer diameter of connecting tubing 4504, so as to enable a female-to-male connection between connector 4502 and tubing 4504. The outer diameter of connector 4502 may correspond with the inner diameter of tubing 4506, so as to enable a male-to-female connection between connector 4502 and tubing 4506. Angled ridges 4508 are shaped to permit insertion of tubing 4504 in a direction toward tubing 4506 and so as to inhibit tubing 4504 from being pulled out of connector 4502 in a direction away from tubing 4506.

In an alternative embodiment, both the outer diameter of tubing 4506 and the outer diameter of tubing 4504 may correspond with the inner diameter of connector 4502, so as to enable a female-to-male connection between connector 4502 and tubing 4504 and to enable a female-to-male connection between connector 4502 and tubing 4506. In such a case, angled ridges 4508 are shaped to permit insertion of tubing 4504 in a direction toward tubing 4506, to permit insertion of tubing 4506 in direction toward tubing 4504, to inhibit tubing 4504 from being pulled out of connector 4502 in a direction away from tubing 4506 and to inhibit tubing 4506 from being pulled out of connector 4502 in a direction away from tubing 4504.

Further, each outer end surface of connector 4502 may be tapered to fit a standard connector, e.g., 15 mm.

Fixation tab 4510 aids in the withdrawal of connector 4502 from breathing circuit connector tube 4506 and further provides a fixation point to the patient for stabilization of the apparatus.

Connector 4502 may be made of the same mold, and at the same time as the portion of the nasal vestibular device that is inserted into the patients airway. Accordingly, total cost of the apparatus will be decreased.

The benefits of the connector 4502 therefore are its ability to inhibit disconnection from other tubing and its decreased manufacturing cost. However, a "softness" of the material of connector 4502 would require a design different from conventional thin-walled hard connectors. Specifically, a conventional hard connector inserts into the tubing, i.e. a male-to-female connection. On the contrary, a "soft" connector such as connector 4502 would require a thick wall to provide sufficient structural integrity to allow insertion of the tubing for the female-to-male connection between connector 4502 and the tubing. Because connector 4502 is designed to provide a female-to-male connection between the connector and the tubing, thickness of connector 4502 does not affect gas flow through the connector. Accordingly, gas flow remains constant through the tubing and its connection with the breathing circuit.

Figure 3B:
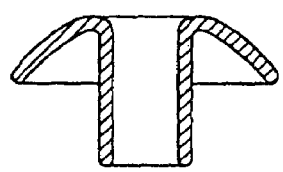
FIG. 3B is a cross-sectional view of the nasal vestibular portion as depicted in FIG. 3A.
Figure 4A:
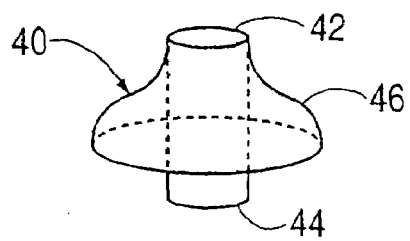
FIG. 4A illustrates another exemplary embodiment of a nasal vestibular portion that may be used with the gas delivery device in accordance with the present invention.
Figure 4B:
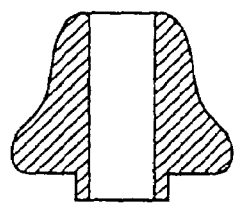
FIG. 4B is a cross-sectional view of the nasal vestibular portion as depicted in FIG. 4A.

FIGS. 3A and 4A illustrate exemplary embodiments of nasal vestibular portions that may be used with the gas delivery device in accordance with the present invention. FIGS. 3B and 4B are cross-sectional illustrations of FIGS. 3A and 4A, respectively.

As illustrated in FIG. 3A, the nasal vestibular portion 30 includes a gas flow tube portion 34, a gas delivery port 32 and a rounded protruding portion 36 that is shaped so as to fit into a nasal vestibule and form a seal with the inner surface of the nasal vestibule. In particular, the rounded protruding portion 36 prevents gas from escaping from the nasal vestibule to outside of the nasal vestibule.

FIG. 4A is a second exemplary embodiment of a nasal vestibular portion. A nasal vestibular portion 40 includes a gas flow portion 44, a gas delivery port 42 and a bell-shaped protruding portion 46. Similar to the portion 36 of FIG. 3A, bell-shaped protruding portion 46 is shaped so as to form a seal with the inner surface of the nasal vestibule thereby preventing gas from escaping and the nasal vestibule.

Figure 5A:
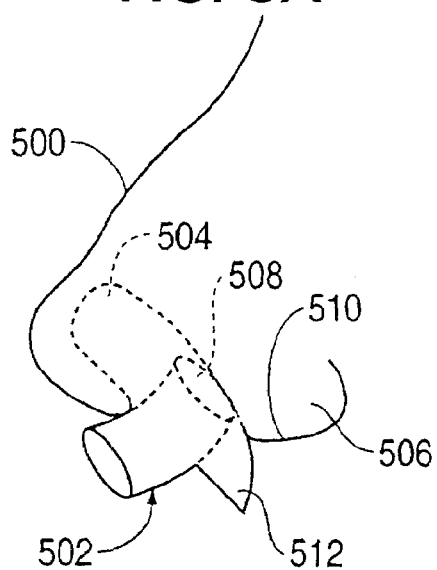
FIG. 5A and 5B illustrate how an embodiment of a nasal vestibular portion according to the present invention is inserted into the nasal vestibule of the patient.
Figure 5B:
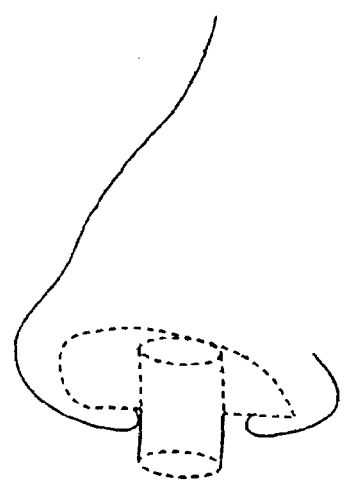

FIGS. 5A and 5B illustrate insertion of a nasal vestibular portion into the nasal vestibule. In the figures, a nasal vestibular portion 502 is inserted into the nose 500. In particular, a superior pole 504 is inserted into the nasal vestibule 506. A nasal vestibular airway 508 is then rotated over the inferior nostril rim 510, and the sharp angle of the wedge 512 locks the nasal vestibular airway 508 in place in the nasal vestibule 506. Sealing forces of the nasal vestibular airway are against the inner surfaces of the nose to provide an outward force on the inner surfaces of the nose.

Figure 14A:
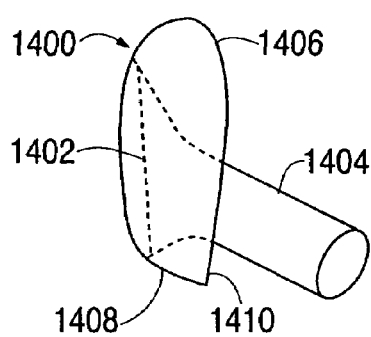
FIG. 14A illustrates another exemplary embodiment of a nasal vestibular portion that may be used with a gas delivery device in accordance with the present invention.
Figure 14B:
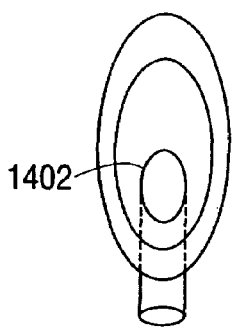
FIG. 14B is a view of the nasal vestibular portion as depicted in FIG. 14A as viewed directly into the gas delivery opening.
Figure 14C:
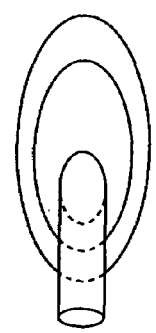
FIG. 14C is a view of the nasal vestibular portion as depicted in FIG. 14A as viewed opposite a direction from that of FIG. 14B.

As illustrated in FIG. 14A, the nasal vestibular portion 1400 includes a gas flow tube portion 1404, a gas delivery port 1402 and a rounded oblong protruding portion 1406 that is shaped so as to fit into a nasal vestibule and form a seal with the inner surface of the nasal vestibule. In particular, the rounded oblong protruding portion 1406 includes a rounded (wedge) shaped leading edge 1408 and a straight (gripping) edge 1410 that maintains a self-retaining position within the nasal vestibule of the patient. FIG. 14B is a view of the interior of the nasal vestibular portion 1400 whereas FIG. 14C is an exterior view of the nasal vestibular portion 1400.

Figure 15A:
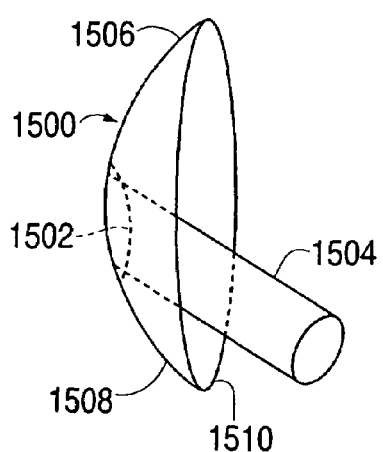
FIG. 15A illustrates another exemplary embodiment of a nasal vestibular portion that may be used with a gas delivery device in accordance with the present invention.
Figure 15B:
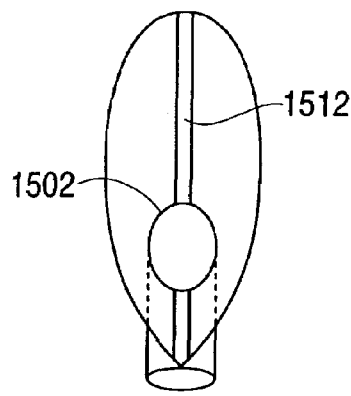
FIG. 15B is a view of the nasal vestibular portion as depicted in FIG. 15A as viewed directly into the gas delivery opening.
Figure 15C:
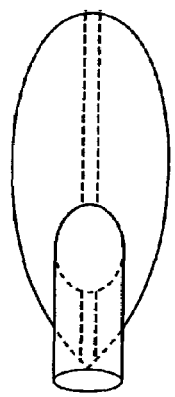
FIG. 15C is a view of the nasal vestibular portion as depicted in FIG. 15A as viewed opposite a direction from that of FIG. 15B.

As illustrated in FIG. 15A, the nasal vestibular portion 1500 includes a gas flow tube portion 1504, a gas delivery port 1502 and a rounded mushroom shaped protruding portion 1506 that is shaped so as to fit into a nasal vestibule and to form a seal with the inner surface of the nasal vestibule. In particular, the rounded mushroom shaped protruding portion 1506 includes a rounded shaped leading 1508 and a straight (gripping) edge 1510. The rounded protruding mushroom shaped portion 1506 can be hollow or solid. FIG. 15B is an interior view of the nasal vestibular portion 1500 of FIG. 15A. As illustrated in FIG. 15B, spine 1512 provides rigidity in the longitudinal axis of the device which causes it to be fixed into the nasal vestibule between the retaining wall of the superior recess and the retaining room of the inferior recess. FIG. 15C is an exterior view of the nasal vestibular portion 1500 of FIG. 15A.

Figure 16A:
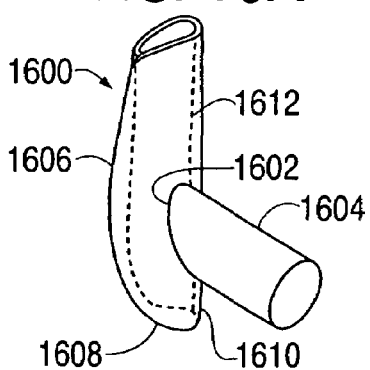
FIG. 16A illustrates another exemplary embodiment of a nasal vestibular portion that may be used with a gas delivery device in accordance with the present invention.
Figure 16B:
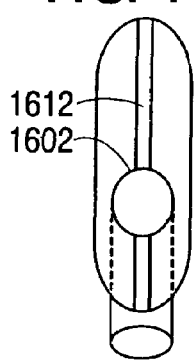
FIG. 16B is a view of the nasal vestibular portion as depicted in FIG. 16A as viewed directly into the gas delivery opening.
Figure 16C:
FIG. 16C is a view of the nasal vestibular portion as depicted in FIG. 16A as viewed opposite a direction from that of FIG. 16B.
Figure 16D:
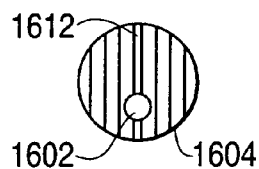
FIG. 16D illustrates an unfolded protruding portion of the nasal vestibular portion of FIG. 16A.

As illustrated in FIG. 16A, the nasal vestibular portion 1600 includes a gas flow tube portion 1604, a gas delivery port 1602 and a folded oblong protruding portion 1612 that is, once folded, shaped so as to fit into a nasal vestibule and form with a seal with the inner surface of the nasal vestibule. In particular, the folded oblong protruding portion 1612 includes a rounded shaped leading edge 1608 and a straight (gripping) edge 1610. FIG. 16B is an interior view of the nasal vestibular portion 1600. As illustrated in FIG. 16B, spline 1612 extends in the longitudinal axis of the nasal vestibular portion to provide rigidity. FIG. 16C is an exterior view of the nasal vestibular portion 1600. FIG. 16D is an interior view of an unfolded protruding portion 1612. As illustrated in FIG. 16D, the unfolded portion 1612 is rounded. As further indicated in FIG. 16D, the rounded unfolded portion may include additional longitudinal spines 1614 to provide further lateral compliance. Please note that as opposed to a rounded shape, the unfolded portion 1612 may have an oval shape.

Figure 17A:
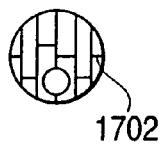
FIGS. 17A–17D illustrate unfolded exemplary embodiments of protruding portions of nasal vestibular portioris in accordance with the present invention.
Figure 17B:
Figure 17C:
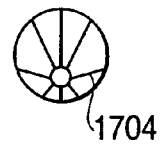
Figure 17D:
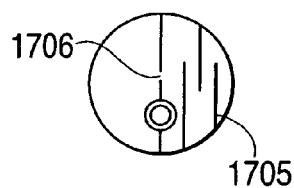

FIGS. 17A–17D illustrate further exemplary embodiments of an unfolded protruding portion. In particular, FIGS. 17A–17D illustrate different exemplary embodiments of splines that provide compliance which causes the nasal vestibular portion to stay fixed into the nasal vestibule between the retaining wall of the superior recess and the retaining rim of the inferior recess. More specifically: FIG. 17A additionally includes lateral spines 1702; FIG. 17B includes circular spines 1703; FIG. 17C includes radially extending spines 1704; and FIG. 17D includes interrupted spines 1705 that allow flexion at critical points 1706.

Figure 30:
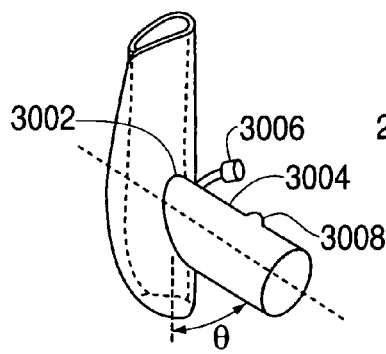
FIG. 30 illustrates another exemplary embodiment of a nasal vestibular portion that may be used with the gas delivery device in accordance with the present invention.

As illustrated in FIG. 30, the nasal vestibular portion gas flow tube portion 3004 having a gas delivery port 1602 and a sampling tube 3006 connection may be coupled with a protruding portion, for example as illustrated in any one of FIGS. 16D–17D. The sampling tube 3006 permits the gas being delivered to the patient to be sampled. The gas flow tube portion 3004 may be adjustably coupled with a protruding portion such that the angle θ is set to maximize comfort to the patient and maintain stability.

Figure 18A:
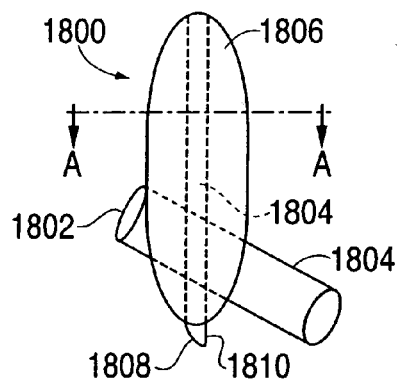
FIG. 18A illustrates another exemplary embodiment of a nasal vestibular portion that may be used with the gas delivery device in accordance with the present invention.
Figure 18B:
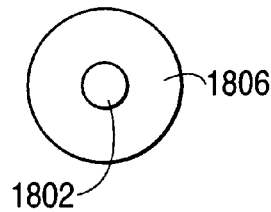
FIG. 18B is a cross-sectional view along line A—A of the nasal vestibular portion of FIG. 18A.
Figure 18C:
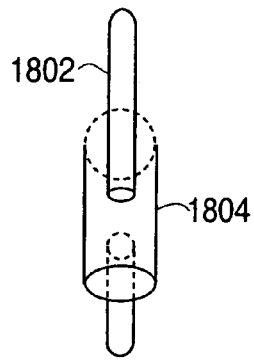
FIG. 18C is a view of the nasal vestibular portion of FIG. 18A without the sponge portion 1806.

As illustrated in FIG. 18A, the nasal vestibular portion 1800 includes a gas flow tube 1804, a gas delivery port 1802, a resilient portion 1806 and a spine portion 1804. The spine portion 1804 includes a leading wedge shaped edge 1808 and a straight (gripping) edge 1810. FIG. 18B is a cross-sectional view of the nasal vestibular portion 1800 along lines A—A in FIG. 18A. As illustrated in FIG. 18B, spine 1802 is within resilient portion 1806. Resilient portion 1806 may include a sponge-like material whereas spine 1802 includes a material that is more rigid than the resilient material 1806. FIG. 18C is an exterior view of nasal vestibular portion 1800 without resilient portion 1806. FIG. 18C illustrates positioning of spine 1802 with respect to gas flow portion 1804.

As illustrated in FIG. 19, a nasal vestibular portion 1900 includes a gas flow tube portion 1904, a gas delivery port 1902 and a conical protruding portion 1906. Gas delivery port 1902 is beveled so as to have a superior pole 1908.

As illustrated in FIG. 20, a nasal vestibular portion 2000 includes a gas flow tube portion 2004, a gas delivery port 2002 and an umbrella shaped portion 2006. The gas delivery port 2002 is beveled so as to have a superior pole 2008.

As illustrated in FIG. 21, a nasal vestibular portion 2100 includes a gas flow tube portion 2104, a gas delivery port 2102 and a rounded umbrella shaped portion 2106. The rounded umbrella shaped portion 2106 is in contact with the gas flow tube portion 2104 at a portion 2108, such that a portion of the gas flow tube extends above the rounded umbrella shaped portion 2106. Gas delivery port 2102 is beveled so as to have a superior pole 2110.

Figure 22:
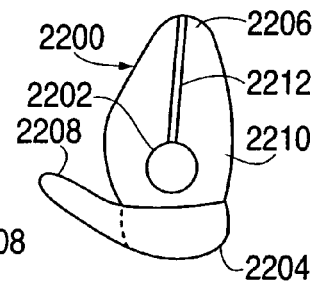
FIG. 22 illustrates another exemplary embodiment of a nasal vestibular portion that may be used with the gas delivery device in accordance with the present invention.

As illustrated in FIG. 22, a nasal vestibular portion 2200 includes a gas flow tube portion 2204, a gas delivery port 2202 and a protruding portion 2210. The protruding portion 2210 includes a superior pole 2006, an inferior pole 2004 and a flat 2008. Spine 2212 provides rigidity to superior pole 2006.

FIG. 23 illustrates a nasal vestibule 2300 having nasal vestibular portion 2200 inserted therein. As illustrated in FIG. 23, superior pole 2206 of the nasal vestibular portion 2200 is positioned within a recess of the nasal vestibule and engages edge 2302 of the nasal vestibule. Pliable inferior pole 2204 enables flap 2208 to lie adjacent to exterior surface 2304 of the nasal vestibule. The nasal vestibular portion 2200 is well suited for infants or others with no well-defined infero-lateral ridge of the nose. Specifically, inferior pole 2204 and flap 2208 are operable to have an adhesive surface applied thereto to permit a seal against the exterior surface 2304 of the nose. The inferior pole 2204 and flap 2208 adhere to the exterior surface-and may be held by manual positioning or elastic strapping or, as indicated above, an adhesive.

Typically, a pair of nasal vestibular portions are used in accordance with the present invention. FIGS. 24A–24D illustrate exemplary embodiments of connector portions used to connect the nasal vestibular portions to a gas delivery system.

As illustrated in FIG. 24A, nasal vestibular portions 2404 having gas delivery ports 2402 are connected to a gas flow tube 2406 via Y connector 2408. FIG. 24B illustrates nasal vestibular portions 2404 having gas delivery portions 2402, wherein the nasal vestibular portions 2404 are connected to flow tube portion 2406 via a T connector 2410. As illustrated in FIG. 24C, nasal vestibular portions 2404 having a gas delivery port 2402, each have a gas flow portion 2606, respectively. The two gas flow portions are connected via a connector, e.g. a string 2412. As illustrated in FIG. 24D, nasal vestibular portions 2404 having gas delivery port 2402 each have a gas flow portion 2606, wherein the gas flow portions 2606 are connected via an interconnecting gas flow portion 2414.

Figure 41A:
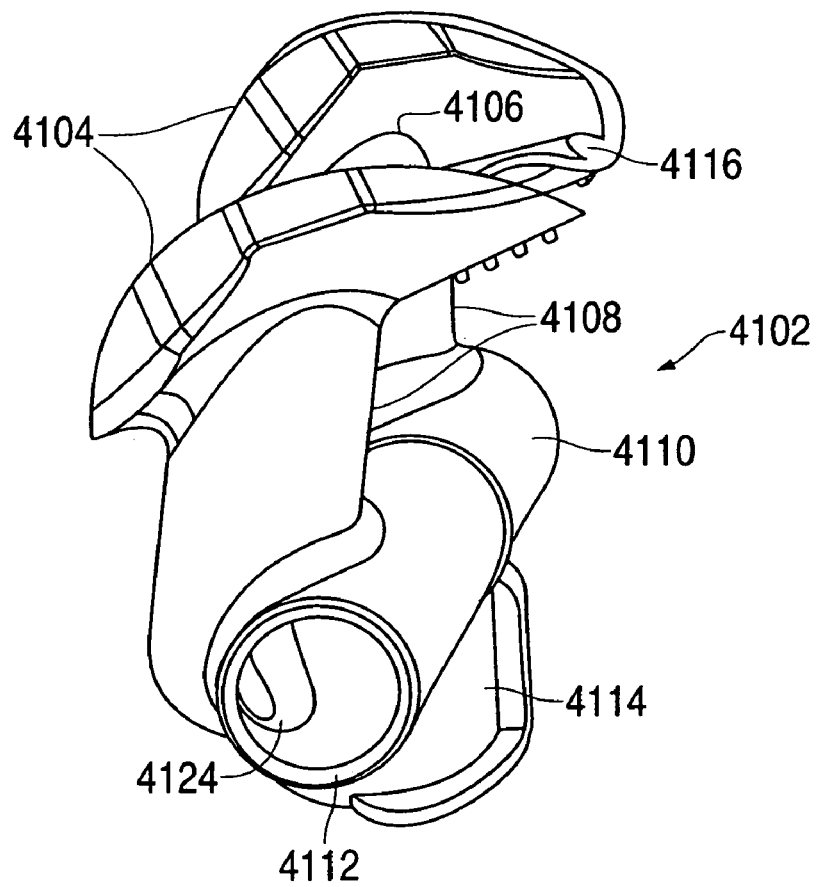
FIGS. 41A–41C illustrate an exemplary embodiment of a nasal vestibular device, in accordance with the present invention.
Figure 41B:
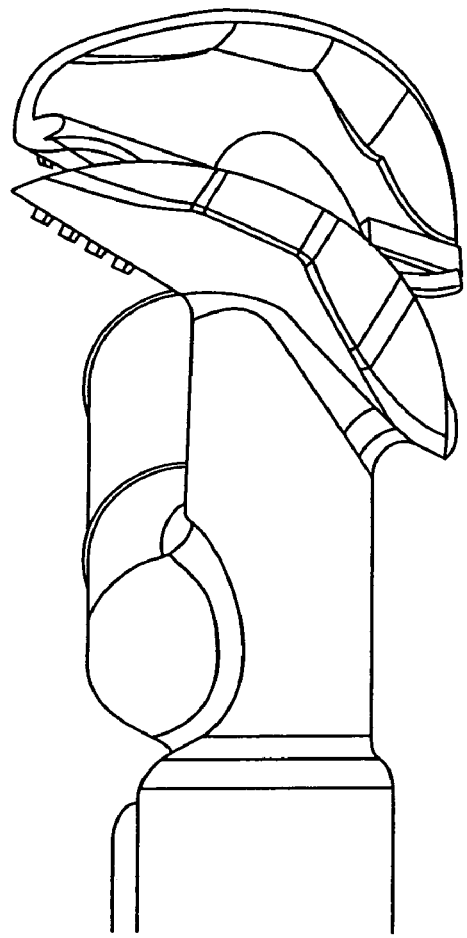
Figure 41C:
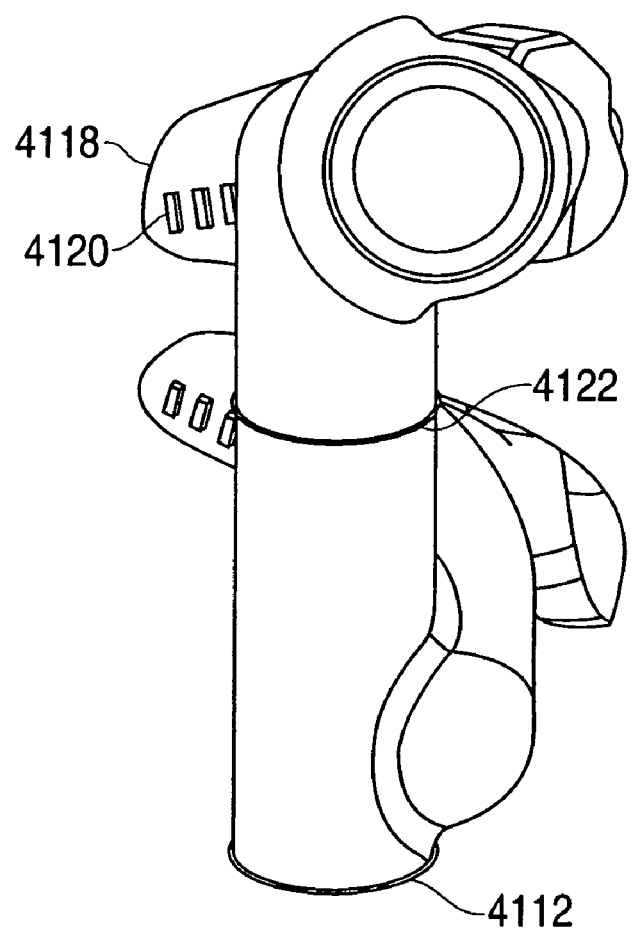

FIGS. 41A–41C illustrate an exemplary embodiment of a nasal vestibular device 4102 in accordance with the present invention. FIG. 41A is an oblique view, FIG. 41B is a side view and FIG. 41C is a bottom view of nasal vestibular device 4102

Nasal vestibular device 4102 includes two nasal vestibular portions 4104 each having a gas delivery port 4106. Further, nasal vestibular device 4102 includes gas flow portion 4108 to provide gas to the gas delivery ports 4106. Further, nasal vestibular device 4102 includes a gas delivery portion 4114 having a connecting portion operable to be connected to a gas delivery system via gas delivery tubing. Nasal vestibular device 4102 still further includes an inter-connecting tube 4110 for providing gas to both gas flow portions 4108, which will be described in more detail below.

As further illustrated in FIGS. 41A–41C, each of nasal vestibular portions 4104 includes a central spine 4116 for providing sufficient rigidity to achieve a self retaining characteristic as discussed above.

As illustrated in FIG. 41C, each nasal vestibular portion 4104 has a curved end 4118 that includes raised marks 4120. Curved end 4118 may be easily trimmed to fit different sized nasal vestibules. Raised marks 4120 provide a simple measuring system for incrementally trimming curved portions 4118 to accurately and reproducibly fit increasingly smaller nasal vestibules. Further, as illustrated in FIG. 41C, curved end portions 4118 have a "toenail-like-configuration" such that they may be easily trimmed with toenail clippers or scissors to retain a curved shape for a comfortable fit in the nasal vestibule.

Raised line 4122, for example as illustrated in FIG. 41C, facilitates the cutting inter-connecting tube 4110 to yield a functional single-insert device to be used in clinical situations where the opposite nasal vestibule of the patient is occupied by another device, e.g., a naso-gastric tube or fiber-optic scope.

Figure 43:
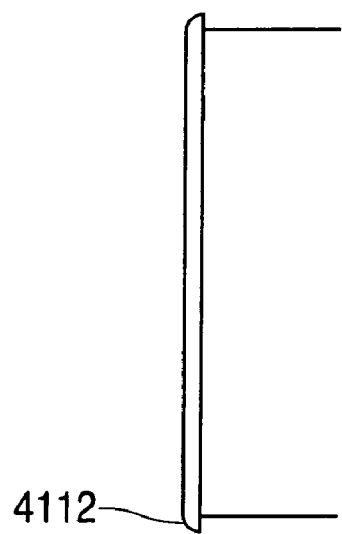
FIG. 43 illustrates an exploded view of ridge 4112 of FIG. 41C.

Hole 4124 is provided to permit venting of expired $CO_2$ gas during expiration. Both raised line 4122 and ridge 4112 are shaped so as to receive a plug cap, in the event that venting is not required. FIG. 43 is an exploded view of ridge 4112.

Figure 44:
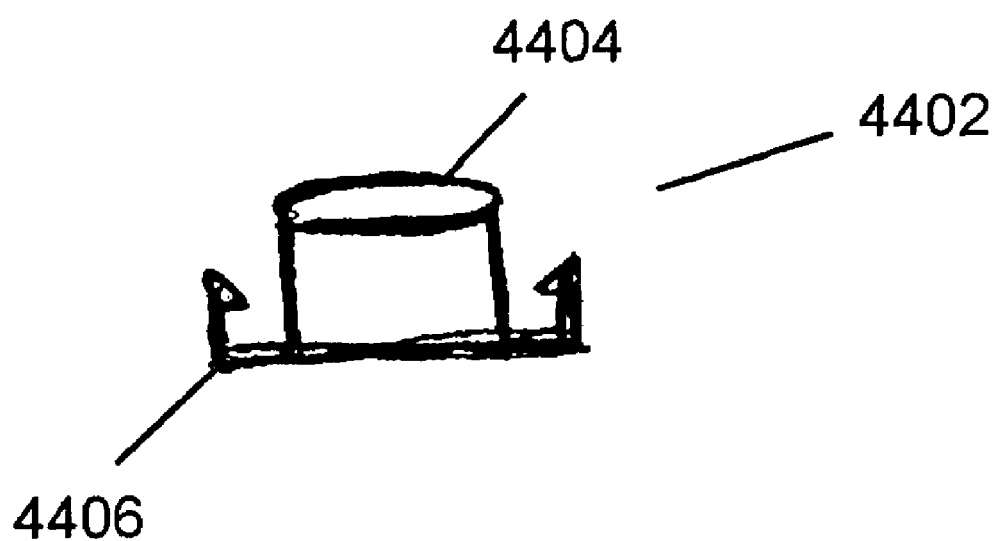
FIG. 44 illustrates a plug cap for use with the nasal vestibular device illustrated in FIGS. 41A–41C.

FIG. 44 illustrates a plug cap for use with the nasal vestibular device 4102. Plug cap 4402 includes a plug portion 4404 shaped to be inserted into tubing 4110 at either portion of ridge 4112 or raised line 4122, in the event that tubing 4110 has been cut at raised line 4122. Plug cap 4408 further includes an annular locking portion 4406 shaped to lock over ridge 4112 or raised line 4122 to retain plug cap 4402 on tubing 4110.

Figure 42:
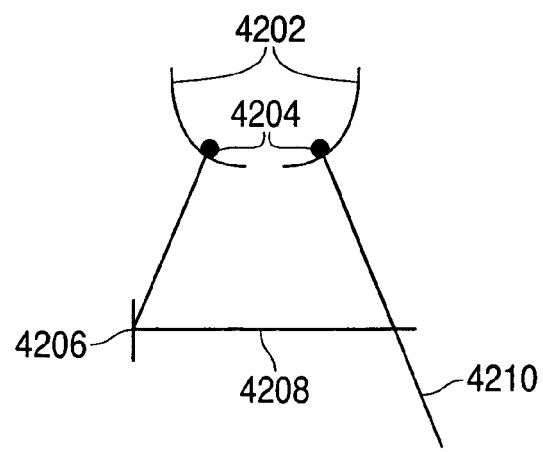
FIG. 42 is a schematic diagram of the nasal vestibular device as illustrated in FIGS. 41A–41C.

FIG. 42 is a schematic diagram of the nasal vestibular device 4102 of FIGS. 41A–41C. As illustrated in FIG. 42, 4202 represents the nasal vestibular portions, 4204 represents the central spines, 4206 represents the plug cap, 4208 represents the inter-connecting tube, and 4210 represents a length of tube for connection to tubing of the breathing circuit.

As illustrated in FIG. 25A, gas flow connector 2500 comprises connector portion 2506, flow tube portion 2504, first vestibular portion delivery tube 2501, second vestibular portion delivery tube 2512, connecting tube portion 2508 and gas delivery ports 2502. As illustrated in FIG. 25B, a first vestibular portion 2514 and second vestibular portion 2506 are respectively disposed on tube portions 2510 and 2512.

FIG. 26 illustrates a person having a gas flow connector and nasal vestibular portion of FIGS. 25A–25C inserted into nose 2506. In particular, the head strap 2612 placed over ears 2604 is connected to the nasal vestibular device at 2610. The head strap is operable to pivot the gas flow connector and nasal vestibular portion up into the nasal vestibule to lock behind the cartilaginous rim of the nasal vestibule.

FIG. 6 illustrates a gas delivery system in accordance with an exemplary embodiment of the present invention. As depicted in FIG. 6, the gas delivery system 600 includes a gas circuit 602 in addition to a nasal vestibular portion 604 for administering gas into the nasal vestibule of the patient, a positive pressure gauge 606 and a supplemental gas providing system 608.

Figure 7:
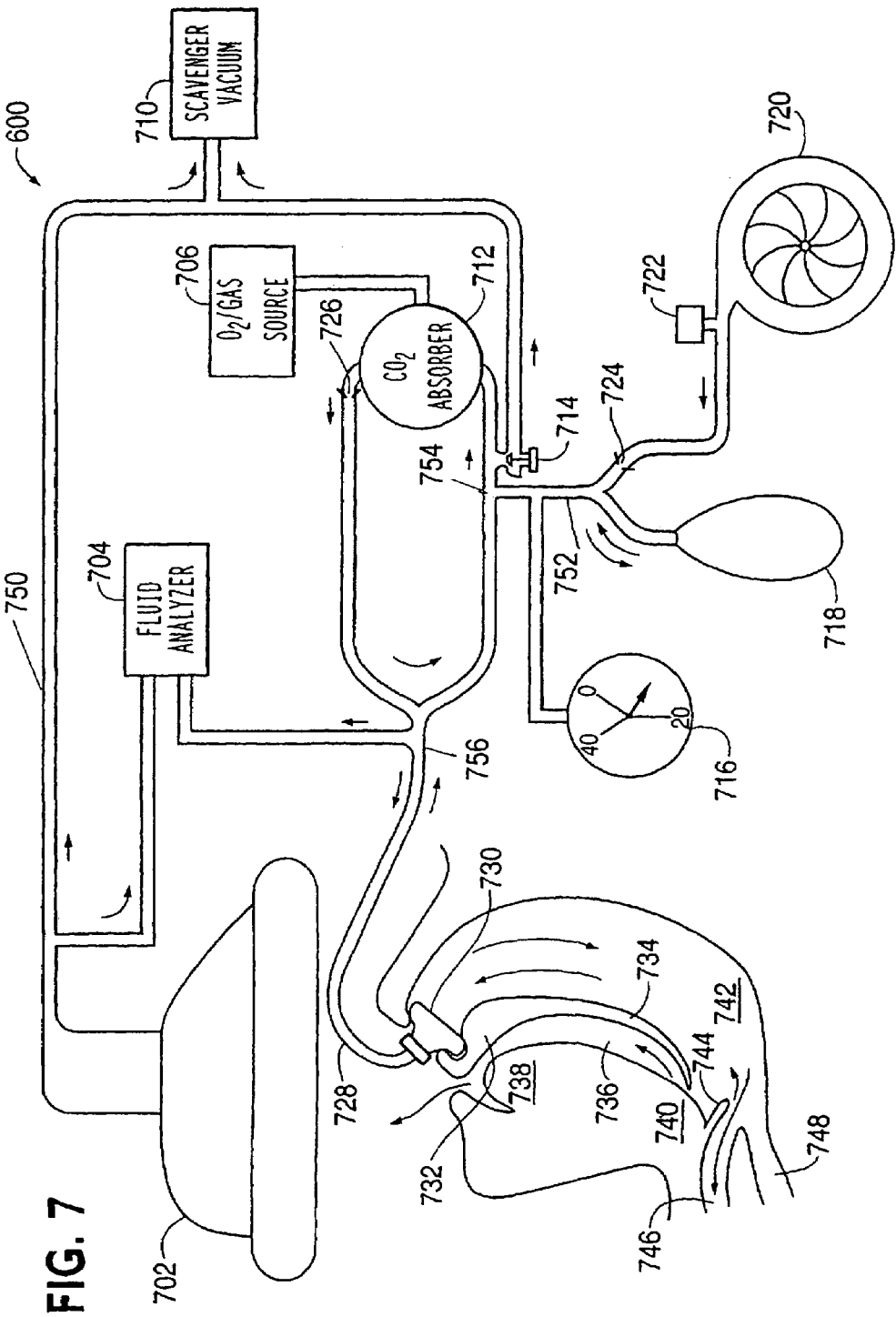
FIG. 7 is a more detailed illustration of a gas delivery system in accordance with the present invention.

FIG. 7 is a more detailed illustration of a gas delivery system in accordance with the present invention. As depicted in FIG. 7, gas delivery system 600 includes a scavenging device 702, a gas analyzer 704, a primary gas source 706, a scavenging vacuum 710, a $CO_2$ absorber 712, a valve 714, a positive pressure gauge 716, a respiration monitoring device 718, a supplemental gas source 720, a valve 722, a valve 724, a valve 726, gas delivery hose 728, and a nasal vestibular portion 730. Tubing 750 connects, in gas flow communication, scavenging device 702, gas analyzer 704, primary gas source 706, scavenging vacuum 710, $CO_2$ absorber 712, valve 714, and valve 726. Tubing 752 connects, in gas flow communication, positive pressure gauge 716, respiration monitoring device 718, supplemental gas source 720, valve 722, and valve 724.

Item 754 is a connection point for tubing 752 to connect, in gas flow communication, with tubing 750. Similarly, item 756 is a connection point for tubing 728 to connect, in gas flow communication, with tubing 750. Accordingly, the tubing 752, and its associated devices, and tubing 728 and its associated nasal vestibular portion may be attached to a pre-existing gas delivery system comprising a scavenging device, a gas analyzer, a primary gas source, scavenging vacuum, and $CO_2$ absorber. Alternatively, items 756 and 754 need not exist, wherein the entire gas delivery system 600 is unitary.

A scavenging portion of gas delivery system 600 includes scavenging device 702 and scavenger vacuum 710. An exemplary embodiment of scavenging-device 702 is a scavenging mask, which may be placed over the face of the patient. The scavenger vacuum 710 provides suction to retrieve gas expired through the mouth of the patient and thereby prevent leakage of an anesthetic gas, for example, into the surgical field. Furthermore, a portion of the scavenged gasses are analyzed by gas analyzer 704 in order to determine the composition of the gasses. Although a scavenging-portion is not required for the gas delivery system in accordance with the present invention, its addition may be desired to prevent contamination of expired anesthetic into the surgical field and to reduce fire hazards resulting therefrom.

Gas source 706 provides the primary gas to be administered to the patient. The primary gas is oxygen used to oxygenate a patient. Further, the primary gas may include an anesthetic medication to be administered to the patient. Still further, the primary gas may include air, nitrogen, or another gas to be administered to the patient. Alternatively, the primary gas may be a mixture of oxygen, anesthetic medication, and another gas.

Valve 726 comprises a one-way valve which forces gas to flow unidirectional, thereby creating a circular flow of gas through $CO_2$ absorber 712. $CO_2$ absorber 712, reduces the amount of $CO_2$ within the gas circulated through the gas delivery system 600.

Supplemental gas source 720 may be an air generator for providing a constant flow rate of air. Valve 722 comprises an adjustable valve, for example, a manually adjustable valve, for adjusting the gas flow rate provided by supplemental gas source 720. Valve 724 is a unidirectional valve that prevents back flow of gas into supplemental gas source 720.

Supplemental gas source 720 may comprise a constant airflow generator capable of delivering accurate flow rates between 0 and 20 liters per minute within airway pressures of 0 to 20 centimeters of water. Such a supplemental gas source may provide fresh air to replenish oxygen and to facilitate removal of $CO_2$. The air-generator may be used to deliver an aesthetic gas and to facilitate its removal at the end of anesthesia by increasing flow rates to "flush-out" the system. A battery-operated, portable constant airflow generator may be used to maintain the functional residual capacity and to introduce air into the lungs of the hypoventilation patient to promote oxygenation and to prevent atelectasis from absorption of oxygen during transport of the patient and recovery from anesthesia. Standard disposable anesthesia filters may be incorporated into or used in conjunction with the constant airflow generator to allow the patient to breath the same ambient air as the anesthesia providers minus any possible bacterial and viral contamination. The introduction of a cost-effective supply of air to the anesthesia circuit also decreases the risk of fire in the operating room. A manually-adjustable constant airflow generator (as opposed to the constant pressure-variable flow generators used in the treatment of sleep apnea) allows the pressure to vary within the anesthesia circuit to produce a more typical in-and-out movement of the reservoir bag, better monitoring of spontaneous respirations, better venus return and easier detection of disconnects.

Figure 34A:
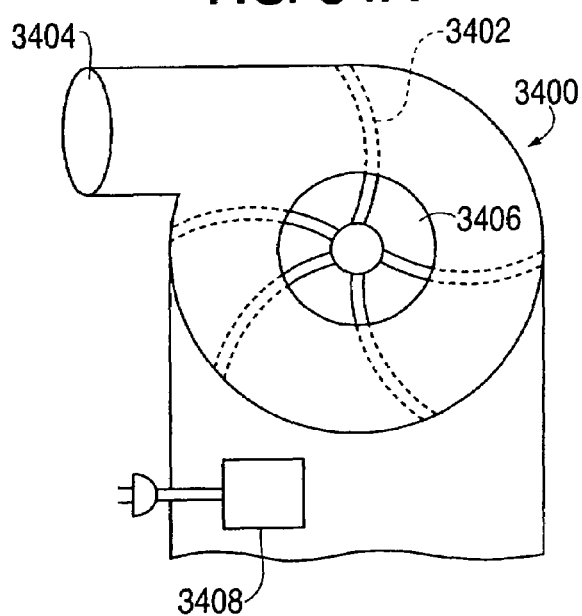
FIG. 34A is a side view of a constant-flow air generator in accordance with one embodiment of the present invention.
Figure 34B:
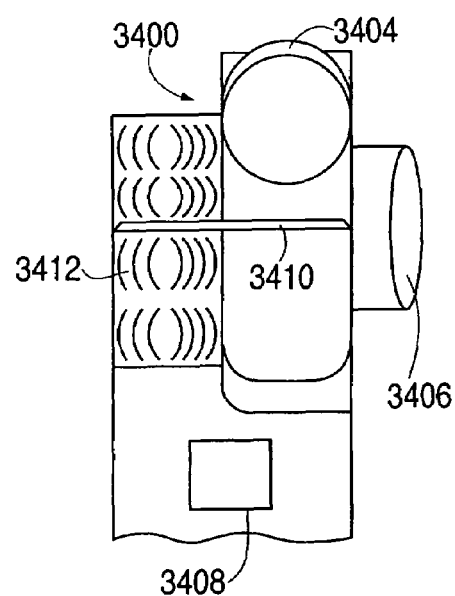
FIG. 34B is a front view of a constant-flow air generator of FIG. 43A.

The constant airflow generator could take any of several forms, e.g., piston airflow generator, diaphragm airflow generator, rotary vane airflow generator, etc. FIGS. 34A and 34B illustrate a constant airflow generator in accordance with one embodiment of the present invention. Specifically, constant airflow generator 3400 comprises a housing surrounding a brushless motor 3412, thereby eliminating sparks, and having sufficient power (and, a manual adjustable rate in one-half liter increments from 0 to 20 liters) to deliver a constant flow within a pressure range of 0 to 20 cm of water. The motor includes rotary fan 3402 and a power source 3408. This type of constant airflow generator will generate a constant pressure head of air to a regulator determined by the tightness of fit between the rotary vanes and the constant airflow generator housing combined with the revolutions per minute and torque of the motor. The power source may be a battery or an optional input from an external power source. Flows and pressures in excess of the capacity of the constant airflow generator would be dissipated through the intake opening of the housing of the constant airflow generator. The constant airflow generator 3400 may include greaseless bearings thereby eliminating a use for oil to lubricate the system. Further, Teflon surfaces may be used to reduce friction of the rotary parts. Air entering the system at input 3406 leaves the constant airflow generator at output 3404. A pressure-relief valve that "pops-off" at 20 centimeters of water and a one way valve, which prevents tank oxygen from backing-up into the constant airflow generator may additionally be employed at the output of the air-generator. By using a battery as the power source 3408, the constant airflow generator is detachable from a charger and is readily transportable to another recharging location, e.g. a recovery room. An attachment device, such as a hook or strap, can be provided to allow the constant airflow generator to be attached to a stretcher rail during transport.

Figure 35:
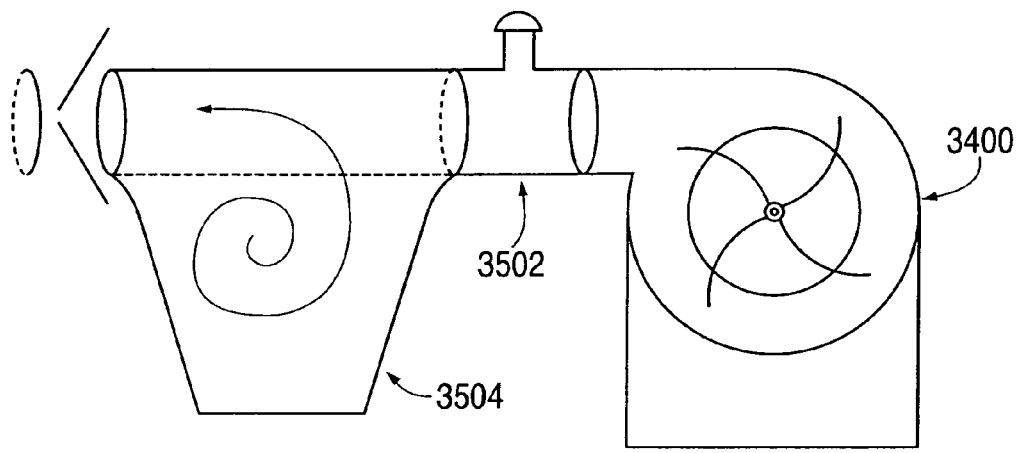
FIG. 35 is a side view of a constant-flow air generator and a draw-over vaporizer in accordance with one embodiment of the present invention.

FIG. 35 illustrates a constant airflow generator 3400 placed in-line with a "draw-over" vaporizer 3504. The combination of the constant airflow generator and the vaporizer adds anesthetic gas to a circle system or can totally power a simple non-rebreathing system requiring, at most, the addition of small amounts of tank oxygen (a simple "battle-field" system).

An anesthesia circuit can include a constant airflow generator in accordance with the present invention, or in the alternative, a constant airflow generator in accordance with the present invention can be added to a pre-existing anesthesia circuit. A standard "T-connector" could be used to connect the constant airflow generator to the circuit. It should be noted that constant airflow generator is outside the circuit with the purpose of adding air to the circuit. This as opposed to being placed in the circuit for the purpose of speeding up circulation of anesthesia gases. If a pre-existing anesthesia circuit is modified to include a constant airflow generator in accordance with the present invention, and the constant airflow generator is subsequently removed, the input port 2702 of the T connector can be plugged with a plug 2704 as illustrated in FIG. 27. Alternatively the input port 2802 of the T connector can be capped with a cap 2804 as illustrated in FIG. 28.

When detached from the anesthesia machine, the inflow T connector of the breathing circuit can be capped with a cap having a port through which oxygen can be delivered from a portable tank. The detached expiratory limbed can be attached to a "T" to which is attached a reservoir bag and a conventional adjustable "pop-off" valve. The detached circuit with the attached constant airflow generator thereby becomes a self-sustaining positive-pressure and fresh airflow breathing circuit with a capacity for manual assistance.

A conventional bacterial filter can be incorporated to either or both of the intake and output of the constant airflow generator in accordance with the present invention in order to sterilize the gas being delivered to a patient.

Reservoir 718 is expandable and contractible in response to the divergence of gas flowing therein, respectively. Reservoir 718 may therefore be used as a visual indicator of the patient's respiration.

Positive pressure gauge 716, monitors the positive pressure of the gas within gas delivery system 600. Positive pressure gauge 716 should be capable of measuring pressure between 0 and 20 cm of water. Specifically, because pressures in excess of 20 cm of water has been shown to blow air into the stomach, positive pressure gauge 716 must be able to measure at least 20 cm of water. More importantly, positive pressure gauge 716 in should display the detected pressure at a precision that would readily communicate the difference between an inspiration and an expiration of the patient.

An exemplary method of operation of gas delivery system 600 as illustrated in FIG. 7 will now be explained with reference to the flow charts of FIG. 8 through FIG. 13B.

Referring to FIG. 8, after nasal vestibular portion 730 has been inserted into the nasal vestibule of the patient, the process is started (S802), and an alternating positive airway pressure is provided to the patient (S804). In particular, supplemental gas source 720 provides a supplemental gas, the flow rate of which is constant and is manually set by manual adjustment valve 722. In this exemplary embodiment, the supplemental gas is air. The gas enters the gas circuit 602 via unidirectional valve 724 and eventually enters the nasopharynx 742 of the patient by way of nasal vestibular portion 730. The gas flow rate is set to achieve a positive pressure that is less than 20 cm of water, which is monitored through the positive pressure gauge 716. The gas flows from nasopharynx 742, past the epiglottis 744, into the trachea 746 and continues into the lungs. Expiration of the patient provides back flow of expired gas back through nasopharynx 742 and through the oral cavity 736. Gas in oral cavity 746 is expired out through the mouth, whereas back flow of gas in nasopharynx 742 returns into nasal vestibular portion 730 and returns into the gas delivery system 600. Respirations and expirations of the patient are monitored via constriction and expansion of reservoir 818. Further, as discussed above, a scavenging system may be used wherein, for example, scavenging mask 702 is placed over the patient's face. Scavenging mask 802, as operably connected to the scavenging vacuum 710, scavenges any gasses that may be respired from the patient. Furthermore, gas analyzer 704 analyses a portion of the scavenged gasses in order to determine the composition thereof.

Returning to FIG. 8, once the PPP is established, oxygen is administered (S806). In this exemplary embodiment, referring to FIG. 7, a second gas source, which is primary gas source 806 provides oxygen, which is ultimately administered to the patient via nasal vestibular portion 730. However, primary gas source 806 may additionally be constructed so as to provide oxygen via a mixture of oxygen and other gasses such as nitrogen or air. Furthermore, primary gas source 806 might not be needed if supplemental gas source 720 is operable to provide sufficient oxygen to the patient.

Once the oxygen has been administered to the patient, the patient's oxygen levels are monitored (S808) by any conventional method, such as with a pulse oximeter. If the oxygen level is determined to be too low (S818), then the oxygen provided to the patient is increased (S812). On the contrary, if the oxygen level of the patient is determined to be too high (S814), then the oxygen level is decreased (S816). Accordingly, a flow rate of gas from primary gas source 806 may be adjusted until the patient is receiving an appropriate amount of oxygen.

If the oxygen supply must be increased, the constant flow rate of the supplemental gas from the supplement gas source 720 should be adjusted accordingly in order to maintain a constant total gas flow rate, which is the sum of the supplemental gas flow rate and the oxygen flow rate. Ideally, if the oxygen flow rate is to be increased by a predetermined amount, then the gas flow rate of the supplemental gas source 720 should be concurrently decreased by an equal amount in order to maintain a constant total gas flow rate of the combined oxygen and supplemental gas. A system may be easily constructed with conventional technology so as to easily accomplished this aspect. In particular, such a system may include a servo system for automatically adjusting the flow rates of the supplemental gas source 720 and the primary gas source 806 so as to maintain a constant total gas flow rate.

Nevertheless, when it is determined that the oxygen level supplied to the patient is too low (S810) wherein the oxygen supply must be increased (S812), the two exemplary procedures as illustrated in FIGS. 9A and 9B may be followed. In particular, FIGS. 9A and 9B illustrate exemplary procedures, wherein the increase in oxygen and the decrease in the supplemental gas are not performed simultaneously. These procedures therefore are not ideal because the total gas flow rate changes slightly when one gas flow rate is decreased but before the other gas flow rate is increased. However, the systems required to perform the procedures described with respect to FIGS. 9A and 9B may be less complicated and less expensive to construct because a servo system for automatically adjusting the flow rates would not be required.

As illustrated in FIG. 9A, at the start of the procedure (S902), the gas flow rate is determined (S904). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the oxygen flow rate is then increased by a predetermined amount (S906). Subsequently, in order to maintain a constant gas flow rate, the supplemental gas is decreased in an equal amount (S908), and process stops (S910).

An alternate procedure is illustrated in FIG. 9B. At the start of the procedure (S902), the gas flow rate is determined (S904). Then, the supplemental gas is decreased by a predetermined amount (S912). Subsequently, in order to maintain a constant gas flow rate, the oxygen flow rate is increased in an equal amount (S914), and process stops (S916).

Returning to FIG. 8, wherein it is determined that the oxygen administered to the patient needs to be decreased (S816), ideally, if the oxygen flow rate is decreased by a predetermined amount, then the gas flow rate of the supplemental gas source 720 should be concurrently increased by an equal amount in order to maintain a constant total gas flow rate of the combined oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when it is determined that the oxygen level supplied to the patient is too high (S814) wherein the oxygen supply must be increased (S816), the two exemplary procedures as illustrated in FIGS. 10A and 10B may be followed. In particular, FIGS. 10A and 10B illustrate exemplary procedures, wherein the decrease in oxygen and the increase in the supplemental gas are not performed simultaneously. These procedures therefore are not ideal because the total gas flow rate changes slightly when one gas flow rate is decreased but before the other gas flow rate is increased. However, the systems required to perform the procedures described with respect to FIGS. 10A and 10B may be less complicated and less expensive to construct because a servo system for automatically adjusting the flow rates would not be required.

As illustrated in FIG. 10A, at the start of the procedure (S1002), the gas flow rate is determined (S1004). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the oxygen flow rate is then decreased by a predetermined amount (S1006). Subsequently, in order to maintain a constant gas flow rate, the supplemental gas is increased in an equal amount (S1008), and process stops (S1010).

An alternate procedure is illustrated in FIG. 10B. At the start of the procedure (S1002), the gas flow rate is determined (S1004). Then, the supplemental gas is increased by a predetermined amount (S1012). Subsequently, in order to maintain a constant gas flow rate, the oxygen flow rate is decreased in an equal amount (S1014), and process stops (S1016).

Returning to FIG. 8, once the oxygen level of the patient is appropriate, a general anesthetic may be administered (S818). In this exemplary embodiment, the anesthetic is administered through inhalation.

Ideally, if the anesthetic is administered at a predetermined flow rate, then the gas flow rate of the gas from supplemental gas source 720 in addition to the oxygen flow rate from the primary gas source 706 should be decreased by an equal amount in order to maintain a constant gas flow rate of the combined anesthetic, oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when the anesthetic is to be administered to the patient (S818), the two exemplary procedures as illustrated in FIGS. 11A and 11B may be followed. In particular, FIGS. 11A and 11B illustrate exemplary procedures, wherein the anesthetic is administered in a predetermined amount non-concurrently with a decreasing of the oxygen flow rate and the supplemental gas flow rate by the predetermined amount. These procedures therefore are not ideal because the total gas flow rate changes slightly when one gas flow rate is decreased but before the other gas flow rate is increased. However, the systems required to perform the procedures described with respect to FIGS. 11A and 11B may be less complicated and less expensive to construct because a servo system for automatically adjusting the flow rates would not be required.

As illustrated in FIG. 11A, at the start of the procedure (S1102), the gas flow rate is determined (S104). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the flow rate of the oxygen and the supplemental gas is then decreased by a predetermined amount (S1106). Specifically, the flow rate of the oxygen may be decreased by the predetermined amount, the flow rate of the supplemental gas may be decreased by the predetermined amount, or some portion of each of the oxygen flow rate and supplemental gas flow rate may be decreased such that the total flow rate decrease is equal to the predetermined amount. Subsequently, in order to maintain a constant gas flow rate, the anesthetic is administered in an equal amount (S1108), and process stops (S110).

An alternate procedure is illustrated in FIG. 11B. At the start of the procedure (S1102), the gas flow rate is determined (S1104). Then, the anesthetic is administered by a predetermined amount (S1112). Subsequently, in order to maintain a constant gas flow rate, the flow rate of the oxygen and the supplemental gas is decreased by a predetermined amount (S1114), and process stops (S1116).

Returning to FIG. 8, once the anesthetic has been administered (S818), the patient is monitored so as to determine whether a sufficient amount of anesthetic is being administered (S820). If it is determined that the amount of anesthetic provided to the patient is too low (S822) then the amount of anesthetic provided to the patient is increased (S824). Alternatively, if it is determined that the amount of anesthetic provided to the patient is too high (S826), then the amount of anesthetic provided to the patient is decreased (S828).

Ideally, if the anesthetic is to be increased by a predetermined flow rate, then the gas flow rate of the gas from supplemental gas source 720 in addition to the oxygen flow rate from the primary gas source 706 should be decreased by an equal amount in order to maintain a constant gas flow rate of the combined anesthetic, oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when the anesthetic is to be increased (S824), the two exemplary procedures as illustrated in FIGS. 12A and 12B may be followed. In particular, FIGS. 12A and 12B illustrate exemplary procedures, wherein the anesthetic is increased in a predetermined amount non-concurrently with a decreasing of the oxygen flow rate and the supplemental gas flow rate by the predetermined amount. These procedures therefore are not ideal because the total gas flow rate changes slightly when one gas flow rate is decreased but before the other gas flow rate is increased. However, the systems required to perform the procedures described with respect to FIGS. 12A and 12B may be less complicated and less expensive to construct because a servo system for automatically adjusting the flow rates would not be required.

As illustrated in FIG. 12A, at the start of the procedure (S1202), the gas flow rate is determined (S1204). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the flow rate of the anesthetic is then increased by a predetermined amount (S1206). Subsequently, in order to maintain a constant gas flow rate, the flow rate of the oxygen and the supplemental gas is decreased by the predetermined amount (S1208). Specifically, the flow rate of the oxygen may be decreased by the predetermined amount, the flow rate of the supplemental gas may be decreased by the predetermined amount, or some portion of each of the oxygen flow rate and supplemental gas flow rate may be decreased such that the total flow rate decrease is equal to the predetermined amount. The process then stops (S1210).

An alternate procedure is illustrated in FIG. 12B. At the start of the procedure (S1202), the gas flow rate is determined (S1204). Then, the flow rate of the oxygen and the supplemental gas is decreased by a predetermined amount (S1212). Subsequently, in order to maintain a constant gas flow rate, the anesthetic is increased by the predetermined amount (S1214), and process stops (S1216).

Returning to FIG. 8, wherein it is determined that the anesthetic administered to the patient needs to be decreased (S828), ideally, if the anesthetic is to be decreased by a predetermined flow rate, then the gas flow rate of the gas from supplemental gas source 720 in addition to the oxygen flow rate from the primary gas source 706 should be increased by an equal amount in order to maintain a constant gas flow rate of the combined anesthetic, oxygen and supplemental gas. A system may be easily constructed with conventional technology so as to easily accomplished this aspect. In particular, as discussed above, such a system may include a servo system for automatically adjusting the flow rates of the supplemental gas source 720 and the primary gas source 806 so as to maintain a constant total gas flow rate.

Nevertheless, when the anesthetic is to be decreased (S828), the two exemplary procedures as illustrated in FIGS. 13A and 13B may be followed. In particular, FIGS. 13A and 13B illustrate exemplary procedures, wherein the anesthetic is decreased in a predetermined amount non-concurrently with an increasing of the oxygen flow rate and the supplemental gas flow rate by the predetermined amount. These procedures therefore are not ideal because the total gas flow rate changes slightly when one gas flow rate is decreased but before the other gas flow rate is increased. However, the systems required to perform the procedures described with respect to FIGS. 13A and 13B may be less complicated and less expensive to construct because a servo system for automatically adjusting the flow rates would not be required.

As illustrated in FIG. 13A, at the start of the procedure (S1302), the gas flow rate is determined (S1304). In particular, the gas flow rate of the supplemental gas provided by supplemental gas source 720 in addition to the gas flow rate of primary gas source 706 is determined by way of a gas flow sensor. Further, in one exemplary embodiment, the gas flow rate of the supplemental gas provided by supplemental gas source 720 is determined by a first gas flow sensor, whereas the gas flow rate of primary gas source 706 is determined by a second gas flow sensor. In any event, the flow rate of the oxygen and the supplemental gas is then increased by a predetermined amount (S1306). Specifically, the flow rate of the oxygen may be increased by the predetermined amount, the flow rate of the supplemental gas may be increased by the predetermined amount, or some portion of each of the oxygen flow rate and supplemental gas flow rate may be increased such that the total flow rate increase is equal to the predetermined amount. Subsequently, in order to maintain a constant gas flow rate, the flow rate of the anesthetic is decreased by the predetermined amount (S1308). The process then stops (S1310).

An alternate procedure is illustrated in FIG. 13B. At the start of the procedure (S1202), the gas flow rate is determined (S1304). Then, the anesthetic is decreased by a predetermined amount (S1312). Subsequently, in order to maintain a constant gas flow rate, the flow rate of the oxygen and the supplemental gas is increased by the predetermined amount (S1314), and process stops (S1316).

Steps S818 through S830 are repeated until the proper amount of anesthetic is provided to the patient, wherein the process stops (S830).

If the anesthetic is to be administered intravenously, then a simplified embodiment of the present invention may be used. In particular, the oxygen provided to the patient is adjusted to a proper level while the supplemental gas provider administers supplemental gas to maintain a constant gas flow rate. In other words, the oxygen and supplemental gas may not be further adjusted so as to accommodate an additional gas flow of anesthetic, because the anesthetic has been administered intravenously.

In the exemplary embodiment described above, supplemental gas source 706 provides both oxygen and anesthetic. In an alternative embodiment, two separate gas sources may be provided, one for administering oxygen and one for administering anesthetic. In another embodiment, supplemental gas source only administers oxygen, wherein an inhalation anesthetic is not required.

Further, the device according to the present invention can be tolerated without anesthesia or sedation. It is less likely to cause claustrophobia. Further, while existing devices are cumbersome and surround the face and head with a mask and straps, and a bag, the nasal vestibular airway can be paired and worn like eyeglasses with hooks or straps over the ears.

Furthermore, the nasal vestibular airway according to the present invention may be applied to deeply sedated patients in dental surgery. The device of the present application may even be considered for use in veterinary medicine, where there is no satisfactory means of assisting a spontaneously breathing but respiratory-compromised animal.

Figure 38:
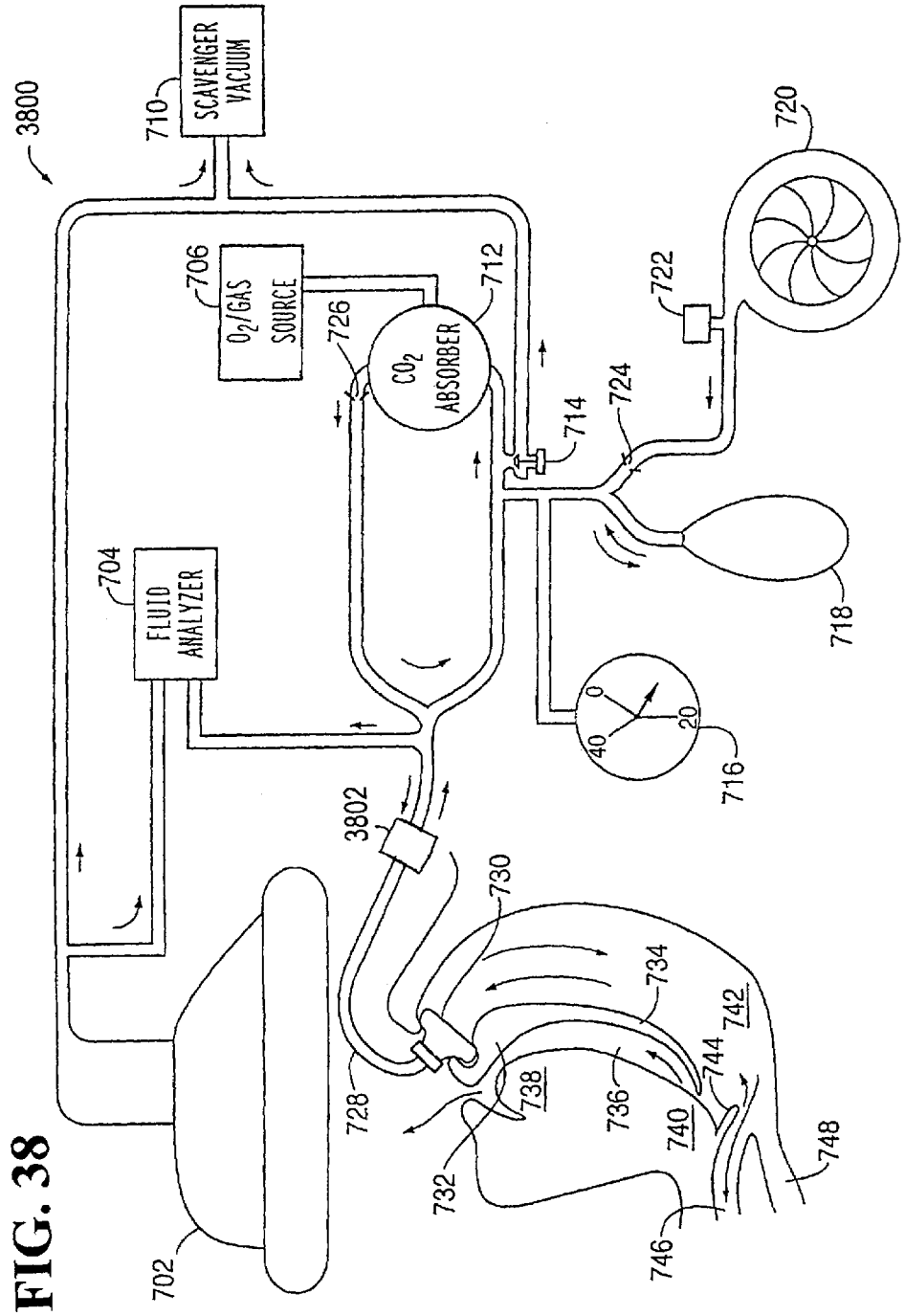
FIG. 38 is a detailed illustration of another embodiment of a gas delivery system in accordance with the present invention.

FIG. 38 is a more detailed illustration of a gas delivery system in accordance with another embodiment of the present invention. The gas delivery system of FIG. 38 is similar to that as illustrated in FIG. 7. However, the gas delivery system 3800 as depicted in FIG. 38 differs from gas delivery system 600 as depicted in FIG. 7 in that the gas delivery system 3800 includes a breathing-circuit stethoscope 3802. Accordingly, a discussion of the similar aspects between the gas delivery system 3800 as depicted in FIG. 38 and the gas delivery system 600 as depicted in FIG. 7 will not be repeated.

A breathing-circuit stethoscope or in-line anesthesia circuit stethoscope allows quick and convenient monitoring of amplified breath sounds within the anesthesia circuit. This is particularly useful in the spontaneously breathing, non-intubated patient where the flow of air through the tubing and the valves of the circuit combine with flow through the patient's anatomy to produce sounds characteristics of adequate flow, obstructed flow, circuit disconnects, fluid in the airway, etc. These sounds are generally much amplified by the circuit over those that might be heard by direct application of a stethoscope to the patient. The circuit stethoscope may be permanently attached to the anesthesia machine without need to adapt to each patient individually. When connected by microphone or a wireless transmitter (such as, for example, in combination with input from other sources, e.g., pre-cordial stethoscope, monitor speaker, etc.) it becomes an "anaesthetist-friendly" continuous multi-parameter monitor.

Figure 31:
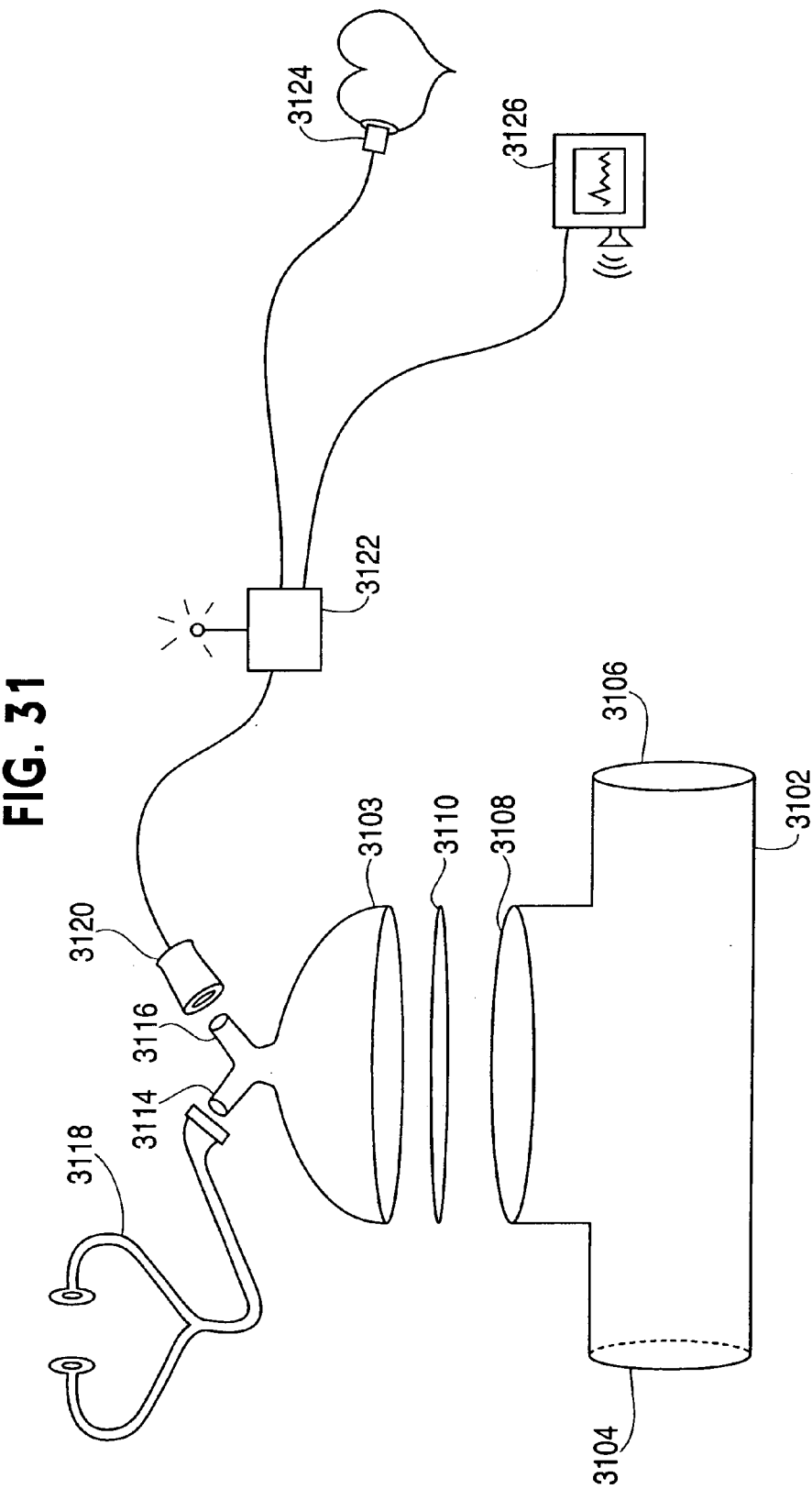
FIG. 31 illustrates an in-line anesthesia-circuit stethoscope in accordance with the present invention.

FIG. 31 illustrates an exemplary embodiment of an breathing circuit stethoscope in accordance with the present invention. As illustrated in FIG. 31, the breathing circuit stethoscope includes a T-connector 3102 having an input port 3104 and an output port 3106 for connection with gas flow tubes of the anesthesia circuit, a port 3108 for communication with a diaphragm 3110 and a bell cap portion 3102. The diaphragm may comprise, for example, a thin plastic providing an air-tight pressure seal over port 3108. The bell cap 3102 may comprise a plurality of connector ports, for example 3114 and 3116. As illustrated in FIG. 31, connector port 3114 is operable to be connected to a stethoscope 3118 such that a doctor may monitor the sounds in the anesthesia circuit.

Furthermore, connector port 3116 is operable to be connected with microphone 3120 which may additionally be attached to a wireless electronic stethoscope transmitter 3122 of which may additionally be connected to a pre-cordial stethoscope 3124 to monitor the heart and a monitor speaker 3126.

Figure 46:
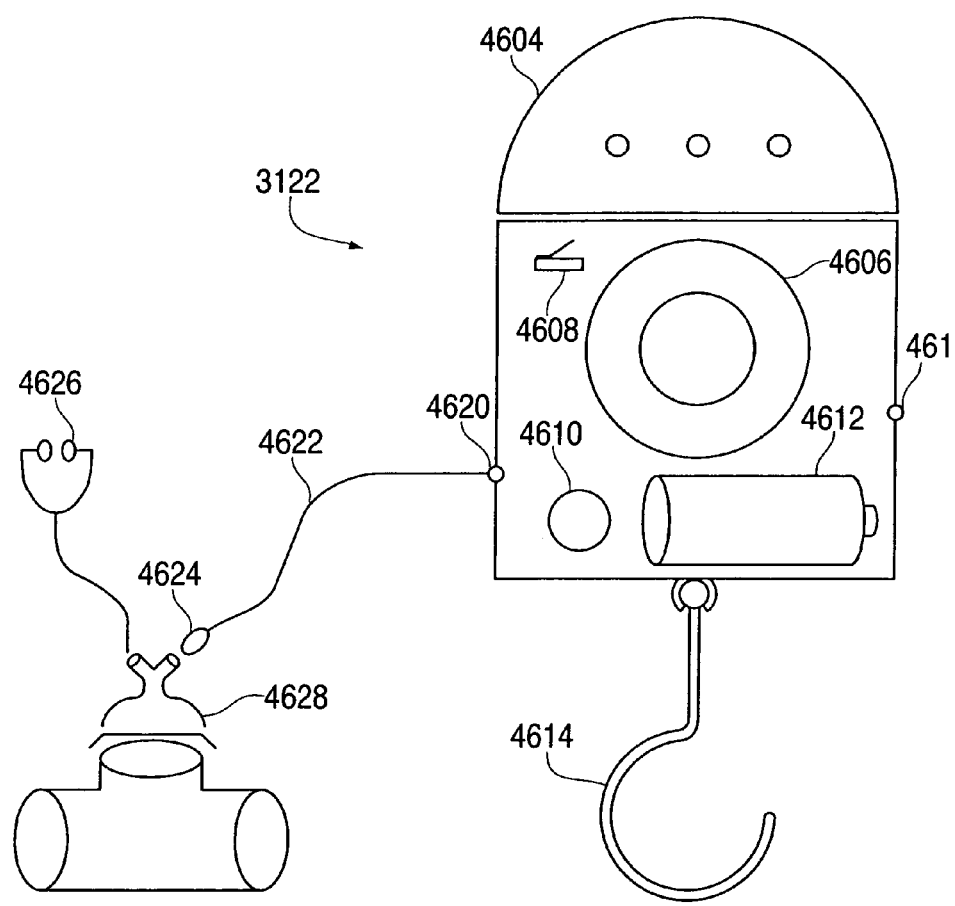
FIG. 46 illustrates an exemplary embodiment of a wireless electronic stethoscope transmitter, in accordance with the present invention.

FIG. 46 illustrates an exemplary embodiment of a wireless electronic stethoscope transmitter 3122 that may be used with the breathing circuit stethoscope in accordance with the present invention. As illustrated in FIG. 46, wireless electronic stethoscope transmitter 3122 includes a transmitter 4604, a speaker 4606, a transmitter on/off switch 4608, a speaker volume/on/off switch 4610, a power source 4612, an attachment device 4614, a signal input 4620 and signal output 4618. Transmitter 4604 may comprise any type of signal transmitter, for example an infrared transmitter, that is operable to transmit a signal to other monitoring equipment. Speaker 4606 provides an audio sound, i.e., breathing sounds of the patient, corresponding to the signal input by signal input 4620. Power source 4612 may include any type of portable power source, such as for example a battery or a capacitor, and may be rechargeable. Attachment device 4614, for example a hook, is operable to suspend portable breath sound monitor 4602, for example from an I.V. pole or bed rail. Attachment device 4614 may additionally include a swivel 4616 operable to permit the portable breath sound monitor to turn as needed while hanging from an IV pole or bed rail.

The speaker 4606 combined with the transmitter 4604 in portable breath sound monitor unit 4602 enables both units to be used at the same time or be separately turned off. An amplifier in wireless electronic stethoscope transmitter 3122 receives an input signal from input 4620 to amplify the breathing sounds of a patient to be broadcast through speaker 4606 and/or transmitter 4604. Wire 4622 connected to microphone 4624 enables the breathing sounds to be received from the circuit stethoscope 4628. Further, a stethoscope attachment 4626 may additionally be connected to the circuit stethoscope 4628. Wireless electronic stethoscope transmitter 3122 may be placed, for example on a table top or suspended by attachment device 4614 from a rail of I.V. pole. As discussed above, the hook swivels to allow the best orientation of the suspended unit.

Because the wireless electronic stethoscope transmitter 3122 includes an attachment device and a power source, the transmitter is moveable throughout the surgical theater. Furthermore, the wireless electronic stethoscope transmitter 3122 maybe attached to the patient's bed so that it may be transported with the patient as the patient is transported to different rooms throughout the entire recovery phase until the patient is well awake.

Transmitter 4604 may additionally transmit a signal corresponding to the input signal from input 4620 to headphones of a specific person. In this manner, speaker 4606 may be turned off so that the detected signal provided by input 4620 will not be outputted from speaker 4608 to avoid distracting others in the area.

Because of the nature of the use of the wireless electronic stethoscope transmitter 3122, transmitter 4604 need only be required to process a single channel of sound data. More particularly, stereophonic processing is not required, therefore the circuitry needed for the wireless electronic stethoscope transmitter 3122 is relatively uncomplicated and inexpensive to manufacture.

The shape of wireless electronic stethoscope transmitter 3122 in FIG. 46 is merely illustrative, and the shape may take any form in order to achieve the desired purposes discussed above. In an exemplary embodiment, a wireless electronic stethoscope transmitter may take the form of a ball comprising an outer shell made of impact resistant material, such as impact resistant rubber or impact resistant plastic. Such a ball shaped wireless electronic stethoscope transmitter 3122 maybe "tossed" or placed in the bed of a patient. Further, a foldable or collapsible handle may be incorporated into the ball shaped wireless electronic stethoscope such that once unfolded or extracted, the handle may be used to hang the ball shaped wireless electronic stethoscope on an I.V. pole or rail of a bed.

A launching pad may provide a fixing point for the relatively heavy and cumbersome gas circuit tubing. This fixing point allows greater mobility and less chance of dislodgement of the relatively light and flexible tubing which is the interface between the airway device and the circuit. The launching pad can be attached, for example, to the patient's chest such that it is repositionable to facilitate optimum placement.

Figure 33:
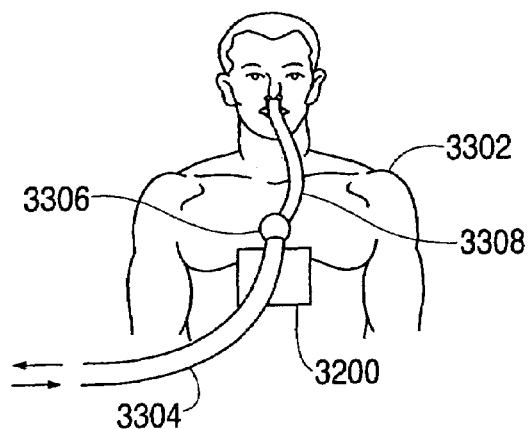
FIG. 33 illustrates the application of the launching pad illustrated in FIGS. 32A–32C.

FIG. 33 illustrates the use of a launching pad 3200. In particular, as illustrated in FIG. 33, launching pad 3200 fixes anesthesia circuit tubing 3304 to a patient 3302 such that the gas delivery tube 3308 can easily reach the patient. Pivotable connector 3306 provides a connecting portion between tubing 3308 and 3304.

Figure 32A:
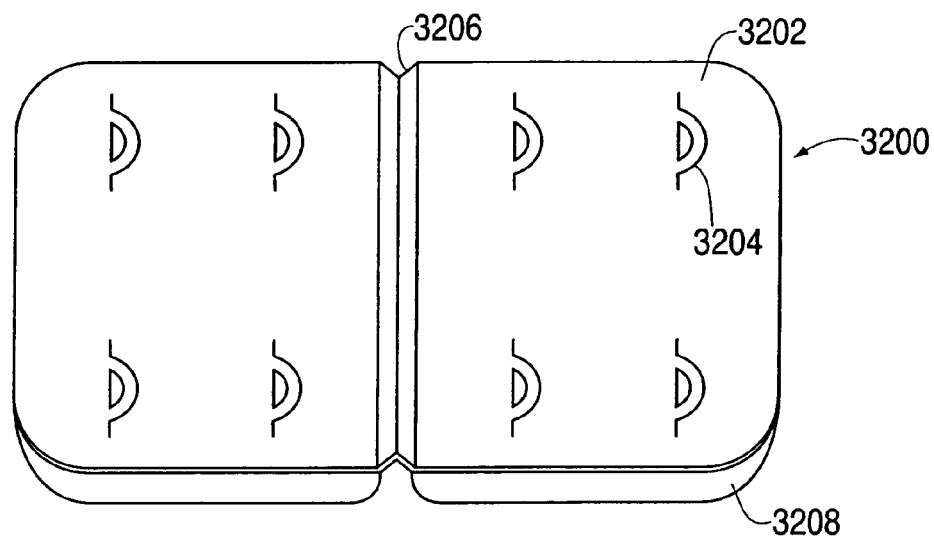
FIG. 32A illustrates an oblique view of an anesthesia or air circuit launching pad in accordance with the present invention.
Figure 32B:
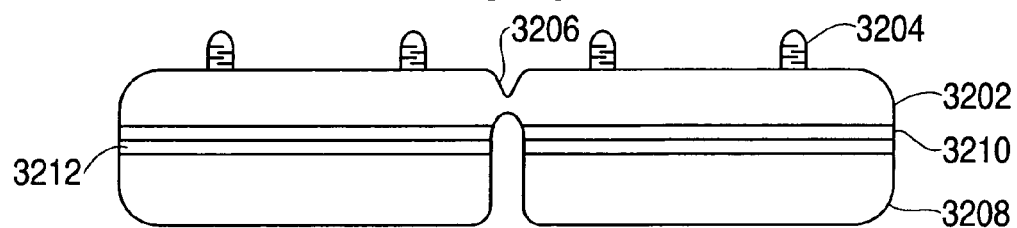
FIG. 32B is a side view of the launching pad of FIG. 32A.
Figure 32C:
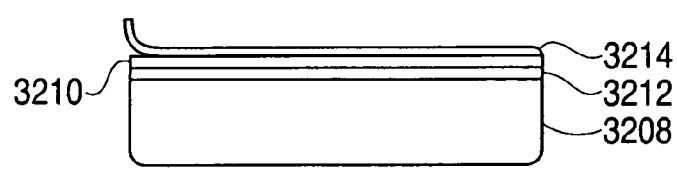
FIG. 32C is a side view of a portion of the launching pad of FIG. 32A.

FIGS. 32A–32C illustrate a launching pad in accordance with one embodiment of the present invention. Specifically, launching pad 3200 comprises a rigid pad 3202 having attachment portions 3204 and a hinge 3206. Attachment portions 3204 may comprise loops that permit tying down of the hoses of the anesthesia breathing circuit. Any other detachment devices, e.g., velcro, may be used. Hinge 3206 may comprise a flexion hinge to allow the pad to better conform to the patient's chest. Non-conductive adhesive gel 3208 adheres the launching pad to the patient. Separating layer 3212 separates adhesive gel 3208 from adhesive layer 3210. The separating layer may comprise material such as paper, plastic or any material capable of separating the two adhesive layers. As illustrated in FIG. 32C, removable backing 3214 can be pealed back so as to adhere adhesive layer 3210 to pad 3202. Accordingly, the adhesive non-conductive gel pads may be removed such that the rigid pad 3202 may be reusable.

Figure 36:
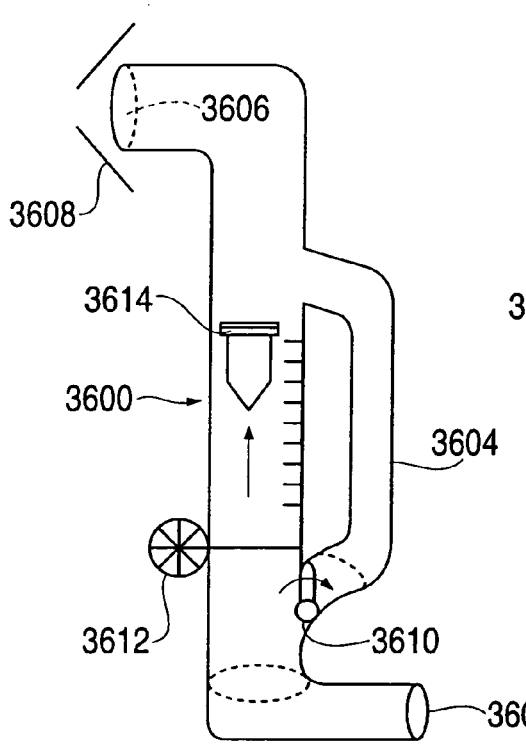
FIG. 36 is an exemplary embodiment of a continuous-pressure/constant-flow airflow generator in accordance with the present invention.
Figure 37:
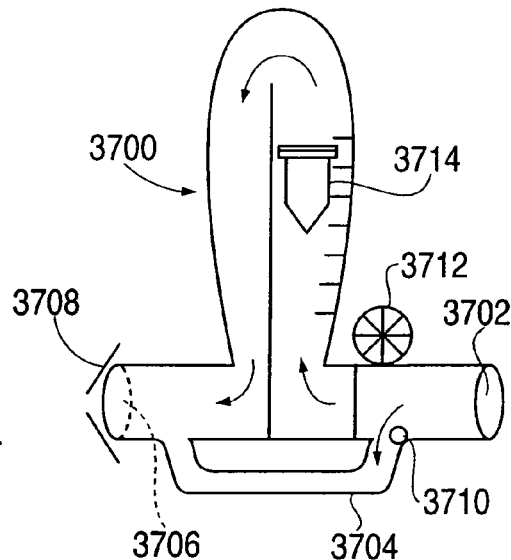
FIG. 37 is another exemplary embodiment of a continuous-pressure/continuous-flow airflow generator in accordance with the present invention.

Flow regulators may additionally be added throughout an anesthesia circuit in accordance with the present invention. FIGS. 36 and 37 provide exemplary embodiments of flow regulators in accordance with the present invention.

The first embodiment of a flow regulator as discussed above and as illustrated in FIG. 36, includes an input port 3602 that receives gas from the anesthesia and output port 3606 provides the gas back to the anesthesia breathing circuit after passing unit directional valve 3608 that prevents back flow of the gas into the flow regulator. A flow bobbin 3614 in a graduated conical cylinder is operable to move laterally in accordance with the amount of fluid flowing through the flow regulator. An adjusting knob 3602 is operable to control the amount of fluid flowing through the flow regulator by adjusting valve 3610 thereby permitting an amount of air to bypass through bypass 3604. Airflow leaving the constant airflow generator would fast pass through a "flush valve" which would allow two options: In the "normal" position airflow would be directed to the regulator. In the "flush" position, airflow would bypass the regulator and enter the breathing circuit at the full-flow capacity of the constant airflow generator. The purpose would be to fill the reservoir bag and the breathing circuit to capacity as fast as possible. The "flush" could be a push valve similar to that used an most anesthesia machines.

The regulator would be a variable-orifice resistor to airflow which, at a fixed pressure within the capacity of the constant airflow generator, would allow a fixed rate of airflow. There are several types of variable orifice regulators which might be used, but one similar to a standard conical-shaped screw-pin used on anesthesia machines would work well.

FIG. 37 is another embodiment of a fluid flow regulator. In particular, input port 3702 receives gas from the anesthesia circuit whereas output port 3706 returns the gas to the anesthesia circuit after passing unit directional valve 3708 that prevents back flow of the gas into the flow regulator.

A conventional spirometer may be used in conjunction with conventional breathing circuits. However, conventional spirometers have a problem measuring the amount of air leaving the lungs when used in conventional breathing circuits. When the breathing circuit is pressurized (e.g., with C-PAP), the flow characteristics within the breathing circuit are often altered in such a way as to make the conventional spirometers useless. For example, when mounted in the expiratory limb of the breathing circuit, a conventional electronic spirometer can be defeated by the continuous leakage flow that is typical of C-PAP applications. In particular, the flow indicator of the electronic spirometer typically goes off scale and does not indicate the rhythmic fluctuations of respiratory ebb and flow. On the other hand, a conventional mechanical spirometer such as a "Wright" spirometer works very well as the speed of the rotary needle gage fluctuates nicely to indicate precise volumes on inspiration and pauses on expiration. However, conventional mechanical spirometers are precision instruments, the expense of which might be hard to justify for the occasional user of an anesthesia C-PAP system.

Figure 47A:
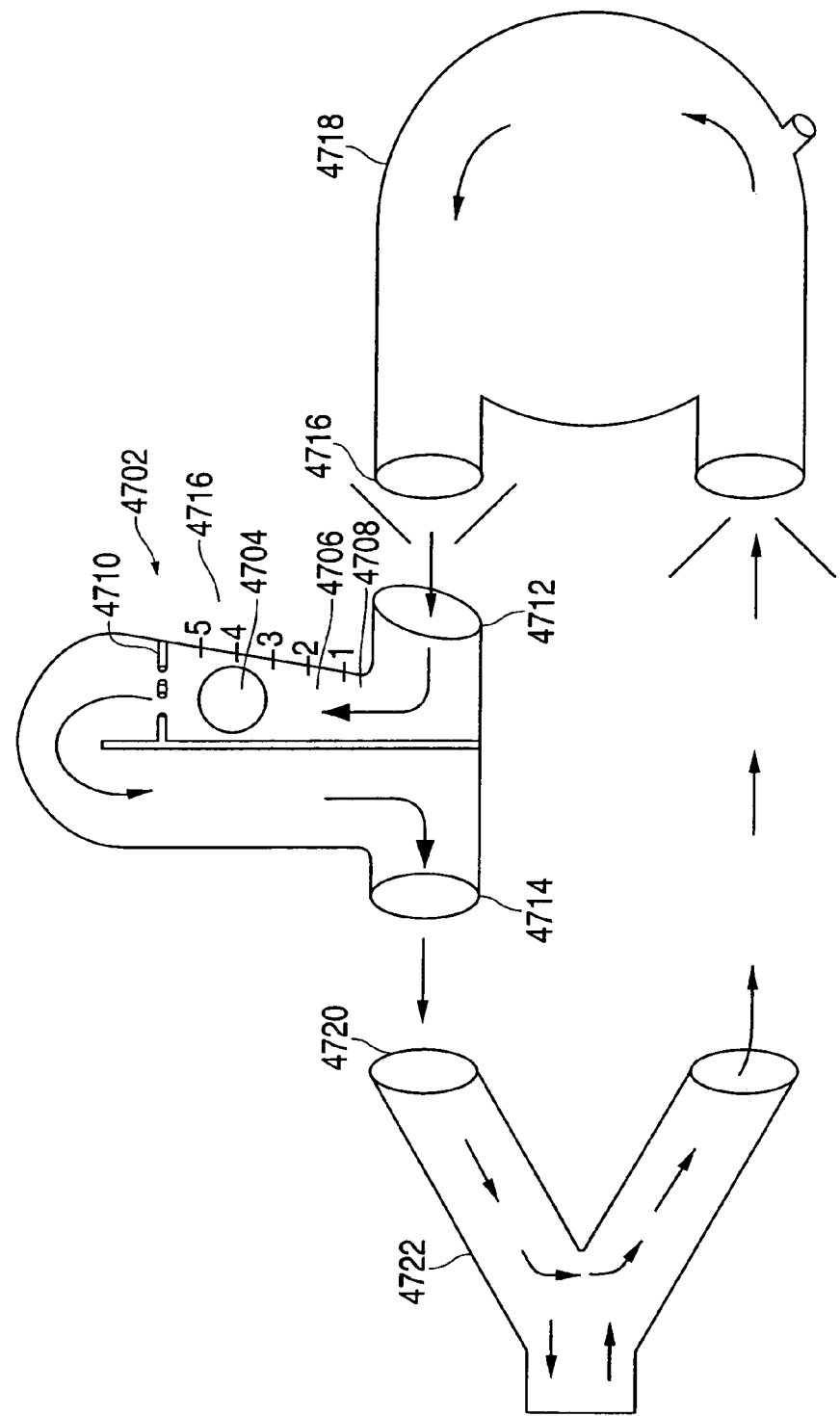

A spirometer in accordance with the present invention may be used with a breathing circuit to measure the volume of exhaled gas. FIGS. 47A and 47B illustrate two exemplary embodiments of spirometers for use with a breathing circuit in accordance with the present invention. As illustrated in FIGS. 47A and 47B, the spirometers, 4702 and 4724, respectively, are adapted to be placed in-line of a breathing circuit so as to communicate between the $CO_2$ scrubber 4718 and the patient breathing circuit connector 4722.

In first embodiment as depicted in FIG. 47A, the spirometer 4702 includes a light-weight float 4704 in a large, (e.g., 22 mm) tapered tube 4706 is operable to connect in-line with a breathing circuit. The float 4704 and tapered tube 4706 create a variable flow orifice typical of a flow meter. Spirometer 4702 is distinguished from conventional spirometers in that spirometer 4702 includes an input 4712 and an output 4714 designed to permit in-line connection with the breathing circuit. Further, the relatively large float 4704 and tapered tube 4706 permit flows in a low-pressure (e.g., 0–20 cm of water) C-PAP system to be accurately indicated with very low resistance to flow. A flow restrictor pin 4708 across tapered tube 4706 prevents float 4704 from occluding the tube.

Flow meters similar to that of spirometer 4702 have been employed in anesthesia machines, but are used in high-pressure (e.g., 55 mm of mercury) gas supply lines to the circuit, not in a setting in accordance with the present invention (0–22 cm of water). Further, a conventional device called an incentive spirometer is somewhat similar in construction to spirometer 4702, however the incentive spirometer is not designed to fit in-line with a breathing circuit.

In another embodiment as depicted in FIG. 47B, the spirometer 4724 includes, an in-line turbine 4732 and a housing 4730. Spirometer 4724 is included within the inspiratory limb of the breathing circuit such that input 4726 of spirometer 4724 is in communication with the output 4716 of $CO_2$ scrubber 4718 and such that output 4728 of spirometer 4724 is in communication with an input 4720 of patient breathing circuit connector 4722. In-line turbine 4732 has colored rotatable blades, or veins, that are clearly visible through a clear portion 4734 of housing 4730. The colored blades are operable to spin with a variable velocity indicative of the ebb and flow of inspiration superimposed upon a constant flow of gas through the breathing circuit. A side of the housing 4730 that is opposite the clear portion is colored a different color than that of the blades (or the opposite side may be opaque). Accordingly, as the flow of gas through the breathing circuit increases in volume, the rotational speed of the color blades increases thereby changing the perceived color of the spirometer 4724. Therefore, a viewer viewing the spinning colored blades, would recognize a change in intensity of the spinning blades as a result of the perceived changing color. This perceived change in color directly corresponds to the ebb and flow of the gas passing through in-line turbine 4732. Therefore, the perceived change in color informs the viewer of the breathing of the patient.

FIG. 48 illustrates a system for use in the home treatment of a patient with obstructive sleep apnea, in accordance with the present invention. The system of the present invention is more beneficial than conventional devices for obstructive sleep apnea because the system of the present invention is less cumbersome, includes a built-in humidifying system for inspired air, suppresses noise and further includes a reusable and user maintained heat and moisture exchanger.

The home treatment system 4802 includes a nasal vestibular device 4804, tubing 4806 a heat and moisture exchanger 4808 for conserving heat and moisture, a vent 4810, tubing 4816 and a C-PAP machine 4818. System 4802 may additionally include optional vent tubing 4812 and hollowed and vented ball 4814.

Tubing 4806 is much smaller than tubing used in conventional devices for obstructive sleep apnea. Specifically, conventional tubing for conventional devices, which are approximately 22 mm, have a lower resistance to air flow. On the contrary, tubing 4806, preferably in the range of 17–15 mm permits comfortable spontaneous respirations and is much less cumbersome. Moreover, any resistance to flow is negated by adjustment of the airflow generator, e.g., the C-PAP machine, powering the system.

Conventional devices for home treatment of obstructive sleep apnea include a vent that is as close to the nose of the user as possible in order to reduce the "dead space" that allows re-breathing of $CO_2$. On the contrary, in accordance with the present invention, vent 4810 includes a vent hole 4820 that is separated from the nose of the patient via at least the distance of tubing 4806 and the heat moisture exchanger 4808. The small added increase in dead space is comfortably and automatically compensated for in the spontaneous breathing patient. Further, optional vent tubing 4812 may be added to vent 4810 to direct the "hissing" sound of escaping air out of earshot of the user and others. Tubing 4812 may terminate at a large vented sphere 4814 in order to prevent air flow from becoming obstructed.

Heat and moisture exchanger 4808 may be configured in several ways. For example, it may comprise metal or plastic parts and be designed to be disassembled by the user. Further, it may include disposable water-trapping filters. Such filters may be of a reusable plastic or metal mesh or filter-plate which can be cleaned and sterilized by the user, for example by soaking in alcohol and rinsing thoroughly in water. FIGS. 49 and 50 illustrate examples of a mesh filter 4902 and filter-plate 5002, respectively.

There are several C-PAP machines marketed for home, hospital and camping use which employ 12 volt direct current systems with an optional battery adapter. A transport and auxiliary power assembly in accordance with the present invention, allows such C-PAP units to be used without modification in an attachment to a light-weight battery and handle assembly which allows the machine to be operated conveniently and continuously from the horizontal position to the vertical position while being transported from the operating room to the recovery room. FIGS. 51A–51C and 52 illustrate a transport and auxiliary power assembly for a C-PAP machine in accordance with the present invention.

Figure 51A:
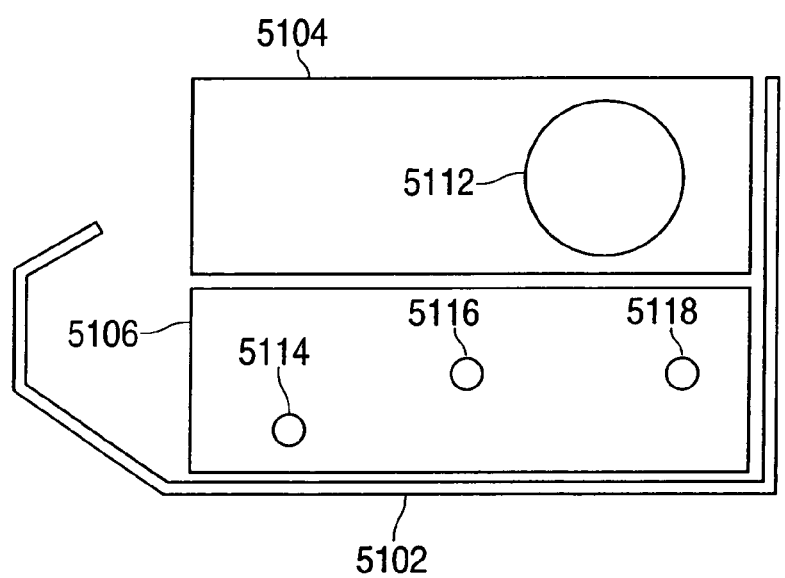
FIG. 51A–51C illustrate a transport and auxiliary power assembly, in accordance with the present invention.
Figure 51B:
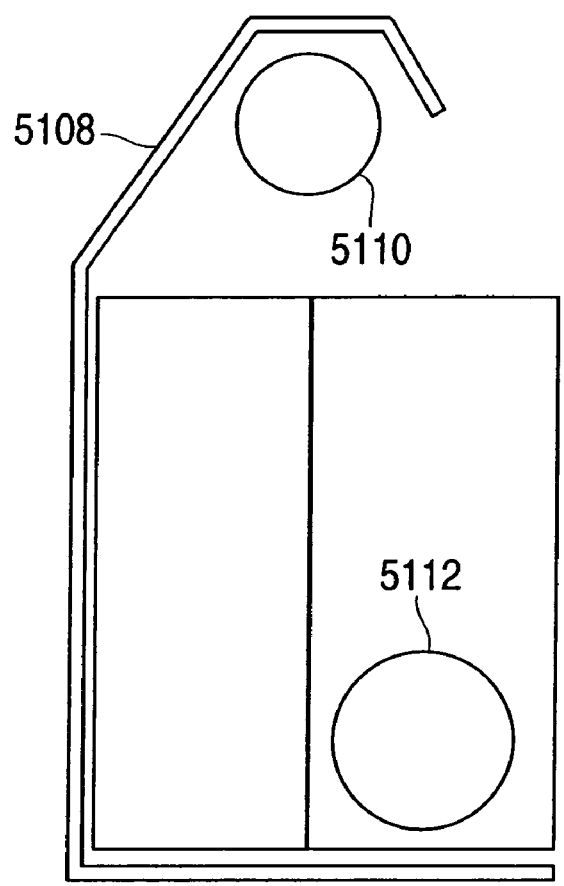
Figure 51C:
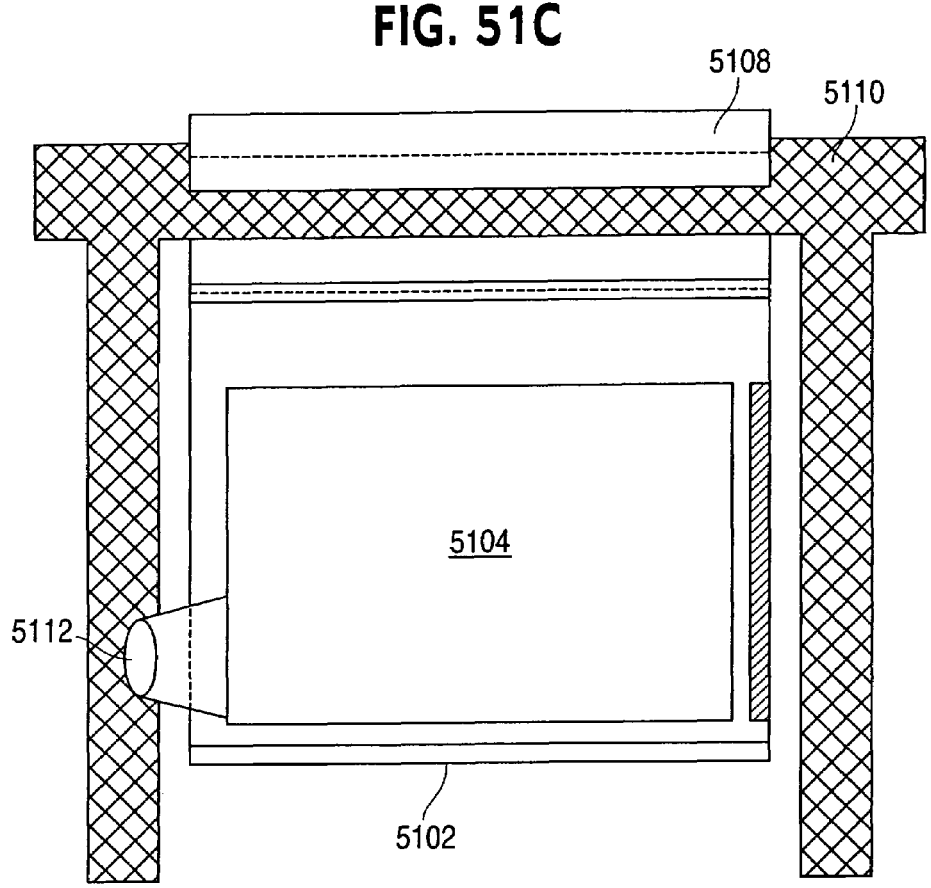

As illustrated in FIG. 51A, a carrying member 5102 is shaped as a four-sided platform to support a C-PAP machine 5104 and a battery pack 5106, mounted adjacent to C-PAP machine 5104 in a horizontal or "tabletop" position. During transport, as illustrated in FIG. 51B, the assembly is capable of being suspended vertically by a handle-rail-hook portion 5108 from a rail 5110 of a patient's bed. FIG. 51C illustrates a side view of carrying member 5102 when carried in the vertical position from a rail of a patient's bed. As illustrated in FIG. 51C, output 5112 of C-PAP machine 5104 is accessible for use during transport.

Battery pack 5106 and the C-PAP machine may be held together and to member 5102 by detachable fixation systems, such as small "velcro" fixation tabs, from which the components can easily be separated. Further, C-PAP machine 5104 and battery pack 5106 may be secured to carrying member 5102 via a strap enclosing the components.

Returning to FIG. 51A, battery pack 5106 may include a charging receptacle 5114 for charging the battery pack, a charging light 5116 for indicating when the battery pack is being charged and a warning light 5118 for indicating when the battery level is below a predetermined threshold.

Figure 52:
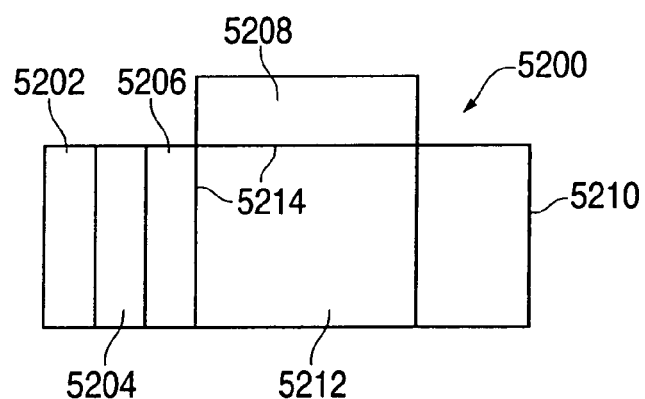
FIG. 52 illustrates an unfolded sheet a material to be used to form a housing for the transport and auxiliary power assembly illustrated in FIGS. 51A–51C.

FIG. 52 illustrates a single sheet 5200 of material that may be used to form carrying member 5102. Sections 5202, 5204, 5206, 5208, 5210 and 5212 are separated by a plurality folding lines 5214. Sections 5202, 5204 and 5206, once folded, form hand-rail-hook portion 5108. Portion 5208 forms a compartment in which electrical cords can be secured. Hand-rail-hook portion 5108 permits the assembly to be carried by hand or suspended from the rail of a structure.

The above embodiments of the present invention have been described with respect to specific features thereof. However, it is noted that the scope of the present invention is defined in the following claims, and should not be limited by the specific embodiments described above.

What is claimed is:

1. A monitoring system for use in a breathing circuit, said monitoring system being operable to monitor a patient's breathing, said monitoring system comprising:
   a nasal vestibular device comprising a nasal vestibular portion shaped and arranged to be inserted into and retained within a nasal vestibule of the patient without extending past the nasal vestibule towards the trachea of the patient, said nasal vestibular portion having a gas delivery port operable to deliver gas into the nasal vestibule, said nasal vestibular portion having a rigidity sufficient to cause said nasal vestibular portion to stay fixed in and to seal the nasal vestibule when gas is supplied to the nasal vestibule in an amount that causes pressure buildup that is sufficient to prevent obstruction of an airway in the patient during depression of at least a portion of the nervous system of the patient;
   a gas supply tube having a first end and a second end, said first end being connected to said nasal vestibular device to deliver gas to said nasal vestibular portion for effusion of the gas into the nasal vestibule via said gas delivery port; and
   a circuit stethoscope comprising a diaphragm and a t-connector having a first port, a second port and a third port,
   wherein said first port of said t-connector is designed to connect with a gas supply line of the breathing circuit,
   wherein said second port of said t-connector is connected to said second end of said gas supply tube, and
   wherein said diaphragm is disposed on said third port of said t-connector.

2. The monitoring system of claim 1, wherein said circuit stethoscope further comprises a bell cap,
   wherein said diaphragm is disposed between said third port of said t-connector and said bell cap, and
   wherein said bell cap includes a port for receiving a sound detecting device.

3. The monitoring system of claim 2, further comprising a stethoscope transmitter in communication with said bell cap.

4. The monitoring system of claim 1, wherein said nasal vestibular portion comprises a trimmable portion having raised marks for providing a measuring system to aid in incrementally trimming said trimmable portion.

5. The monitoring system of claim 1, wherein said nasal vestibular portion has a protruding portion having a diameter larger than a diameter of said gas supply tube so as to be retained within the nasal vestibule, said raised marks being located on said protruding portion.

6. The monitoring system of claim 5, wherein said protruding portion comprises a rounded protruding portion.

7. The monitoring system of claim 5, wherein said protruding portion comprises a bell-shaped protruding portion.

8. The monitoring system of claim 1, wherein said nasal vestibular portion has a protruding portion having a diameter larger than a diameter of said gas supply tube so as to be retained within the nasal vestibule.

* * * * *